(12) United States Patent
Hecht et al.

(10) Patent No.: US 9,040,673 B2
(45) Date of Patent: May 26, 2015

(54) SYNTHESIS AND IDENTIFICATION OF NOVEL RSK-SPECIFIC INHIBITORS

(75) Inventors: Sidney M. Hecht, Charlottesville, VA (US); Deborah A. Lannigan-Macara, Charlottesville, VA (US); Jeffrey Allan Smith, Earlysville, VA (US); George A. O'Doherty, Charlottesville, VA (US); Michael Kenneth Hilinski, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 282 days.

(21) Appl. No.: 13/390,389

(22) PCT Filed: Aug. 13, 2010

(86) PCT No.: PCT/US2010/045440
§ 371 (c)(1),
(2), (4) Date: Jun. 14, 2012

(87) PCT Pub. No.: WO2011/019995
PCT Pub. Date: Feb. 17, 2011

(65) Prior Publication Data
US 2012/0245112 A1 Sep. 27, 2012

Related U.S. Application Data

(60) Provisional application No. 61/274,236, filed on Aug. 14, 2009.

(51) Int. Cl.
*C07H 17/075* (2006.01)
*A61K 31/7048* (2006.01)
*A61K 31/535* (2006.01)

(52) U.S. Cl.
CPC ............ *A61K 31/535* (2013.01); *C07H 17/075* (2013.01); *A61K 31/7048* (2013.01)

(58) Field of Classification Search
CPC .................................. C07H 17/07; C07H 7/02
USPC ................................................ 536/8; 514/27
See application file for complete search history.

(56) References Cited

U.S. PATENT DOCUMENTS

| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 2007/0049539 A1 | 3/2007 | Smith et al. |
| 2009/0082400 A1 | 3/2009 | Lee et al. |

FOREIGN PATENT DOCUMENTS

| WO | WO03/105766 | 12/2003 |
| WO | WO2007/139778 | 12/2007 |
| WO | WO2009/023053 | 2/2009 |

OTHER PUBLICATIONS

Rehman et al., Natural Product Research, 2007, 21(9), pp. 775-781.*
Trivier et al., Nature, 1996, 384, pp. 567-570.*
Nandan et al., Infection and Immunity, 1999, 67(8), pp. 4055-4063.*
PCT Search Report and Written Opinion for PCT/US2010/045440, completed May 2, 2012.
Cieslik, Katarzyna A., et al., "Inhibition of p90 Ribosomal S6 Kinase-Mediated CCAAT/Enhancer-Binding Protein Beta Activation and Cyclooxygenase-2 Expression by Salicylate", 2005, The Journal of Biological Chemistry, vol. 280, No. 18, pp. 18411-18417.
Hackstadt, Ted, "Redirection of Host Vesicle Trafficking Pathways by Intracellular Parasites", 2000, Traffic, No. 1, pp. 93-99.
Hemmer, Wolfram, et al., "Recombinant Strategies for Rapid Purfication of Catalytic Subunits of cAMP-Dependent Protein Kinase", 1997, Analytical Biochemistry, No. 245, pp. 115-155.
Joel, Peteranne B., et al., "Estradiol-Induced Phosphorylation of Serine 118 in the Estrogen Receptor Is Independent of p. 42/p. 44 Mitogen-Activated Protein Kinase", May 1998, Journal of Biological Chemistry, vol. 273, No. 21, pp. 13317-13323.
Kahn, Richard A., et al., "Cellular Hijacking: A Common Strategy for Microbial Infection", Jun. 2002, Trends in Biochemical Sciences, vol. 27, No. 6, pp. 308-314.
Lerm, M., et al., "Leishmania Donovani Requires Functional Cdc42 and Rac1 to Prevent Phagosomal Maturation", May 2006, Infection and Immunity, vol. 74, No. 5, pp. 2613-2618.
Maloney, David J., et al., "Synthesis of a Potent and Selective Inhibitor of P90 Rsk", 2005, Organic Letters, vol. 7, No. 6, pp. 1097-1099.
Scott, C.C., et al., "Phagosome Maturation: A Few Bugs in the System", 2003, J. Membrane Biol., No. 193, pp. 137-152.
Shan, Mingde, et al., "De Novo Asymmetric Syntheses of SL0101 and its Analogues via a Palladium-Catalyzed Glycosylation", 2006, Organic Letters, vol. 8, No. 22, pp. 5149-5152.
Shan, Mingde, et al., "Synthesis of SL0101 Carbasugar Analogues: Carbasugars via Pd-Catalyzed Cyclitolization and Post-Cyclitolization Transformations", 2010, Organic Letters, vol. 12, No. 13, pp. 2986-2989.
Shan, Mingde, et al., "Synthesis of Carbasugar C-1 Phosphates via Pd-Catalyzed Cyclopropanol Ring Opening", 2008, Organic Letters, vol. 10, No. 16, pp. 3381-3384.
Shan, Mingde, et al., "Synthesis of Cyclitols via Cyclopropanation/Palladium-Catalyzed Ring Opening", 2008, Synthesis, No. 19, pp. 3171-3179.
Vanrheenen, V., et al., An Improved Catalytic OsO4 Oxidation of Olefins to CIS-1,2- Glycols Using Tertiary Amine Oxides as the Oxidant, 1976, Tetrahedron Letters, No. 23, pp. 1973-1976.

* cited by examiner

*Primary Examiner* — Jonathan S Lau
(74) *Attorney, Agent, or Firm* — Barnes & Thornburg LLP

(57) ABSTRACT

A composition comprising an SL0101 [kaempferol 3-O-(3", 4"-di-O-acetyl-α-L-rhamnopyranoside)] derivative compound that has enhanced ability to inhibit RSK activity, relative to the parent compound is provided. The compounds have utility for treating any disease or conditions characterized or associated with excess or undesirable RSK activity. For example the RSK inhibitors of the present invention can be used to reduce the proliferation of neoplastic cells or for inhibiting the establishment or maintenance of an intracellular pathogenic infection by pathogens whose pathogenicity derives in part from the pathogen's ability to impede endosomal/phagosomal maturation in the host cell.

13 Claims, 18 Drawing Sheets

Figure 1:
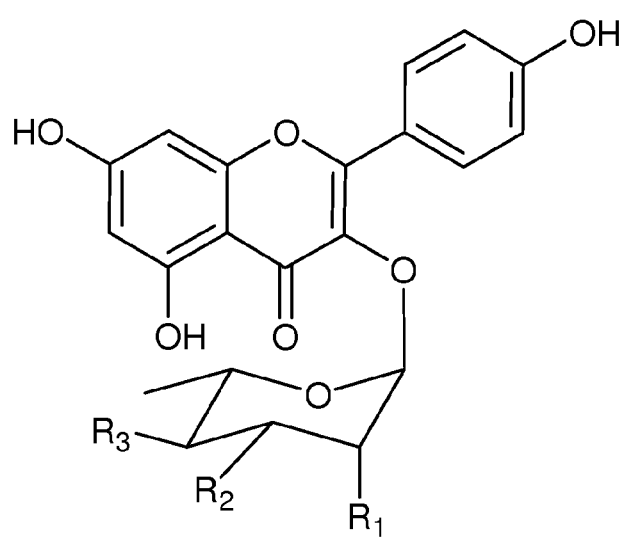

|  | R₁ | R₂ | R₃ |
|---|---|---|---|
| SL0101 (1) | OH | OAc | OAc |
| 2",4"-di-O-acetyl SL0101 | OAc | OH | OAc |
| 4"-mono-O-acetyl SL0101 | OH | OH | OAc |

SYNTHESIS AND IDENTIFICATION OF NOVEL RSK-SPECIFIC INHIBITORS

CROSS REFERENCE TO RELATED APPLICATIONS

This application is a U.S. national application under 37 C.F.R. §371(b) of International Application Serial No. PCT/US2010/045440 filed Aug. 13, 2010 which claims priority to U.S. Provisional Application Ser. No. 61/274,236 filed on Aug. 14, 2009, the complete disclosures of which is are incorporated herein by reference.

BACKGROUND

Signal transduction pathways relay information from a variety of different stimuli leading to multiple cellular responses. Consequently, such pathways have attracted a great deal of attention as potential targets for therapeutic intervention. The Mitogen-activated Protein Kinase (MAPK) signaling pathway is one key pathway that transduces a large variety of external signals, leading to cellular responses that include growth, differentiation, inflammation and apoptosis. Accordingly, MAPK is activated by several diverse signals under normal conditions. However, improper regulation of MAPK, including hyperactivity, has been associated with many diseased states. More particularly, improper regulation of the Mitogen-activated Protein Kinase (MAPK) pathway is a distinguishing characteristic in many tumors as well as neurological diseased states such as epilepsy.

p90 Ribosomal S6 Kinase (RSK) is a serine/threonine kinase that is a downstream component of the Mitogen-activated Protein Kinase (MAPK) signaling pathway. Therefore, unregulated stimulation of the MAPK pathway results in unregulated RSK catalytic activity. The contribution of upstream components such as Epidermal Growth Factor Receptor (EGFR) and the products of the proto-oncogenes c-src, ras, and raf to activate the MAPK pathway, resulting in physiological responses by the cell that are associated with diseased states, have been well documented. However, the extent to which these physiological responses function through RSK is unknown.

The paucity of data concerning key biological roles of the Ser/Thr protein kinase RSK family in somatic cells results primarily from the difficulty in distinguishing RSK function from those of MAPK itself and of the many other downstream MAPK effectors. This difficulty has arisen because of the lack of any RSK specific inhibitors. Accordingly, a RSK specific inhibitor is highly desirable for use as a tool for investigating RSK function under normal conditions and under diseased conditions in which regulation of the MAPK signaling pathway has been compromised. One aspect of the present disclosure provides a method for using compositions comprising such inhibitors for the treatment of diseases associated with elevated RSK activity.

Many intracellular pathogens hijacks the host cell's signaling events and trafficking machinery for establishment and maintenance of infection (Kahn, et al., 2002. Trends Biochem Sci 27:308-14). Thus, the host cell signaling events essential for establishing and maintaining infection provide attractive targets for novel anti-infective agents. Accordingly, one set of targets for new anti-infective agents is the signaling events involved in endosomal/phagosomal maturation. For intracellular pathogens to survive in the host cell they must disrupt or avoid the microbicidal machinery. This often involves inhibiting maturation of the endocytotic vesicles and fusion with the lysosomes (See for example, Hackstadt, T. 2000. Traffic 1:93-9 and Scott, et al., 2003. J Membr Biol 193:137-52). Thus, compounds that inhibit the host-cell's signaling events used by the pathogen to impede endosomal/phagosomal maturation would promote fusion of the endocytotic and lysosomal vesicles restoring microbicidal function to the host cell. Applicants have discovered that RSK activity can be inhibited as a means of preventing pathogen disruption of endosomal/phagosomal maturation.

Anti-angiogenic therapy is currently in use to treat multiple pathologies. As disclosed herein, applicants have discovered that RSK activity is required for endothelial cell migration, and accordingly, inhibiting RSK activity represents a novel method for inhibiting angiogenesis. The purpose of the present disclosure is not to overcome shortcomings that have been identified with previous anti-angiogenic treatments. This present disclosure adds to the options for anti-angiogenic treatments and allows for new unique combinations of anti-angiogenic therapeutics.

As disclosed herein applicants have discovered a new set of RSK specific inhibitory compounds that can be used to treat various conditions associated with undesirable RSK activity.

SUMMARY

In accordance with one embodiment a composition is provided that comprises a RSK specific inhibitory compound. The RSK inhibitors disclosed herein are derivatives of kaempferol 3-O-(3",4"-di-O-acetyl-.alpha.-L-rhamnopyranoside), referred to herein as SL0101:

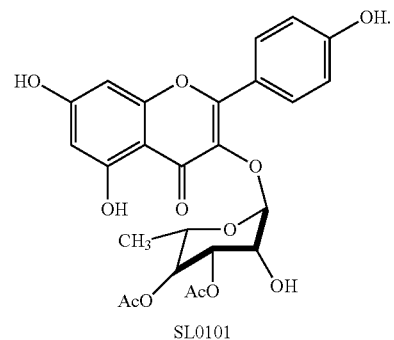

SL0101

SL0101 has been described in published US application no. 20070049539, and international applications PCT/US03/18734 and PCT/US07/12156, the disclosures of which are each incorporated herein by reference, as an inhibitor of RSK activity. The novel derivatives disclosed herein have surprisingly improved RSK-activity, relative to the parent compound, SL0101. In addition to improved the inhibitory activity, these new analogues are also anticipated to have improved pharmacokinetic properties (e.g., improved metabolic stability, solubility and membrane permeability), which in turn will make these new compounds better drugs for the treatment of RSK related diseases (e.g., cancer and infection by intracellular pathogens like *Yersinia*). More particularly, compositions comprising the novel SL0101 RSK inhibitors disclosed herein can be used to target RSK activity for therapeutic intervention in diseased states in which the disease or the symptoms can be ameliorated by inhibition of RSK catalytic activity.

In accordance with one embodiment a RSK specific inhibitory compound is provided comprising a compound of the general structure:

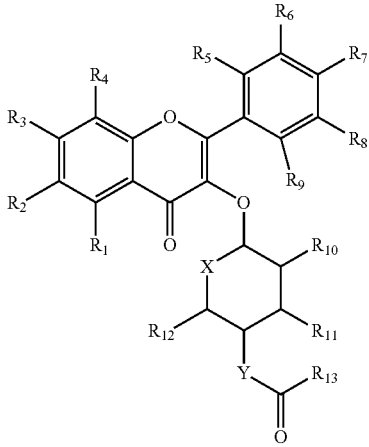

I wherein $R_1$, $R_2$, $R_3$, $R_4$, $R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{12}$ is selected from the group consisting of $C_1$-$C_4$ alkyl, $C_1$-$C_4$ alkoxy, and [$C_0$-$C_4$ alkyl]$CHR_{18}R_{19}$;

$R_{13}$ is selected from the group consisting of hydrogen, hydroxyl, and $(CH_2)_m CR_{18}R_{19} (CH_2)_n H$;

m and n are independently an integer from 0-3;

X is selected from the group consisting of O, NH, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl; and $R_{15}$ is selected from the group consisting of hydrogen, halo, hydroxyl, and $C_1$-$C_4$ alkyl;

$R_{16}$, $R_{17}$, $R_{18}$ and $R_{19}$ are independently and $C_1$-$C_4$ alkoxy, with the proviso that when X is O, $R_{12}$ is not $CH_2$ and when X is $CH_2$, at least one of $R_{10}$ and $R_{11}$ is hydroxyl. In one embodiment the RSK inhibitory compound comprises a compound of Formula I wherein $R_{12}$ is $C_2$-$C_4$ alkyl. In one embodiment the RSK inhibitory compound comprises a compound of Formula I wherein X is selected from the group consisting of O, $NR_{14}$, $CHR_{14}$, and $CF_2$ and Y is selected from the group consisting of $NR_{15}$, and $CR_{16}R_{17}$. In a further embodiment $R_2$ and $R_4$ are each hydrogen, $R_1$, $R_3$ and $R_7$ are each hydroxyl and $R_{12}$ is $C_2$-$C_4$ alkyl.

In one embodiment a RSK specific inhibitory compound is provided comprising a compound of the general structure:

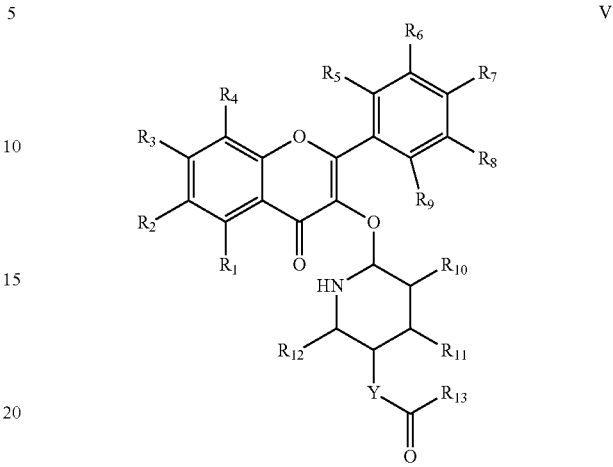

V wherein $R_1$, $R_2$, $R_3$, $R_4$, $R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{12}$ is selected from the group consisting of $C_1$-$C_4$ alkyl, $C_1$-$C_4$ alkoxy, and [$C_0$-$C_4$ alkyl]$CH_2R_{18}$;

$R_{13}$ is selected from the group consisting of hydrogen, hydroxyl, and $(CH_2)_m CR_{18}R_{19} (CH_2)_n H$;

m and n are independently an integer from 0-3;

Y is selected from the group consisting of O, $NR_{15}$, and $CR_{16}R_{17}$;

$R_{14}$ is selected from the group consisting of hydrogen, and $C_1$-$C_4$ alkyl;

$R_{15}$, $R_{18}$ and $R_{19}$ are independently selected from the group consisting of hydrogen, halo, hydroxyl, $C_1$-$C_4$ alkyl and $C_1$-$C_4$ alkoxy; and $R_{16}$ and $R_{17}$ are independently selected from the group consisting of hydrogen, halo, hydroxyl, $C_1$-$C_4$ alkyl and $C_1$-$C_4$ alkoxy. In one embodiment the RSK inhibitory compound comprises a compound of Formula I or V wherein $R_2$ and $R_4$ are each hydrogen, $R_1$, $R_3$, $R_5$, $R_6$, $R_7$, $R_8$ and $R_9$ are independently selected from the group consisting of hydrogen, fluorine, hydroxyl, —$OCOR_{14}$, —$COR_{14}$ and $C_1$-$C_4$ alkoxy, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy. In one embodiment the RSK inhibitory compound comprises a compound of Formula I or V wherein $R_2$, $R_4$, $R_5$, $R_6$, $R_8$ and $R_9$ are each hydrogen or fluorine, $R_1$, $R_3$, and $R_7$, are each hydroxyl, $R_{10}$ and $R_{11}$ are independently hydroxyl or —$OCOR_{14}$ and $R_{12}$ is $C_1$-$C_4$ alkyl. In a further embodiment the RSK inhibitory compound comprises a compound of Formula I or V wherein $R_2$, $R_4$, $R_5$, $R_6$, $R_8$ and $R_9$ are each hydrogen or fluorine, $R_1$, $R_3$, and $R_7$, are each hydroxyl, $R_{10}$ and $R_{11}$ are independently hydroxyl or —$OCOR_{14}$, $R_{12}$ is $C_2$-$C_4$ alkyl and Y is oxygen and $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In a further embodiment a RSK specific inhibitory compound is provided comprising a compound of Formula IV:

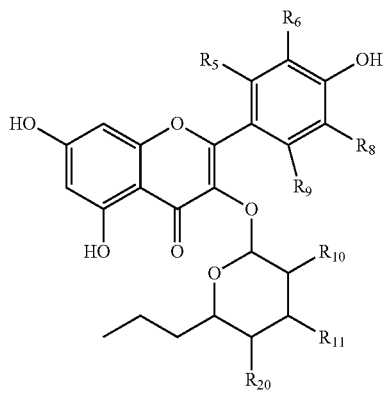

wherein $R_5$, $R_6$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of —$COR_{14}$ and hydroxyl, and $R_{14}$ is selected from the group consisting of hydrogen and $C_1$-$C_4$ alkyl. In a further embodiment $R_5$, $R_6$, $R_8$ and $R_9$ are each hydrogen and at least one of $R_{10}$, $R_{11}$ and $R_{20}$ is $COCH_3$ and at least one of $R_{10}$, $R_{11}$ and $R_{20}$ is hydroxyl. In a further embodiment $R_{20}$ is $COCH_3$ and one of $R_{10}$ and $R_{11}$ is —$COCH_3$ and the other is hydroxyl.

Inhibition of RSK by the present compounds has been discovered to halt the proliferation of cancer cell lines while having little effect on the proliferation rate of normal cells. In accordance with one embodiment a method of inhibiting the proliferation of neoplastic cells is provided wherein the method comprises the steps of contacting neoplastic cells with a compound of the general structure of Formula I. In one embodiment a composition comprising compounds of the general structure of Formula IV are administered to inhibit the proliferation of neoplastic cells and to treat cancer.

In another embodiment, the RSK inhibitory SL0101 derivatives can be used in a novel method of inhibiting endothelial cell migration. Inhibition of endothelial cell migration inhibits the ability of endothelial cells to conduct the initial steps needed for angiogenesis, leading to alleviation of the symptoms and restoration of the health of patients suffering from diseases associated with inappropriate angiogenic activity. Accordingly, in one embodiment a composition comprising a RSK inhibitory SL0101 analog is placed in contact with endothelial cells of a patient in need of reduced angiogenic activity. For example, pharmaceutical compositions comprising a RSK specific inhibitor can be used to treat diseases as diverse as cancer, arthritis and diabetic retinopathy.

In accordance with one embodiment the SL0101 derivatives disclosed herein are used to combat the establishment and maintenance of an infection by a pathogenic microorganism. RSK activity is involved in endosomal/phagosomal maturation that some pathogens use to impede endosome/phagosome maturation through a mechanism that utilizes RSK activity. Therefore, inhibiting the activity of RSK decreases the pathogen's ability to impede endosome/phagosome maturation and can improve the host organism's ability to resist and/or mitigate pathogen infection. More particularly, the present application discloses that an inhibitor of RSK activity protects the host-cell's cytoskeleton from pathogen-induced actin reorganization, and furthermore that a RSK inhibitor reduces the viability of internalized *Y. pseudotuberculosis* through an indirect mechanism. In accordance with one embodiment, the present invention provides compositions and methods for inhibiting native RSK activity in the cells of a potential host organism as a means of interfering with the ability of a pathogen to avoid the microbicidal machinery of the host.

BRIEF DESCRIPTION OF THE DRAWINGS

FIG. 1: Molecular structure of SL0101-1, SL0101-2 (2",4"-di-O-acetyl SL0101) and SL0101-3 (4"-mono-O-acetyl SL0101).

FIGS. 2A & 2B Analysis of LPS stimulated cytokine expression. J774A1 cells were treated with growth medium containing 1 μg/ml LPS and either vehicle or 60 μM SL0101. Reactions were terminated with 2×-SDS lysis buffer at indicated time points and the lysates were immunoblotted. LPS treatment activates p42/44 MAPK (Erk 1/2) and does not alter the levels of RSK 1 or RSK2 (FIG. 2A). LPS treatment also increased expression of the cytokines, TNFα and IL-113 (FIG. 2B). Equal loading is demonstrated by the Ran immunoblot.

FIGS. 3A & 3B RSK inhibition abrogates LPS-induced iNOS expression. J774A1 cells (FIG. 3A) and mouse primary peritoneal macrophages (FIG. 3B) were treated with growth medium containing 1 μg/ml LPS and either vehicle or 60 μM SL0101. Twenty-four hours after treatment, reactions were terminated with 2×-SDS lysis buffer and the lysates were immunoblotted. LPS treatment stimulates iNOS expression however, simultaneous contact with LPS and a RSK inhibitor abrogates iNOS expression in both the J774A.1 cells (FIG. 3A) and the primary macrophages (FIG. 3B). Equal loading is demonstrated by the Ran immunoblot.

FIGS. 4A & 4B graphically illustrate the results of experiments demonstrating that inhibition of RSK activity results in reduced viability of internalized *Y. pseudotuberculosis*. FIG. 4A presents data from J774A.1 cells (murine macrophage cell line, ATCC number TIB-67) and primary murine peritoneal macrophages incubated with 60 μM SL0101 or vehicle for 4 hours prior to infection with *Yersinia pseudotuberculosis* (MOI=25). Following a 60 minute incubation, bacteria not attached to the macrophages were removed by washing with fresh growth medium. Twenty-three hours after removal of the excess bacteria, the cells were washed with fresh growth medium and lysed in a hypotonic buffer. The lysate was used to inoculate bacterial cultures. The bacteria were cultured on solid LB agar or in liquid LB medium, and the data presented in FIG. 4A is based on the results using solid LB agar as the media. Fewer viable bacteria are isolated from SL0101-treated cells than that isolated from vehicle-treated cells. FIG. 4B represents the results of culturing *Y. pseudotuberculosis* in liquid LB medium in the presence of vehicle or 60 μM SL0101. The rate of *Y. pseudotuberculosis* growth in the presence of SL0101 was identical to that in the presence of vehicle. Thus, SL0101 does not directly alter the growth of *Y. pseudotuberculosis.*

FIG. 5A-5C graphically illustrates that 3Ac-SL0101 selectively inhibits MCF-7 breast cancer cell proliferation, but not nontransformed breast cell proliferation. (5A) MCF-7 cells were treated with vehicle or the indicated concentration of kaempferol 3-O-(3",4"-di-O-butyryl-.alpha.-L-rhamnopyranoside) (Bu-SL0101) and kaempferol 3-O-(2",3",4"-tri-O-acetyl-.alpha.-L-rhamnopyranoside) (3Ac-SL0101) and SL0101; (5B) MCF-7 (cancer) and MCF-10A (nontransformed) cells were treated with vehicle or the indicated concentration of Bu-SL0101; or (5C) MCF-7 and MCF-10A cells were treated with vehicle or the indicated concentration of 3Ac-SL0101. The cell number was measured after 48 h of treatment. Values given are the fold proliferation as a percentage of that observed with vehicle-treated cells. Points, mean (n=2 in quadruplicate); bars=SD.

Figure 6:
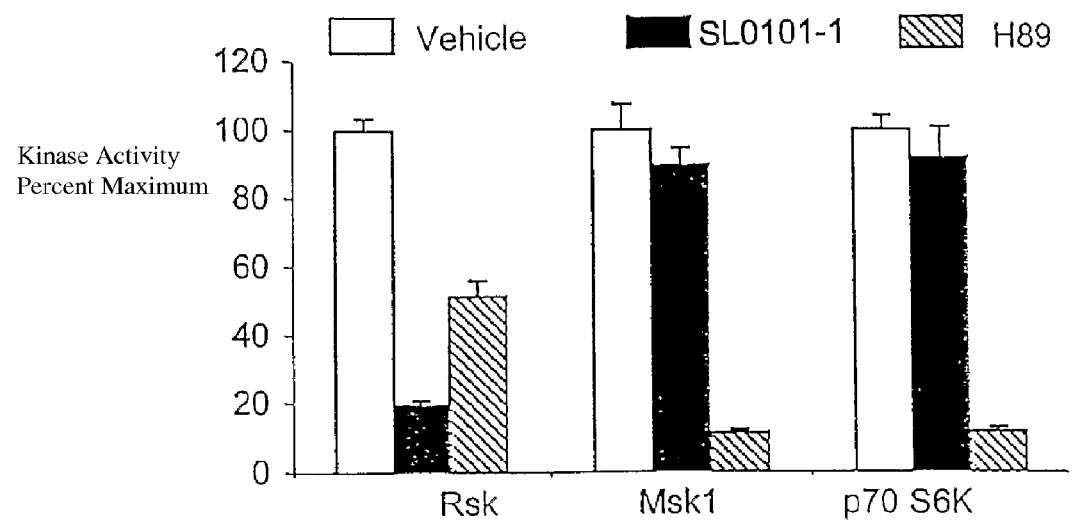

FIG. 6. Purified SL0101-1 specifically inhibits RSK2 activity in vitro. Vehicle or inhibitor (5 μM) was added to the kinase mix containing 5 nM of the indicated purified kinases. The reaction was allowed to proceed for 30 mins at room temperature and the data were normalized to the kinase activity obtained in the presence of vehicle.

Figure 7A:
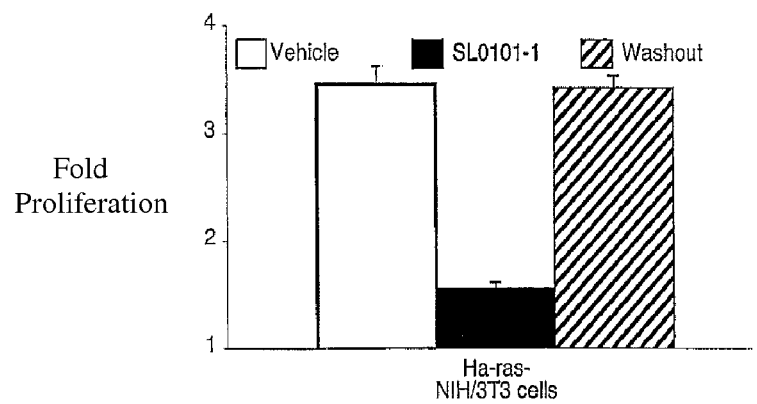
Figure 7B:
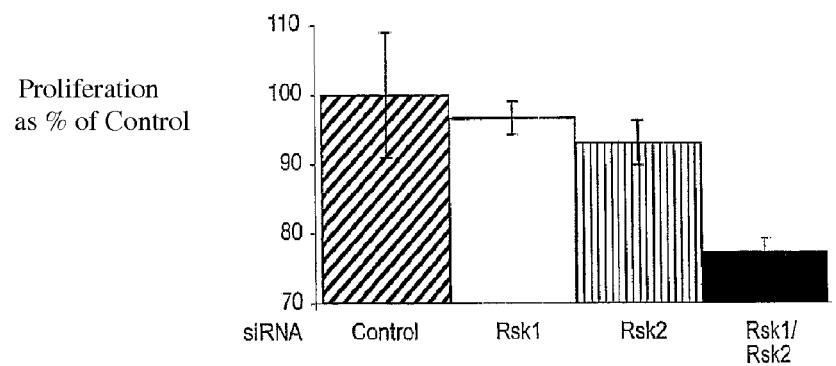

FIGS. 7A & 7B. SL0101-1 inhibition of cell proliferation is reversible. FIG. 7A: Ha-Ras-transformed cells were treated with vehicle or 50 μM SL0101-1. After 48 hr the medium was replaced and cells previously incubated with vehicle were maintained in vehicle. Cells that had previously been incubated with SL0101-1 were treated with either SL0101-1 or vehicle (washout). Cell viability was measured 48 hr later. FIG. 7B: Determination of siRNA to inhibit cancer cell proliferation. Duplex siRNAs to a sequence in the bluescript plasmid (Control), RSK1, RSK2 or RSK1 and RSK2 were transfected into MCF-7 cells. Medium was replaced 24 hr post-transfection and the cells incubated for an additional 48 hr prior to measuring cell viability.

Figure 8A:
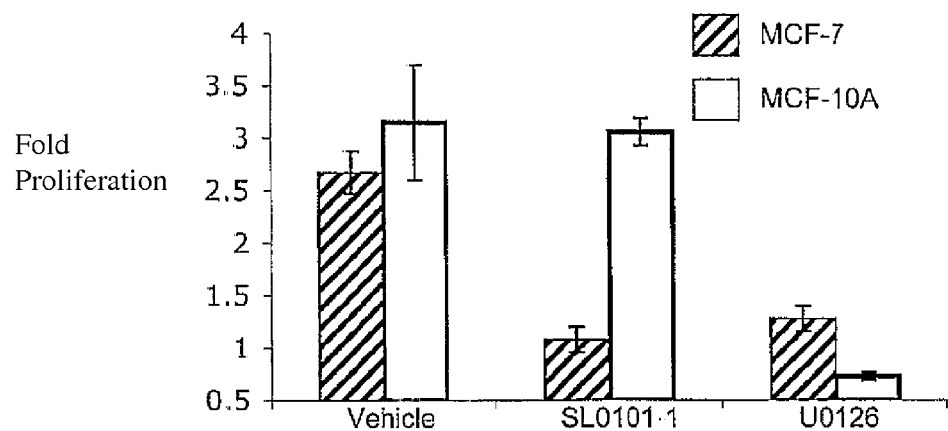
Figure 8B:
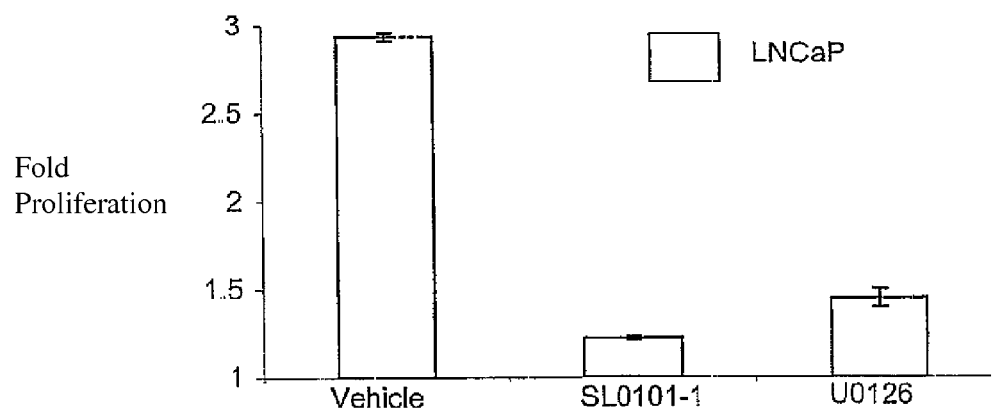
Figure 8C:
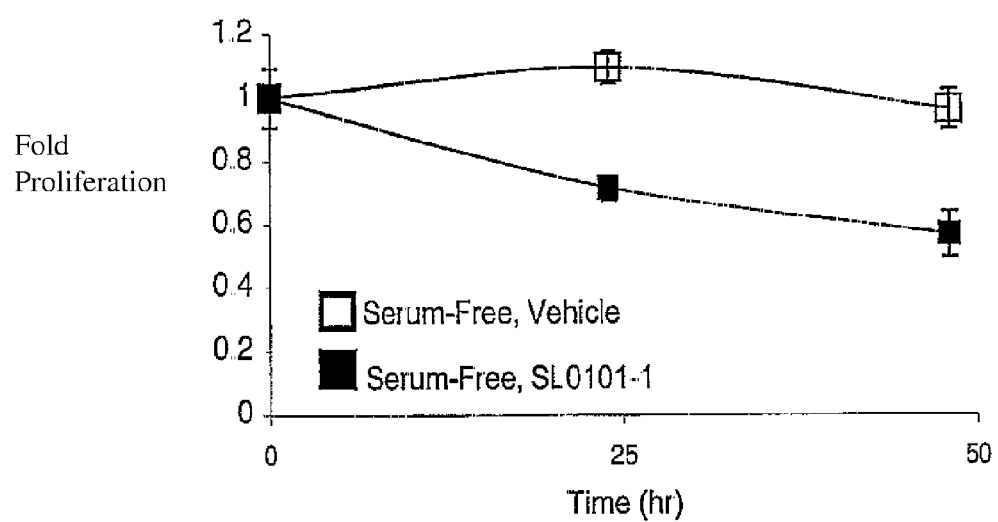
Figure 8D:
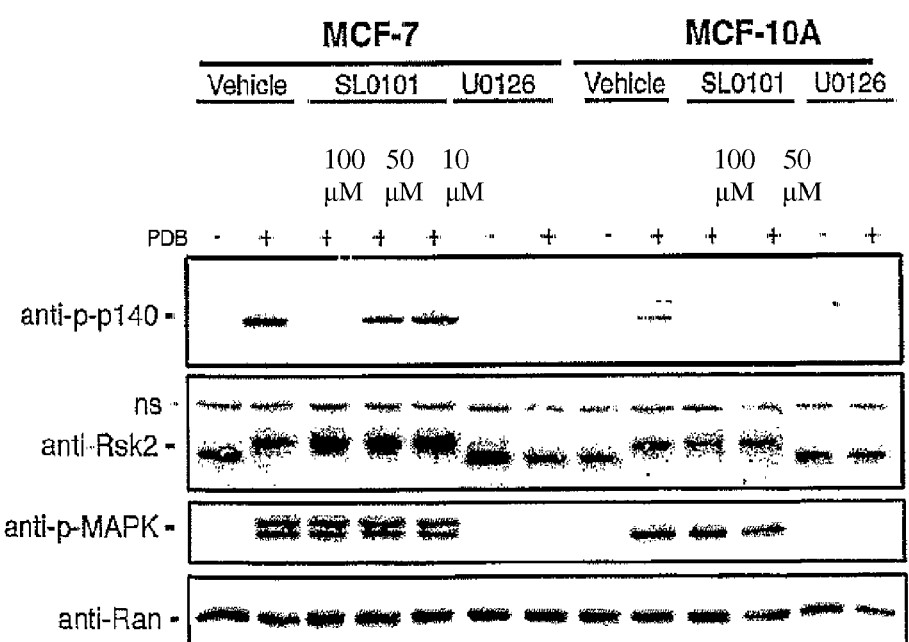

FIGS. 8A-8D SL0101-1 inhibits the proliferation of cancer cells but not normal cells. FIG. 8A demonstrates the results of treating MCF-7 and MCF-10A cells with vehicle or 50 μM SL0101-1 or U0126 (a MEK inhibitor). FIG. 8B demonstrates the results of treating LNCaP cells with vehicle or 50 μM SL0101-1 or 50 μM U0126. FIG. 8C demonstrates the results of treating MCF-7 cells with vehicle or 50 μM SL0101-1 in serum-free medium. FIG. 8D is a Western blot that presents data showing that SL0101-1 does not inhibit kinases of the MAPK pathway upstream of RSK. Cell viability was measured at indicated time points. Proliferation assays were conducted using CellTiter-Glo Luminescent Cell Viability Assay (Promega), performed 44 hrs after treatment for FIGS. 8A & B and at indicated points for FIG. 8C. The data are expressed relative to time 0.

Figure 9:
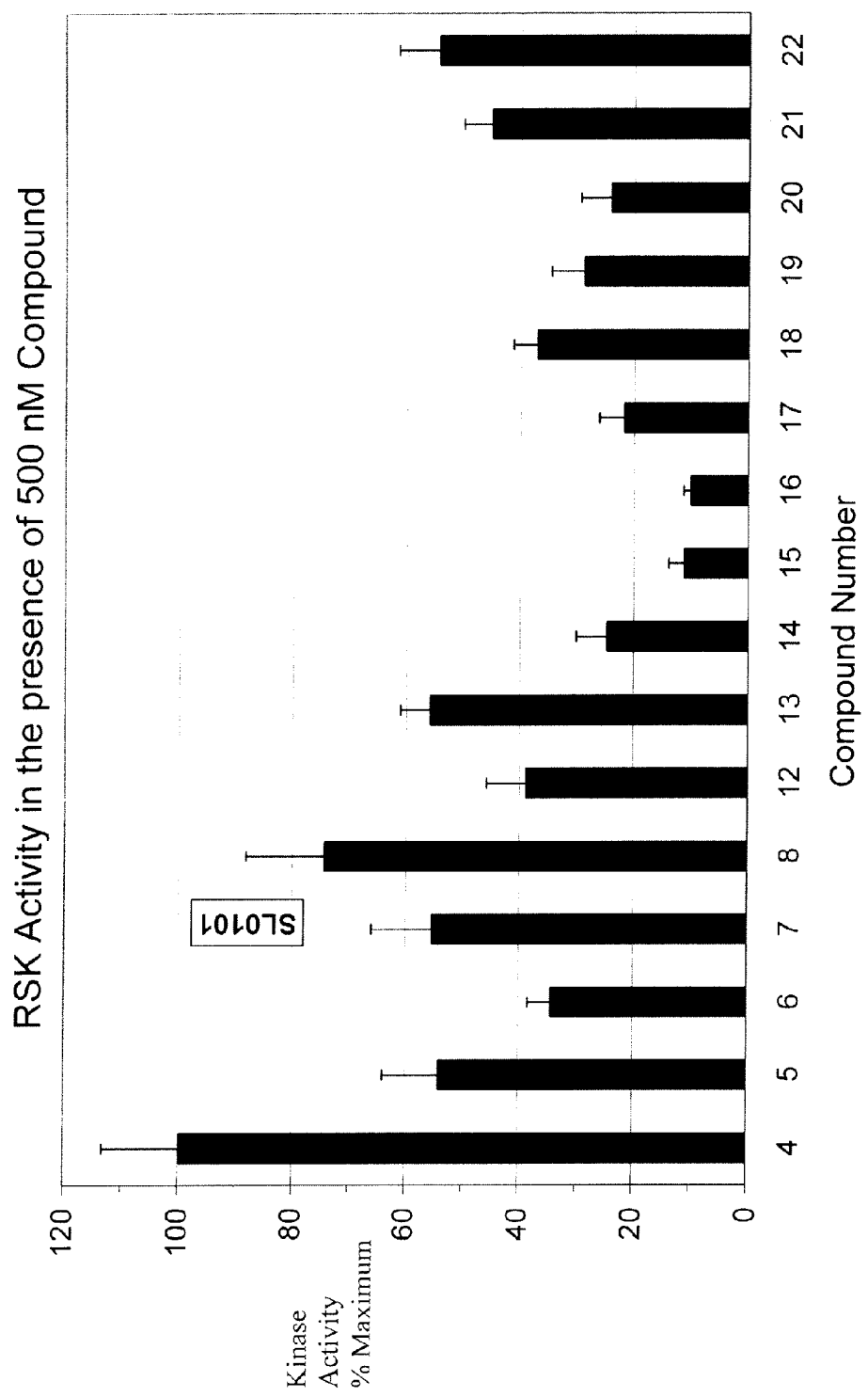

FIG. 9 Inhibition of RSK activity in the presence of 500 nM of SL0101 derivative compounds. 500 nM of the individual inhibitor was added to a RSK kinase mix containing 5 nM of RSK. The reaction was allowed to proceed for 30 mins at room temperature and the data were normalized to the kinase activity obtained in the presence of Kaempferol L-rhamnoside (compound #4). The structure of Kaempferol L-rhamnoside is as follows:

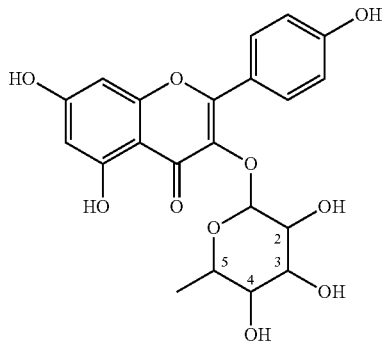 [SMILES: CC1OC(Oc2c(-c3ccc(O)cc3)oc3cc(O)cc(O)c3c2=O)C(O)C(O)C1O]

The compounds tested include Kaempferol L-rhamnoside (4), Kaempferol L-rhamnoside 4"-acetate (5), Kaempferol L-rhamnoside 2",4"-diacetate (6), Kaempferol L-rhamnoside 3",4"-diacetate (7), Kaempferol L-rhamnoside 2",3",4"-triacetate (8), Kaempferol L-carbarhamnoside 4"-acetate (12), Kaempferol L-carbarhamnoside 2",4"-diacetate (13), Kaempferol L-carbarhamnoside 3",4"-diacetate (14), Kaempferol-6"ethyl-L-rhamnoside-2",4"-diacetate (15), Kaempferol-6"ethyl-L-rhamnoside-3",4"-diacetate (16), Kaempferol-6"ethyl-L-rhamnoside (17), Kaempferol-6"ethyl-L-rhamnoside-2",3",4"-triacetate (18), Kaempferol-6"ethyl-L-rhamnoside-2"-monoacetate (19), Kaempferol-6"ethyl-L-rhamnoside-4"-monoacetate (20), Kaempferol-6"methyl-L-rhamnoside (21), Kaempferol-6"isopropyl-L-rhamnoside (22).

Figure 10:
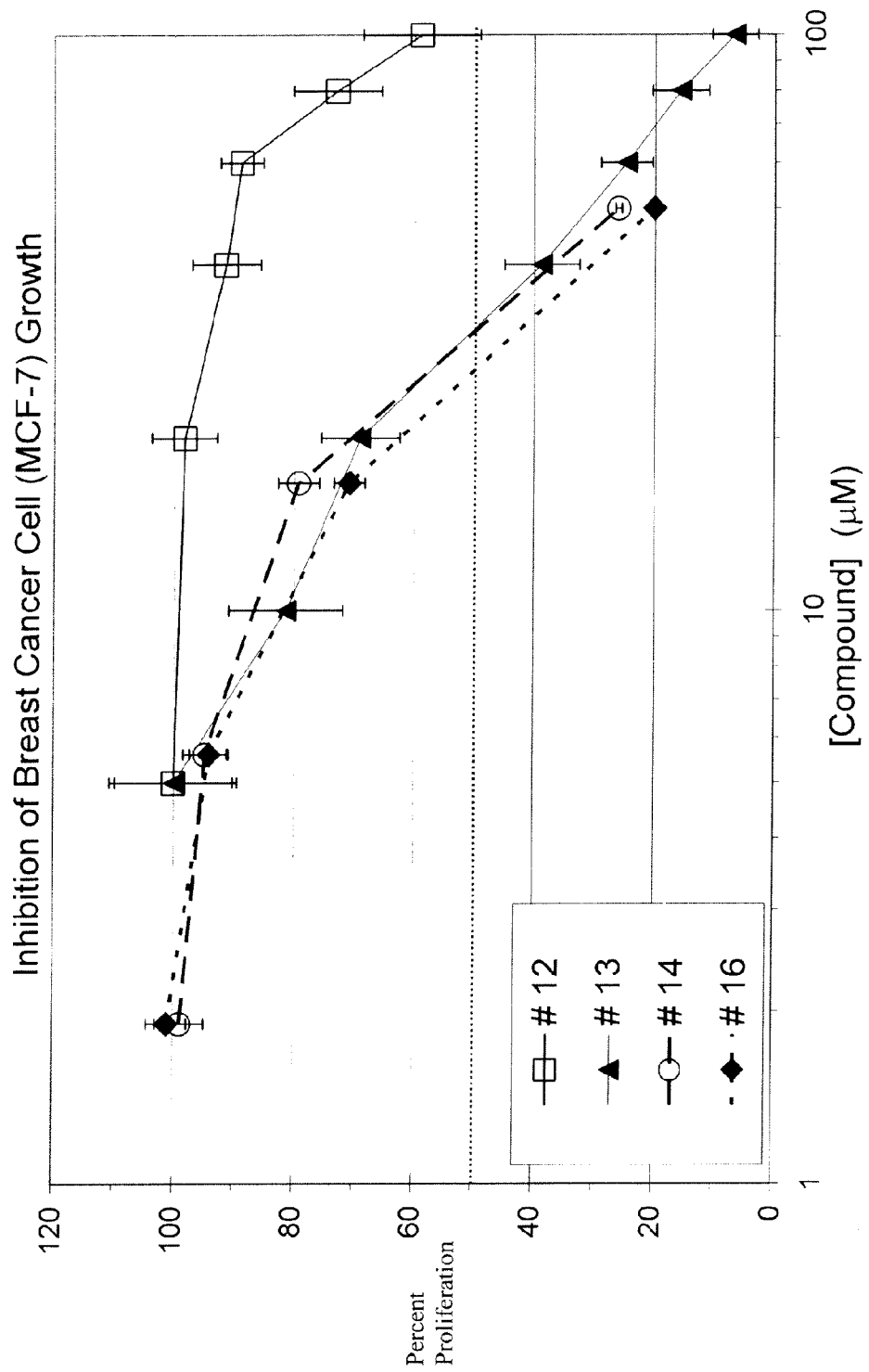

FIG. 10 graphically illustrates the ability of various SL0101 derivative compounds to inhibit MCF-7 breast cancer cell proliferation. Compounds tested include: Kaempferol L-carbarhamnoside 4"-acetate (12), Kaempferol L-carbarhamnoside 2",4"-diacetate (13), Kaempferol L-carbarhamnoside 3",4"-diacetate (14), and Kaempferol-6"ethyl-L-rhamnoside-3",4"-diacetate (16).

Figure 11:
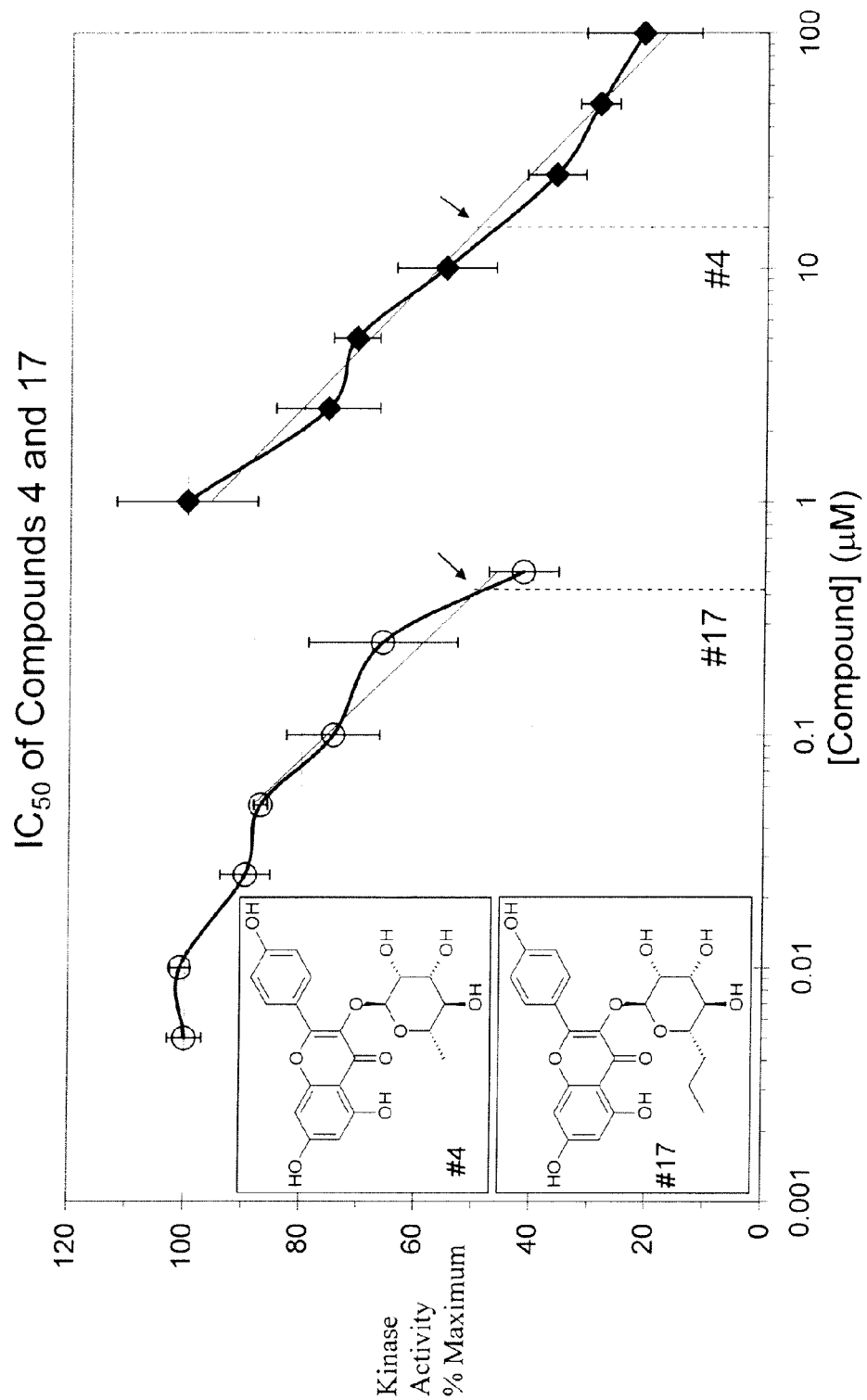

FIG. 11 is a graph providing the $IC_{50}$ of RSK inhibitor compound 4 (Kaempferol Kaempferol L-rhamnoside) and compound 17 (Kaempferol-6"ethyl-L-rhamnoside).

Figure 12:
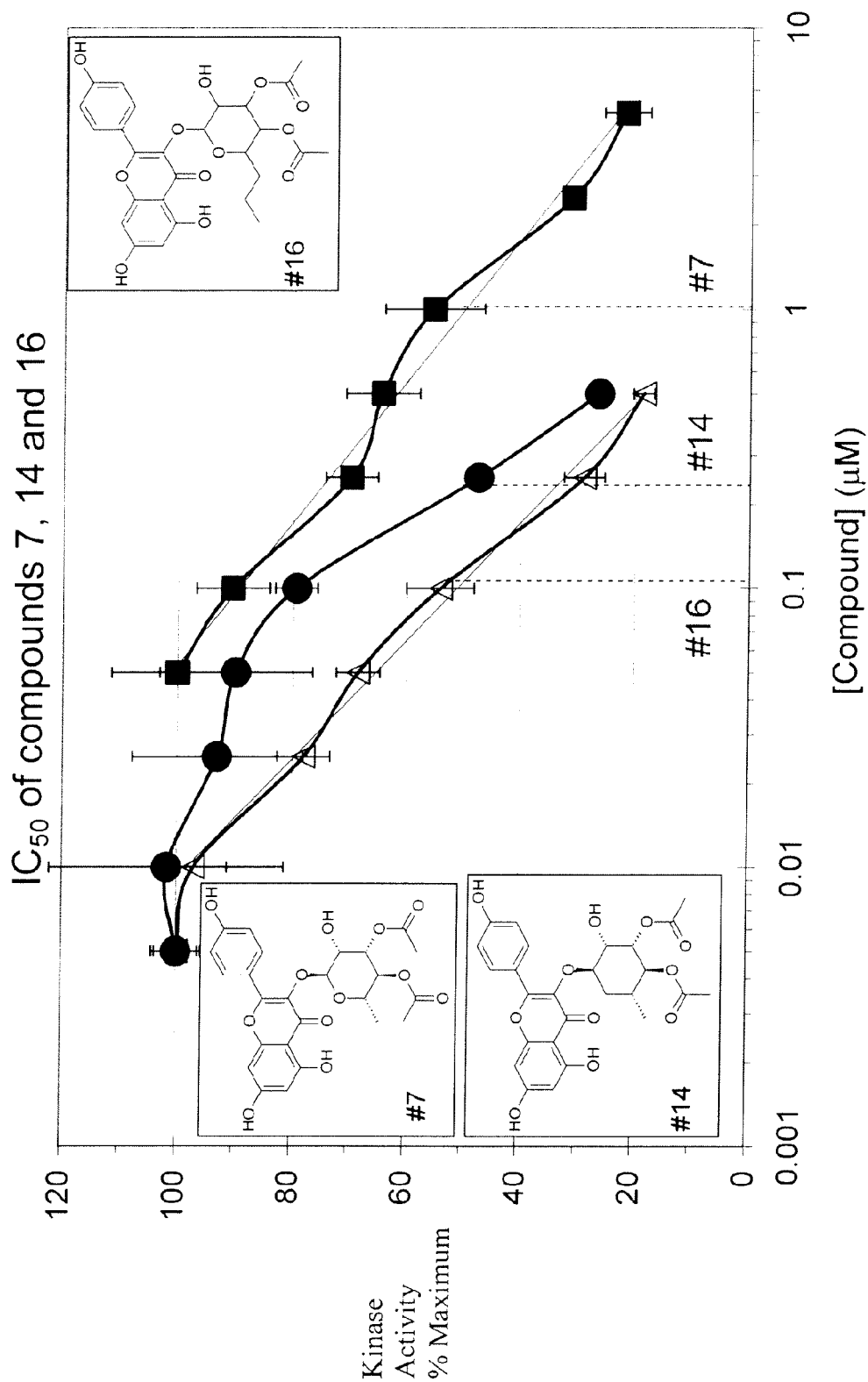

FIG. 12 is a graph providing the $IC_{50}$ of RSK inhibitor compound 7 (SL0101; Kaempferol L-rhamnoside 3",4"-diacetate), compound 14 (Kaempferol L-carbarhamnoside 3",4"-diacetate) and compound 16 (Kaempferol-6"ethyl-L-rhamnoside-3",4"-diacetate).

DETAILED DESCRIPTION

Abbreviations and Acronyms br—broad
CTKD—C-terminal kinase domain
CREB—cyclic adenosine monophosphate response element binding protein
d—doublet
dd—doublet of doublets
DTT—dithiothreitol
eEF2—eukaryotic elongation factor 2
EF2K—EF2 kinase
GST—Glutathione-5-transferase
MAPK—mitogen-activated protein kinase
m—multiplet
NTKD—N-terminal kinase domain
PDB—phorbol dibutyrate
PKA—protein kinase A
PKC—protein kinase C
q—quartet
RSK—a 90 kDa ribosomal S6 kinase, also referred to as p90RSK herein
s—singlet
t—triplet

DEFINITIONS

In describing and claiming the invention, the following terminology will be used in accordance with the definitions set forth below. Unless defined otherwise, all technical and scientific terms used herein have the same meaning as commonly understood by one of ordinary skill in the art to which this invention belongs.

A "bioactive polypeptide" refers to polypeptides which are capable of exerting a biological effect in vitro and/or in vivo.

As used herein, an antimicrobial is a substance that kills, or inhibits the growth or the ability of a microbe (such as bacteria, fungi, or viruses) to infect or maintain an infection in its host cell/organism.

As used herein, the term "pharmaceutically acceptable carrier" includes any of the standard pharmaceutical carriers, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

As used herein the term "pharmaceutically acceptable salt" refers to salts of compounds that retain the biological activity of the parent compound, and which are not biologically or otherwise undesirable. Many of the compounds disclosed herein are capable of forming acid and/or base salts by virtue of the presence of amino and/or carboxyl groups or groups similar thereto.

As used herein, the term "treating" includes prophylaxis of the specific disorder or condition, or alleviation of the symptoms associated with a specific disorder or condition and/or preventing or eliminating said symptoms. For example, as used herein the term "treating an infection" will refer in general to decreasing the number of infectious agents present in a tissue or cell relative to a pretreatment status or relative to an untreated control infected with the relevant pathogen.

As used herein an "effective" amount or a "therapeutically effective amount" of a prodrug refers to a nontoxic but sufficient amount of a bioactive agent to provide the desired effect. For example, an effective amount of an RSK inhibitor is an amount of the inhibitor sufficient to, inter alia, suppress RSK activity as indicated in a serine/threonine kinase assay. The term "effective amount" is used interchangeably with "effective concentration" herein. The amount that is "effective" will vary from subject to subject, depending on the age and general condition of the individual, mode of administration, and the like. Thus, it is not always possible to specify an exact "effective amount." However, an appropriate "effective" amount in any individual case may be determined by one of ordinary skill in the art using routine experimentation.

The term, "parenteral" means not through the alimentary canal but by some other route such as subcutaneous, intramuscular, intraspinal, or intravenous.

The term "about," as used herein, means approximately, in the region of, roughly, or around. When the term "about" is used in conjunction with a numerical range, it modifies that range by extending the boundaries above and below the numerical values set forth. For example, in one aspect, the term "about" is used herein to modify a numerical value above and below the stated value by a variance of 20%.

As used herein, the term "affected cell" refers to a cell of a subject afflicted with a disease or disorder, which affected cell has an altered phenotype relative to a subject not afflicted with a disease or disorder.

Cells or tissue are "affected" by a disease or disorder if the cells or tissue have an altered phenotype relative to the same cells or tissue in a subject not afflicted with a disease or disorder.

As used herein, an "agonist" is a composition of matter which, when administered to a mammal such as a human, enhances or extends a biological activity attributable to the level or presence of a target compound or molecule of interest in the mammal.

An "antagonist" is a composition of matter which when administered to a mammal such as a human, inhibits a biological activity attributable to the level or presence of a compound or molecule of interest in the mammal.

A disease or disorder is "alleviated" if the severity of a symptom of the disease or disorder, the frequency with which such a symptom is experienced by a patient, or both, are reduced.

As used herein, "amino acids" are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include compounds having the following general structure:

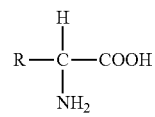

wherein R represents hydrogen or a hydrocarbon side chain, and includes both natural and synthetic amino acids, and both D and L amino acids. "Standard amino acid" means any of the twenty standard L-amino acids commonly found in naturally occurring peptides. "Nonstandard amino acid residue" means any amino acid, other than the standard amino acids, regardless of whether it is prepared synthetically or derived from a natural source. As used herein, "synthetic amino acid" also encompasses chemically modified amino acids, including but not limited to salts, amino acid derivatives (such as amides), and substitutions. Amino acids contained within the peptides of the present invention, and particularly at the carboxy- or amino-terminus, can be modified by methylation, amidation, acetylation or substitution with other chemical groups which can change the peptide's circulating half-life without adversely affecting their activity. Additionally, a disulfide linkage may be present or absent in the peptides of the invention.

The term "amino acid" is used interchangeably with "amino acid residue," and may refer to a free amino acid and to an amino acid residue of a peptide. It will be apparent from the context in which the term is used whether it refers to a free amino acid or a residue of a peptide.

As used herein, an "analog" of a chemical compound is a compound that, by way of example, resembles another in structure but is not necessarily an isomer (e.g., 5-fluorouracil is an analog of thymine).

The term "biological sample," as used herein, refers to samples obtained from a subject, including, but not limited to, skin, hair, tissue, blood, plasma, cells, sweat and urine.

As used herein, a "derivative" of a compound refers to a chemical compound that may be produced from another compound of similar structure in one or more steps, including for example, the replacement of hydrogen by an alkyl, acyl, or amino group.

The use of the word "detect" and its grammatical variants is meant to refer to measurement of the species without quantification, whereas use of the word "determine" or "measure" with their grammatical variants are meant to refer to measurement of the species with quantification. The terms "detect" and "identify" are used interchangeably herein.

As used herein, a "detectable marker" or a "reporter molecule" is an atom or a molecule that permits the specific detection of a compound comprising the marker in the presence of similar compounds without a marker. Detectable markers or reporter molecules include, e.g., radioactive isotopes, antigenic determinants, enzymes, nucleic acids available for hybridization, chromophores, fluorophores, chemiluminescent molecules, electrochemically detectable molecules, and molecules that provide for altered fluorescence-polarization or altered light-scattering.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "excessive RSK activity", as used herein, refers to an increase in RSK activity in a cell with a disease or disorder, relative to the amount of such RSK activity in an otherwise identical normal cell.

As used herein, the term "flavonoid" refers to polyphenolic compounds possessing a carbon skeleton having the general structure:

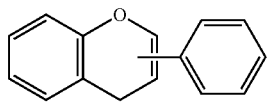

The terms "formula" and "structure" are used interchangeably herein.

As used herein, a "functional" molecule is a molecule in a form in which it exhibits a property by which it is characterized. By way of example, a functional enzyme is one which exhibits the characteristic catalytic activity by which the enzyme is characterized.

Any reference to a compound having a "greater uptake" into a cell relative to another compound (e.g., SL0101) is intended to portray that a higher concentration of the first compound relative to the second will be present in otherwise identical cells that are exposed to the respective compounds for the same length of time. Accordingly, the first compound either has the ability to enter a cell at a greater rate than the second compound or that the first compound has lower rate of degradation or a lower rate of efflux from the cell relative to the second compound.

The term "inhibit," as used herein, refers to the ability of a compound of the invention to reduce or impede a described function. In one embodiment, inhibition is at least 10%, at least 25%, at least 50%, at least 75% of the activity obtained in the absence of the inhibiting agent.

The phrase "inhibit infection", as used herein, refers to both direct and indirect inhibition of infection, regardless of the mechanism.

The term "inhibit a protein", as used herein, refers to any method or technique which inhibits protein synthesis, levels, activity, or function, as well as methods of inhibiting the induction or stimulation of synthesis, levels, activity, or function of the protein of interest. The term also refers to any metabolic or regulatory pathway which can regulate the synthesis, levels, activity, or function of the protein of interest. The term includes binding with other molecules and complex formation. Therefore, the term "protein inhibitor" refers to any agent or compound, the application of which results in the inhibition of protein function or protein pathway function. However, the term does not imply that each and every one of these functions must be inhibited at the same time.

As used herein, "inhibiting RSK" refers to the use of any compound, agent, or mechanism to inhibit RSK synthesis, levels, activity, or function are reduced or inhibited as described above.

As used herein, an "instructional material" includes a publication, a recording, a diagram, or any other medium of expression which can be used to communicate the usefulness of the peptide of the invention in the kit for effecting alleviation of the various diseases or disorders recited herein. Optionally, or alternately, the instructional material may describe one or more methods of alleviating the diseases or disorders in a cell or a tissue of a mammal.

As used herein, "modification" of a compound refers to a compound that's structure or composition has been somewhat changed from the original compound.

As used herein, "pharmaceutical compositions" includes formulations for human and veterinary use.

The term "protein regulatory pathway", as used herein, refers to both the upstream regulatory pathway which regulates a protein, as well as the downstream events which that protein regulates. Such regulation includes, but is not limited to, transcription, translation, levels, activity, posttranslational modification, and function of the protein of interest, as well as the downstream events which the protein regulates.

The terms "protein pathway" and "protein regulatory pathway" are used interchangeably herein.

As used herein, the term "purified" and the like terms relate to the isolation of a molecule or compound in a form that is substantially free (at least 60% free, 75% free, or 90% free) from other components normally associated with the molecule or compound in a native environment.

The term "regulate" refers to either stimulating or inhibiting a function or activity of interest.

As used herein, the use of the term "RSK" is intended to refer generically to all the human RSK isotypes, including RSK1, RSK2, RSK3, and RSK4. RSK1, RSK2, RSK3, and RSK4 are specific human isotypes that have previously been described in the literature.

The term "RSK activity", as used herein, includes synthesis, levels, activity, or function of RSK.

As used herein, the term "RSK inhibitor" includes any compound or condition that specifically inhibits or reduces the kinase activity of RSK or which inhibits any function of RSK. Such inhibitory effects may result from directly, or indirectly, interfering with the protein's ability to phosphorylate its substrate, or may result from inhibiting the expression (transcription and/or translation) of RSK.

The term "standard," as used herein, refers to something used for comparison. For example, it can be a known standard agent or compound which is administered and used for comparing results when administering a test compound, or it can be a standard parameter or function which is measured to obtain a control value when measuring an effect of an agent or compound on a parameter or function. Standard can also refer to an "internal standard", such as an agent or compound which is added at known amounts to a sample and is useful in determining such things as purification or recovery rates when a sample is processed or subjected to purification or extraction procedures before a marker of interest is measured. Internal standards are often a purified marker of interest which has been labeled, such as with a radioactive isotope, allowing it to be distinguished from an endogenous marker.

A "subject" of analysis, diagnosis, or treatment is an animal. Such animals include mammals, preferably a human. The term "host" and "subject" are used interchangeably herein.

As used herein the term "patient" without further designation is intended to encompass any warm blooded vertebrate domesticated animal (including for example, but not limited to livestock, horses, cats, dogs and other pets) and humans.

A "prophylactic" treatment is a treatment administered to a subject, who either does not exhibit signs of a disease or exhibits only early signs of the disease, for the purpose of decreasing the risk of developing pathology associated with the disease.

The general chemical terms used in the description of the compounds of the present invention have their usual meanings. For example, the term "alkyl" by itself or as part of another substituent means a straight or branched aliphatic chain having the stated number of carbon atoms.

The term "$C_1$-$C_n$ alkyl" wherein n can be from 1 through 6, as used herein, represents a branched or linear alkyl group having from one to the specified number of carbon atoms. Typical $C_1$-$C_6$ alkyl groups include, but are not limited to, methyl, ethyl, n-propyl, iso-propyl, butyl, iso-butyl, sec-butyl, tert-butyl, pentyl, hexyl and the like.

The terms "$C_2$-$C_n$ alkenyl" wherein n can be from 2 through 6, as used herein, represents an olefinically unsaturated branched or linear group having from 2 to the specified number of carbon atoms and at least one double bond. Examples of such groups include, but are not limited to, 1-propenyl, 2-propenyl (—$CH_2$—CH=$CH_2$), 1,3-butadienyl, (—CH=CHCH=$CH_2$), 1-butenyl (—CH=CHCH$_2$CH$_3$), hexenyl, pentenyl, and the like.

The term "$C_2$-$C_n$ alkynyl" wherein n can be from 2 to 6, refers to an unsaturated branched or linear group having from 2 to n carbon atoms and at least one triple bond. Examples of such groups include, but are not limited to, 1-propynyl, 2-propynyl, 1-butynyl, 2-butynyl, 1-pentynyl, and the like.

As used herein the term "aryl" refers to a mono- or bicyclic carbocyclic ring system having one or two aromatic rings including, but not limited to, phenyl, naphthyl, tetrahydronaphthyl, indanyl, indenyl, and the like. The size of the aryl ring and the presence of substituents or linking groups are indicated by designating the number of carbons present. For example, the term "($C_1$-$C_3$ alkyl)($C_6$-$C_{10}$ aryl)" refers to a 5 to 10 membered aryl that is attached to a parent moiety via a one to three membered alkyl chain.

The term "heteroaryl" as used herein refers to a mono- or bi-cyclic ring system containing one or two aromatic rings and containing at least one nitrogen, oxygen, or sulfur atom in an aromatic ring. The size of the heteroaryl ring and the presence of substituents or linking groups are indicated by designating the number of carbons present. For example, the term "($C_1$-$C_3$ alkyl)($C_5$-$C_6$ heteroaryl)" refers to a 5 or 6 membered heteroaryl that is attached to a parent moiety via a one to "n" membered alkyl chain.

The term "acyl" refers to alkylcarbonyl species and includes any group or radical of the form RCO— where R is an organic group. The term "acyl" further comprises an organic radical derived from an organic acid by removal of the hydroxyl group from the carboxyl group. The terms "acyl" and "OAc" are used interchangeably herein. The term "acylation" refers to the process of adding an acyl group to a compound.

The term butyryl as used herein encompasses its usual meaning in the art.

The term "halo" includes bromo, chloro, fluoro, and iodo.

The term "haloalkyl" as used herein refers to a alkyl radical bearing at least one halogen substituent, for example, chloromethyl, fluoroethyl or trifluoromethyl and the like.

The term "$C_3$-$C_n$ cycloalkyl" wherein n=3-8, represents the compounds cyclopropyl, cyclobutyl, cyclopentyl, cyclohexyl, cycloheptyl, and cyclooctyl.

The term "heterocyclic group" refers to a $C_3$-$C_8$ cycloalkyl group containing from one to three heteroatoms wherein the heteroatoms are selected from the group consisting of oxygen, sulfur, and nitrogen.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term "lower alkyl" as used herein refers to branched or straight chain alkyl groups comprising one to eight carbon atoms, including methyl, ethyl, propyl, isopropyl, n-butyl, t-butyl, neopentyl and the like.

The term "heteroatom" means for example oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The compounds of the present invention can contain one or more asymmetric centers in the molecule. In accordance with the present invention any structure that does not designate the stereochemistry is to be understood as embracing all the various optical isomers, as well as racemic mixtures thereof. The present invention includes within its scope all such isomers and mixtures thereof.

The compounds of the present invention may exist in tautomeric forms and the invention includes both mixtures and separate individual tautomers. For example, the following structure:

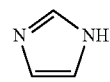

is understood to represent a mixture of the structures:

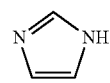

as well as

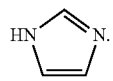

As used herein the term "carbarhamnoside" is intended to refer to a rhamnoside wherein the ring oxygen has been replaced with a carbon.

EMBODIMENTS

As disclosed herein a novel set of p90 Ribosomal S6 Kinase (RSK) inhibitors is described for use in treating diseases or conditions that are associated with excessive or undesired RSK activity. The compounds disclosed herein are novel derivatives of the RSK specific inhibitor, kaempferol 3-O-(3",4"-di-O-acetyl-.alpha.-L-rhamnopyranoside), referred to herein as SL0101. Surprisingly, applicants have found that modification of the substituents of the rhamnopyranoside moiety produced derivative compounds with superior RSK inhibitory activity relative to the parent SL0101 compound. Accordingly, these novel SL0101 derivative compounds are anticipated to be useful for any of the prior uses that have been described for the parent SL0101 compound.

In one embodiment a RSK specific inhibitory compound is provided comprising a compound of the general structure:

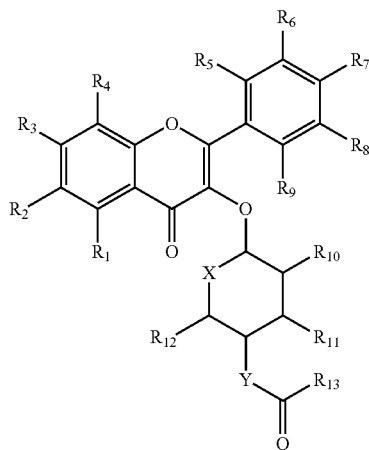

wherein $R_1$, $R_2$, $R_3$, $R_4$, $R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{12}$ is selected from the group consisting of $C_1$-$C_4$ alkyl, $C_1$-$C_4$ alkoxy, and [$C_1$-$C_4$ alkyl]$CH_2R_{18}$;

$R_{13}$ is selected from the group consisting of hydrogen, hydroxyl, and $(CH_2)_m CR_{18}R_{19}(CH_2)_n H$;

m and n are independently an integer from 0-3;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl, $C_1$-$C_4$ alkyl and $C_1$-$C_4$ alkoxy, and $R_{15}$, $R_{18}$ and $R_{19}$ are independently selected from the group consisting of hydrogen and hydroxyl, with the proviso that when X is O, $R_{12}$ is not $CH_3$, and when X is $CH_2$, at least one of $R_{10}$ and $R_{11}$ is hydroxyl.

In one embodiment the RSK inhibitory compound comprises a compound of Formula I wherein $R_2$ and $R_4$ are each hydrogen, $R_1$, $R_3$, and $R_7$ are each hydroxyl, $R_5$, $R_6$, $R_8$ and $R_9$ are independently selected from the group consisting of hydrogen, fluorine, hydroxyl, —$OCOR_{14}$, —$COR_{14}$ and $C_1$-$C_4$ alkoxy, $R_{10}$ and $R_{11}$, are independently selected from the group consisting of hydroxyl, —$OCOR_{14}$ and —$COR_{14}$;

$R_{12}$ is selected from the group consisting of propyl, propyloxy, and —$(CH_2)_2CH_2R_{18}$;

$R_{13}$ is selected from the group consisting of hydrogen, hydroxyl, and —$CR_{18}R_{19}H$;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl and $C_1$-$C_4$ alkoxy, and $R_{15}$, $R_{18}$ and $R_{19}$ are independently selected from the group consisting of hydrogen and hydroxyl. In a further embodiment, Y is O and $R_{13}$ is hydrogen or $CH_3$.

In another further embodiment, $R_{10}$ and $R_{11}$, are independently selected from the group consisting of hydroxyl and —$COCH_3$; $R_{12}$ is propyl or —$(CH_2)_2CH_2R_{18}$; $R_{13}$ is hydrogen or $CH_3$, Y is O; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In an alternative embodiment the RSK inhibitory compound comprises a compound of Formula I wherein X is $CH_2$ or $CF_2$; Y is O; $R_{13}$ is —$CH_2R_{19}$ and at least one of $R_{10}$ and $R_{11}$ is hydroxyl. In a further embodiment, X is $CH_2$ or $CF_2$; Y is O; $R_{10}$ and $R_{11}$, are independently selected from the group consisting of hydroxyl and —$COCH_3$; $R_{12}$ is propyl or —$(CH_2)_2CH_2R_{18}$; $R_{13}$ is —$CH_2R_{19}$; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In accordance with one embodiment a RSK specific inhibitory compound is provided comprising a compound of the general structure of Formula III.

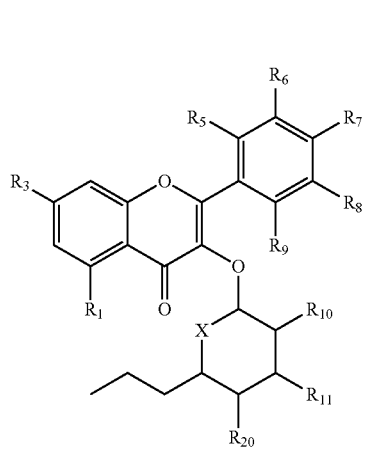

wherein $R_1$ and $R_3$ are independently selected from the group consisting of hydroxyl, —OCOR$_{14}$, —COR$_{14}$, and $C_1$-$C_4$ alkoxy;

$R_5$, $R_6$, $R_7$, $R_8$ and $R_9$ are independently selected from the group consisting of hydrogen, halo, hydroxyl, —OCOR$_{14}$, —COR$_{14}$, $C_1$-$C_4$ alkyl and $C_1$-$C_4$ alkoxy;

$R_{10}$, $R_{11}$ and $R_{20}$ are independently selected from the group consisting of hydroxyl, —NHOCOR$_{14}$, —OCOR$_{14}$, —COR$_{14}$ and $C_1$-$C_4$ alkoxy;

X is selected from the group consisting of O, NH, CH$_2$, and CF$_2$;

Y is selected from the group consisting of O and NR$_{15}$;

$R_{14}$ is selected from the group consisting of hydrogen, and $C_1$-$C_4$ alkyl; and $R_{15}$ is selected from the group consisting of hydrogen, halo, hydroxyl, $C_1$-$C_4$ alkyl and alkoxy.

In one embodiment the RSK inhibitory compound comprises a compound of Formula III wherein X is O or CH$_2$; and $R_{10}$, $R_{11}$ and $R_{20}$ are independently selected from the group consisting of hydroxyl, —NHOCOR$_{14}$, and —COR$_{14}$, wherein at least one of $R_{10}$, $R_{11}$ and $R_{20}$ is hydroxyl. In a further embodiment, $R_5$, $R_6$, $R_8$ and $R_9$ are each hydrogen, $R_1$, $R_3$ and $R_7$ are each hydroxyl, $R_{20}$ is —COCH$_3$, and one of $R_{10}$ and $R_{11}$ is —COCH$_3$ and the other is hydroxyl. In a further embodiment, $R_5$, $R_6$, $R_8$ and $R_9$ are each hydrogen, $R_1$, $R_3$ and $R_7$ are each hydroxyl, and $R_{10}$, $R_{11}$ and $R_{20}$ are independently selected from the group consisting of hydroxyl, —NHOCOR$_{14}$, and —COCH$_3$. In a further embodiment, $R_5$, $R_6$, $R_8$ and $R_9$ are each hydrogen, $R_1$, $R_3$ and $R_7$ are each hydroxyl, and $R_{10}$, $R_{11}$ and $R_{20}$ are independently selected from the group consisting of hydroxyl and —COCH$_3$.

In a further embodiment a RSK specific inhibitory compound is provided comprising a compound of Formula IV:

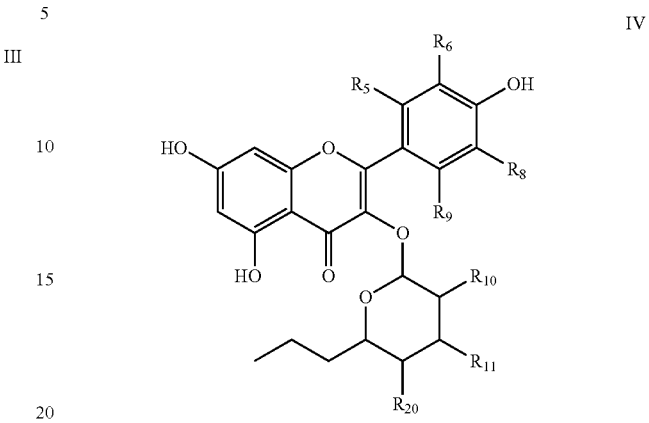

wherein $R_5$, $R_6$, $R_8$ and $R_9$ are independently selected from the group consisting of hydrogen, halo, hydroxyl, —OCOR$_{14}$, —COR$_{14}$, $C_1$-$C_4$ alkyl and $C_1$-$C_4$ alkoxy;

$R_{10}$, $R_{11}$ and $R_{20}$ are independently selected from the group consisting of —COR$_{14}$ and hydroxyl; and $R_{14}$ is selected from the group consisting of hydrogen and $C_1$-$C_4$ alkyl. In one embodiment at least one of $R_{10}$, $R_{11}$ and $R_{20}$ is hydroxyl. In a further embodiment $R_5$, $R_6$, $R_8$ and $R_9$ are each hydrogen and $R_{20}$ is —COCH$_3$ and at least one of $R_{10}$ and $R_{11}$ is hydroxyl. In a further embodiment $R_{20}$ is —COCH$_3$ and one of $R_{10}$ and $R_{11}$ is —COCH$_3$ and the other is hydroxyl.

In one embodiment the RSK specific inhibitor comprises a compound having the structure:

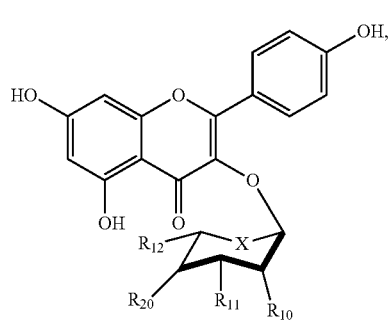

wherein

X is O, CF$_2$ or CH$_2$;

$R_{10}$, $R_{11}$ and $R_{20}$ are independently selected from the group consisting of OH, OCOR$_8$, COR$_E$, NHOCOR$_8$ and $C_1$-$C_4$ alkoxy; and $R_{12}$ is $C_1$-$C_4$ alkyl, with the proviso that when X is O, $R_{12}$ is propyl. In one embodiment, X is O, $R_{12}$ is propyl, at least one of $R_{10}$, $R_{11}$ and $R_{20}$ is —COCH$_3$ and at least one of $R_{10}$, $R_{11}$ and $R_{20}$ is hydroxyl. In a further embodiment X is O, $R_{12}$ is propyl, $R_{20}$ is —COCH$_3$ and one of $R_{10}$ and $R_{11}$ is —COCH$_3$ and the other is hydroxyl.

In an alternative embodiment a compound is provided having the general structure of Formula IV as disclosed above, but having one or more sulfhydryls (—SH) groups substituting at positions on the flavonoid ring that designate a hydroxyl group (e.g., at positions $R_1$, $R_2$, $R_3$, $R_4$, $R_5$, $R_6$ and $R_7$ of the compound of Formula I). In one embodiment a compound is provided having the general structure of Formula IV as disclosed above, wherein one or more sulfhydryls (—SH) groups are present at positions selected from the group consisting of $R_1$, $R_3$ and $R_7$, as designated in the structure of Formula I. In a further alternative embodiment a compound is provided having the general structure of Formula IV as disclosed above, but having one or more acetamide (NHOCCH$_3$) groups substituting at positions on the sugar moiety that designate a hydroxyl group (i.e., at positions $R_{10}$ and $R_{11}$). In one embodiment the acetamide can be a substituted acetamide comprising NHOCOR$_{14}$. In one aspect, the compounds encompassed by Formula IV have greater stability in their interaction with RSK than does SL0101 in its interaction with RSK. In another aspect, the compounds of Formula IV have a greater ability to inhibit RSK than does SL0101.

In accordance with one embodiment, the compounds comprised by Formula IV are modified to replace the hydroxyl groups of the flavonoid with sulfhydryls (—SH). Alternatively, in another embodiment, the compounds comprised by Formula IV are modified to replace the hydroxyl groups of the flavonoid with an acetamide (NHOCR$_{14}$), including for example:

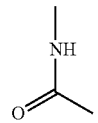

or substituted acetamide such as

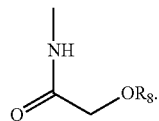

In cases where compounds are sufficiently basic or acidic to form acid or base salts, use of the compounds as salts may be appropriate. Examples of acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

In accordance with one embodiment a pharmaceutical composition is provided comprising the compound of Formula I, II, III, IV or V and a pharmaceutically acceptable carrier. Surprisingly applicants have discovered that the novel SL0101 derivative compounds disclosed herein have improved activity as RSK inhibitors relative to the previously described RSK inhibitor, SL0101 (see FIG. 9). One key difference appears to be the addition of an ethyl group at position 6 of the rhamnoside moiety of the SL0101 parent compound (see structure of Formulas III and IV). In addition to improved inhibitory activity, the SL0101 derivative compounds disclosed herein also display surprisingly improved pharmacokinetic properties (e.g., improved metabolic stability, solubility and membrane permeability), which in turn will make these new compounds better drugs for the treatment of RSK related diseases (e.g., cancer and intracellular pathogenic infections, e.g., *Yersinia* infections).

Use of RSK Inhibitors for the Treatment of Septicemia

The present disclosure provides a method of treating septicemia. Septicemia is characterized by evidence of acute inflammation present throughout the entire body that ultimately results in multiple organ dysfunction. Since the endothelium is both the target for, and the source of, inflammatory mediators, it is a key organ in the development of septicemia. Thus, in accordance with the present disclosure, a therapeutic strategy is provided that is based on the inhibition of RSK activity as a means of limiting the development of systemic inflammation. More particularly, systemic inflammation is controlled by modifying the pattern of inflammatory mediators released upon activation, and/or attenuating the response of the endothelium to the inflammatory mediators.

Upon detection of an invading pathogen, monocytes and macrophages initiate inflammatory cascades resulting in secretion of inflammatory mediators that dramatically alter the function of the endothelial cells. Inhibition of RSK activity has been found by applicants to reduce pathogenic stimulated expression of adhesion factors in endothelial cells and to reduce the pathogenic stimulated expression of nitric oxide synthase by macrophages (see FIGS. 2-3). Accordingly, inhibiting RSK activity provides a means of reducing the systemic inflammatory response associated with septicemia, and thus provide a novel method for preventing dysfunction of the endothelium that results in tissue damage and subsequent multiple organ failure.

In accordance with one embodiment a composition and method are provided for use in reducing the systemic inflammatory response associated with septicemia and thereby preventing or treating septicemia, wherein the composition comprises a RSK inhibiting agent. The RSK specific inhibitors used in accordance with the disclosed methods are selected from any of the novel kaempferol 3-O-(3",4"-di-O-acetyl-α-L-rhamnopyranoside) derivative compounds disclosed herein.

In accordance with one embodiment, a method of reducing pathogenic stimulated expression of adhesion factors in endothelial cells, or reducing the pathogenic stimulated expression of nitric oxide synthase by macrophages, is provided, wherein an RSK inhibitor is administered to an individual in need thereof. In one embodiment the RSK specific inhibitor comprises a compound having the structure of formula I:

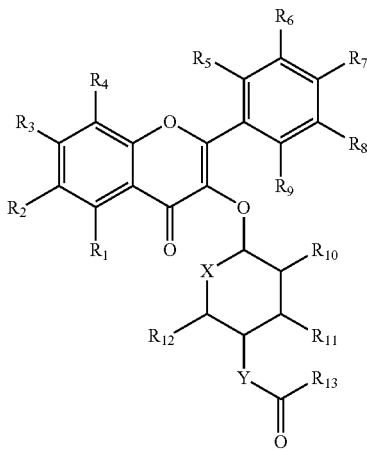

I wherein $R_1$, $R_2$, $R_3$, $R_4$, $R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{12}$ is selected from the group consisting of $C_1$-$C_4$ alkyl, $C_1$-$C_4$ alkoxy, and $[C_1$-$C_4$ alkyl]$CH_2R_{18}$;

$R_{13}$ is selected from the group consisting of hydrogen, hydroxyl, and $(CH_2)_m CR_{18}R_{19}(CH_2)_n H$;

m and n are independently an integer from 0-3;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl, $C_1$-$C_4$ alkyl and $C_1$-$C_4$ alkoxy, and $R_{15}$, $R_{18}$ and $R_{19}$ are independently selected from the group consisting of hydrogen and hydroxyl, with the proviso that when X is O, $R_{12}$ is not $CH_3$, and when X is $CH_2$, at least one of $R_{10}$ and $R_{11}$ is hydroxyl.

In one embodiment the RSK inhibitory compound comprises a compound of Formula I wherein $R_2$ and $R_4$ are each hydrogen, $R_1$, $R_3$, and $R_7$ are each hydroxyl, $R_5$, $R_6$, $R_8$ and $R_9$ are independently selected from the group consisting of hydrogen, fluorine, hydroxyl, —$OCOR_{14}$, —$COR_{14}$ and $C_1$-$C_4$ alkoxy, $R_{10}$ and $R_{11}$, are independently selected from the group consisting of hydroxyl, —$OCOR_{14}$ and —$COR_{14}$;

$R_{12}$ is selected from the group consisting of propyl, propyloxy, and —$(CH_2)_2CH_2R_{18}$;

$R_{13}$ is selected from the group consisting of hydrogen, hydroxyl, and —$CR_{18}R_{19}H$;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl and $C_1$-$C_4$ alkoxy, and $R_{15}$, $R_{18}$ and $R_{19}$ are independently selected from the group consisting of hydrogen and hydroxyl. In a further embodiment, Y is O and $R_{13}$ is hydrogen or $CH_3$. In another further embodiment, $R_{10}$ and $R_{11}$, are independently selected from the group consisting of hydroxyl and —$COCH_3$; $R_{12}$ is propyl or —$(CH_2)_2CH_2R_{18}$; $R_{13}$ is hydrogen or $CH_3$, Y is O; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In an alternative embodiment the RSK inhibitory compound comprises a compound of Formula I wherein X is $CH_2$ or $CF_2$; Y is O; $R_{13}$ is —$CH_2R_{19}$ and at least one of $R_{10}$ and $R_{11}$ is hydroxyl. In a further embodiment, X is $CH_2$ or $CF_2$; Y is O; $R_{10}$ and $R_{11}$, are independently selected from the group consisting of hydroxyl and —$COCH_3$; $R_{12}$ is propyl or —$(CH_2)_2CH_2R_{18}$; $R_{13}$ is —$CH_2R_{19}$; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In accordance with one embodiment the RSK specific inhibitory compound has the structure of Formula II:

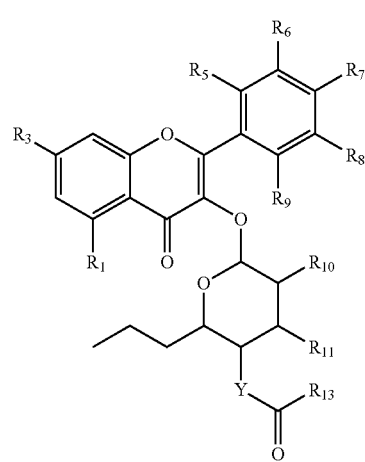

II wherein $R_1$, and $R_3$ are independently selected from the group consisting of hydroxyl, —$OCOR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{13}$ is selected from the group consisting of hydrogen, hydroxyl, and $(CH_2)_m CR_{18}R_{19}(CH_2)_n H$;

m and n are independently an integer from 0-3;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$, $R_{18}$ and $R_{19}$ are independently selected from the group consisting of hydrogen and hydroxyl. In further embodiment, Y is O, $R_{10}$ and $R_{11}$, are independently selected from the group consisting of hydroxyl and —$COCH_3$; $R_{13}$ is hydrogen or $CH_3$. In a further embodiment, $R_2$, $R_4$, $R_5$, $R_6$, $R_8$ and $R_9$ are each hydrogen, $R_1$, $R_3$, and $R_7$ are each hydroxyl.

In accordance with one embodiment a RSK specific inhibitory compound is provided comprising a compound of the general structure of Formula III.

III wherein $R_1$, and $R_3$ are independently selected from the group consisting of hydroxyl, —$OCOR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of hydroxyl, —$NHOCOR_{14}$, —$OCOR_{14}$, —$COR_{14}$ and $C_1$-$C_4$ alkoxy;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$ is selected from the group consisting of hydrogen, halo, hydroxyl, $C_1$-$C_4$ alkyl and $C_1$-$C_4$ alkoxy.

In one embodiment the RSK inhibitory compound comprises a compound of Formula III wherein X is O or $CH_2$; and $R_{10}$, $R_{11}$ and $R_{20}$ are independently selected from the group consisting of hydroxyl, —$NHOCOR_{14}$, and —$COR_{14}$, wherein at least one of $R_{10}$, $R_{11}$ and $R_{20}$ is hydroxyl. In a further embodiment, $R_5$, $R_6$, $R_8$ and $R_9$ are each hydrogen, $R_1$, $R_3$ and $R_7$ are each hydroxyl, $R_{20}$ is —$COCH_3$, and one of $R_{10}$ and $R_{11}$ is —$COCH_3$ and the other is hydroxyl.

In a further embodiment a RSK specific inhibitory compound is provided comprising a compound of Formula IV:

IV wherein $R_5$, $R_6$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of —$COR_{14}$ and hydroxyl, and $R_{14}$ is selected from the group consisting of hydrogen and $C_1$-$C_4$ alkyl. In one embodiment at least one of $R_{10}$, $R_{11}$ and $R_{20}$ is hydroxyl. In a further embodiment $R_5$, $R_6$, $R_8$ and $R_9$ are each hydrogen and $R_{20}$ is —$COCH_3$ and at least one of $R_{10}$ and $R_{11}$ is hydroxyl. In a further embodiment $R_{20}$ is —$COCH_3$ and one of $R_{10}$ and $R_{11}$ is —$COCH_3$ and the other is hydroxyl.

In one embodiment the administered RSK specific inhibitor comprises a compound having the structure of Formula IV, and more particularly the RSK inhibitor has the structure:

wherein $R_{10}$, $R_{11}$ and $R_{20}$ are independently selected from the group consisting of OH, $OCOR_8$, $COR_S$, $NHOCOR_8$ and $C_1$-$C_4$ alkoxy. In one embodiment, at least one of $R_{10}$, $R_{11}$ and $R_{20}$ is —COCH$_3$ and at least one of $R_{10}$, $R_{11}$ and $R_{20}$ is hydroxyl. In a further embodiment $R_{20}$ is —COCH$_3$ and one of $R_{10}$ and $R_{11}$ is —COCH$_3$ and the other is hydroxyl.

Use of RSK Inhibitors as Anti-Infective Agents

Figure 4A:
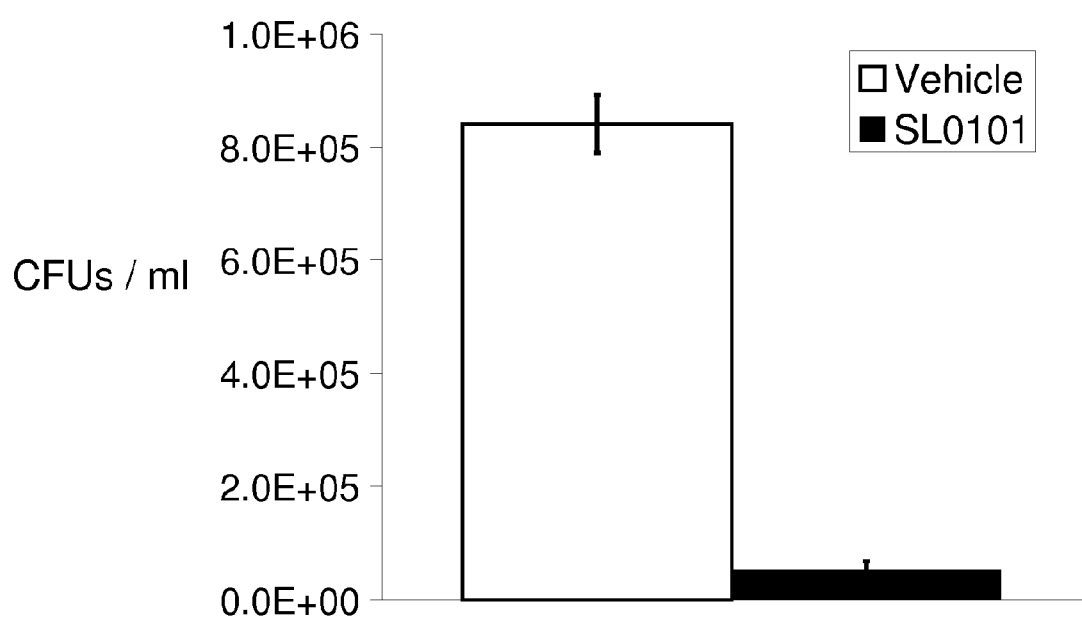
Figure 4B:
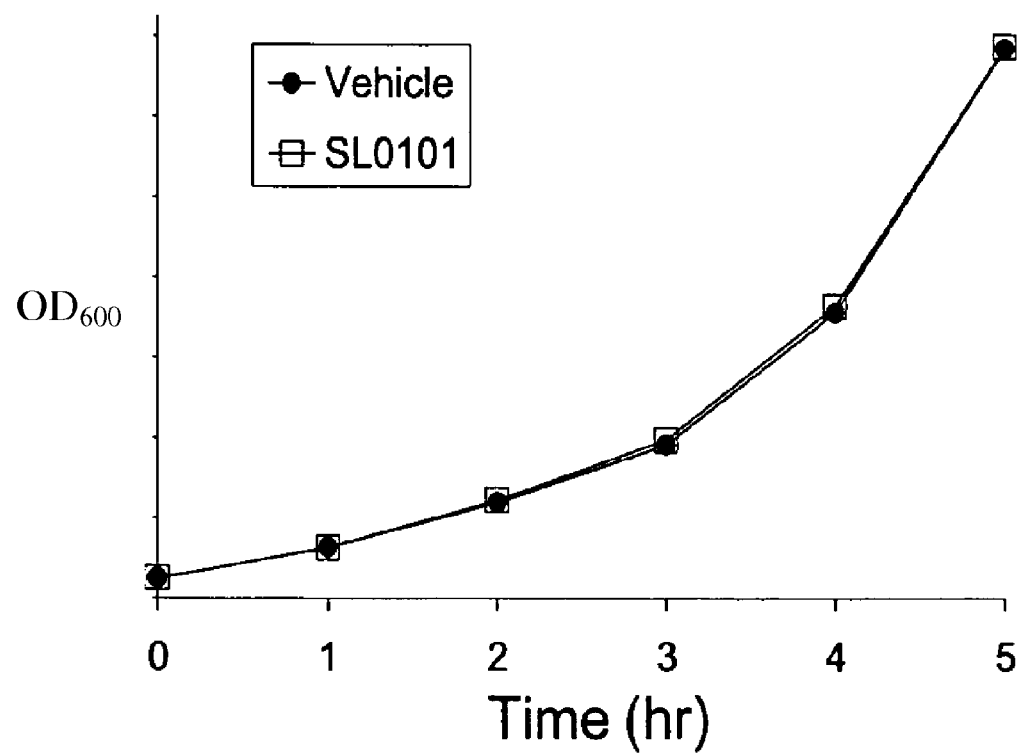

Certain pathogens have developed a mechanism to impede cellular endosome/phagosome maturation as a means of circumventing a host's cells ability to destroy and remove the pathogen from the cell. Applicants have discovered that RSK activity is involved in endosomal/phagosomal maturation and that that pathogenic inhibition of endosome/phagosome maturation requires RSK activity. Accordingly, inhibition of RSK activity as detailed herein has been found to decrease the pathogen's ability to impede endosome/phagosome maturation and can improve the host organism's ability to resist and/or mitigate pathogen infections. More particularly, the present application discloses that an inhibitor of RSK activity protects the host-cell's cytoskeleton from pathogen-induced actin reorganization, and furthermore that a RSK inhibitor reduces the viability of internalized *Y. pseudotuberculosis* (see FIG. 4A) through an indirect mechanism (see FIG. 4B).

In accordance with one embodiment, the present invention provides compositions and methods for inhibiting native RSK activity in the cells of a potential host organism as a means of interfering with the ability of a pathogen to avoid the microbicidal machinery of the host. As a result of the treatment with the RSK inhibitor, the infective capabilities of the pathogenic organism are reduced. Current anti-infective agents target the pathogen with antibiotics or anti-adhesion therapeutics. The class of anti-infective agents disclosed herein target the host cell signaling events required by the pathogen to establish and maintain infection. Thus, the present invention encompasses compositions and methods useful for providing protection by targeting the host rather than the pathogen. In one aspect, the host is a human.

One aspect of the present disclosure encompasses the use of inhibitors of RSK activity, as novel anti-infective agents. More particularly, in one embodiment a composition and method for inhibiting the ability of intracellular pathogens to initiate or maintain an infection is provided, wherein the targeted pathogen has the capacity to impede endosomal/phagosomal maturation. The method comprises administering an anti-infective pharmaceutical composition that comprises an inhibitor of RSK activity and a pharmaceutically acceptable carrier. In one embodiment the RSK inhibiting flavonoid-like compound comprises a compound of the general structure of Formula I:

wherein $R_1$, $R_2$, $R_3$, $R_4$, $R_5$, $R_6$, $R_7$, $R_8$ and $R_9$ are independently selected from the group consisting of hydrogen, halo, hydroxyl, —OCOR$_{14}$, —COR$_{14}$, $C_1$-$C_4$ alkyl and $C_1$-$C_4$ alkoxy;

$R_{10}$ and $R_{11}$, are independently selected from the group consisting of hydrogen, halo, hydroxyl, —NHOCOR$_{14}$, —OCOR$_{14}$, —COR$_{14}$ and $C_1$-$C_4$ alkoxy;

$R_{12}$ is selected from the group consisting of $C_2$-$C_4$ alkyl, $C_1$-$C_4$ alkoxy, and [$C_1$-$C_4$ alkyl]CH$_2$R$_{18}$;

$R_{13}$ is selected from the group consisting of hydrogen, hydroxyl, and (CH$_2$)$_m$CR$_{18}$R$_{19}$(CH$_2$)$_n$H;

m and n are independently an integer from 0-3;

X is selected from the group consisting of O, CH$_2$, and CF$_2$;

Y is selected from the group consisting of O, NR$_{15}$, and CR$_{16}$R$_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl, $C_1$-$C_4$ alkyl and $C_1$-$C_4$ alkoxy, and $R_{15}$, $R_{18}$ and $R_{19}$ are independently selected from the group consisting of hydrogen and hydroxyl.

In one embodiment the RSK inhibitory compound comprises a compound of Formula I wherein $R_2$ and $R_4$ are each hydrogen, $R_1$, $R_3$, and $R_7$ are each hydroxyl, $R_5$, $R_6$, $R_8$ and $R_9$ are independently selected from the group consisting of hydrogen, fluorine, hydroxyl, —OCOR$_{14}$, —COR$_{14}$ and $C_1$-$C_4$ alkoxy, $R_{10}$ and $R_{11}$, are independently selected from the group consisting of hydrogen, hydroxyl, —OCOR$_{14}$, and —COR$_{14}$;

$R_{12}$ is selected from the group consisting of propyl, propyloxy, and —(CH$_2$)$_2$CH$_2$R$_{18}$;

$R_{13}$ is selected from the group consisting of hydrogen, hydroxyl, and —CR$_{18}$R$_{19}$H;

X is selected from the group consisting of O, CH$_2$, and CF$_2$;

Y is selected from the group consisting of O, NR$_{15}$, and CR$_{16}$R$_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl and $C_1$-$C_4$ alkoxy, and $R_{15}$, $R_{18}$ and $R_{19}$ are independently selected from the group consisting of hydrogen and hydroxyl. In a further embodiment, Y is O and $R_{13}$ is hydrogen or CH$_3$. In another further embodiment, $R_{10}$ and $R_{11}$, are independently selected from the group consisting of hydroxyl and —COCH$_3$; $R_{12}$ is propyl or —(CH$_2$)$_2$CH$_2$R$_{18}$; $R_{13}$ is hydrogen or CH$_3$, Y is O; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In an alternative embodiment the RSK inhibitory compound comprises a compound of Formula I wherein X is CH$_2$ or CF$_2$; Y is O; $R_{13}$ is —CH$_2$R$_{19}$ and at least one of $R_{10}$ and $R_{11}$ is hydroxyl. In a further embodiment, X is CH$_2$ or CF$_2$; Y is O; $R_{10}$ and $R_{11}$, are independently selected from the group consisting of hydroxyl and —COCH$_3$; $R_{12}$ is propyl or —(CH$_2$)$_2$CH$_2$R$_{18}$; $R_{13}$ is —CH$_2$R$_{19}$; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In accordance with one embodiment the RSK specific inhibitory compound has the structure of Formula II:

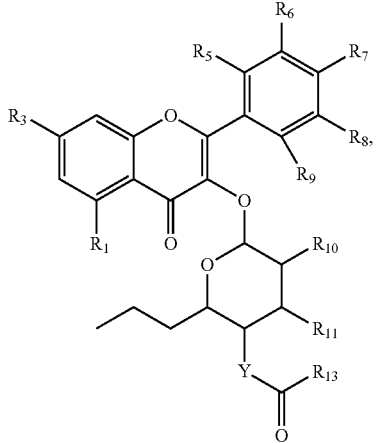

II wherein $R_1$, and $R_3$ are independently selected from the group consisting of hydroxyl, —$OCOR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{13}$ is selected from the group consisting of hydrogen, hydroxyl, and $(CH_2)_m CR_{18}R_{19}(CH_2)_n H$;

m and n are independently an integer from 0-3;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$, $R_{18}$ and $R_{19}$ are independently selected from the group consisting of hydrogen and hydroxyl. In further embodiment, Y is O, $R_{10}$ and $R_{11}$, are independently selected from the group consisting of hydroxyl and —$COCH_3$; $R_{13}$ is hydrogen or $CH_3$. In a further embodiment, $R_2$, $R_4$, $R_5$, $R_6$, $R_8$ and $R_9$ are each hydrogen, $R_1$, $R_3$, and $R_7$ are each hydroxyl.

In accordance with one embodiment a RSK specific inhibitory compound is provided comprising a compound of the general structure of Formula III.

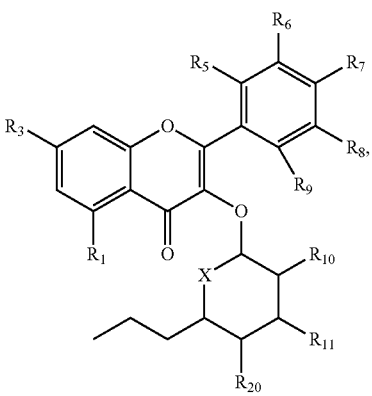

III wherein $R_1$, and $R_3$ are independently selected from the group consisting of hydroxyl, —$OCOR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of hydroxyl, —$NHOCOR_{14}$, —$OCOR_{14}$, —$COR_{14}$ and $C_1$-$C_4$ alkoxy;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$ is selected from the group consisting of hydrogen, halo, hydroxyl, $C_1$-$C_4$ alkyl and $C_1$-$C_4$ alkoxy.

In one embodiment the RSK inhibitory compound comprises a compound of Formula III wherein X is O or $CH_2$; and $R_{10}$, $R_{11}$ and $R_{20}$ are independently selected from the group consisting of hydroxyl, —$NHOCOR_{14}$, and —$COR_{14}$, wherein at least one of $R_{10}$, $R_{11}$ and $R_{20}$ is hydroxyl. In a further embodiment, $R_5$, $R_6$, $R_8$ and $R_9$ are each hydrogen, $R_1$, $R_3$ and $R_7$ are each hydroxyl, $R_{20}$ is —$COCH_3$, and one of $R_{10}$ and $R_{11}$ is —$COCH_3$ and the other is hydroxyl.

In a further embodiment a RSK specific inhibitory compound is provided comprising a compound of Formula IV:

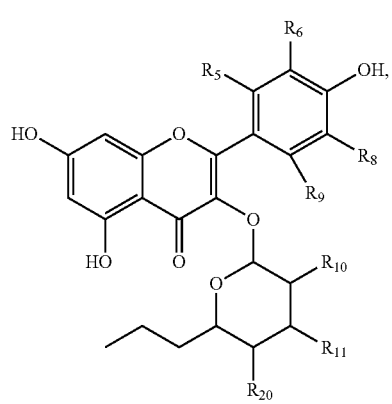

IV wherein $R_5$, $R_6$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of —$COR_{14}$ and hydroxyl, and $R_{14}$ is selected from the group consisting of hydrogen and $C_1$-$C_4$ alkyl. In one embodiment at least one of $R_{10}$, $R_{11}$ and $R_{20}$ is hydroxyl. In a further embodiment $R_5$, $R_6$, $R_8$ and $R_9$ are each hydrogen and $R_{20}$ is —$COCH_3$ and at least one of $R_{10}$ and $R_{11}$ is hydroxyl. In a further embodiment $R_{20}$ is —$COCH_3$ and one of $R_{10}$ and $R_{11}$ is —$COCH_3$ and the other is hydroxyl.

In one embodiment the administered RSK specific inhibitor comprises a compound having the structure of Formula IV, and more particularly the RSK inhibitor has the structure:

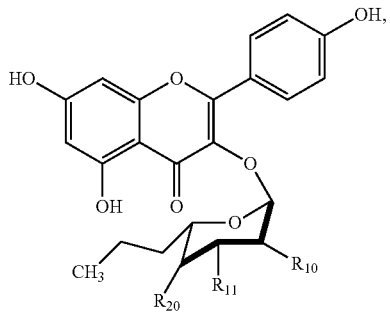

wherein $R_{10}$, $R_{11}$ and $R_{20}$ are independently selected from the group consisting of OH, $OCOR_8$, $COR_8$, $NHOCOR_8$ and $C_1$-$C_4$ alkoxy. In one embodiment, at least one of $R_{10}$, $R_{11}$ and $R_{20}$ is —$COCH_3$ and at least one of $R_{10}$, $R_{11}$ and $R_{20}$ is hydroxyl. In a further embodiment $R_{20}$ is —$COCH_3$ and one of $R_{10}$ and $R_{11}$ is —$COCH_3$ and the other is hydroxyl.

The RSK inhibitory compounds can be formulated into pharmaceutical compositions by combining them with an appropriate pharmaceutically acceptable carrier using standard techniques known to those skilled in the art. The compositions may further comprise additional anti-microbial and antibacterial components. Anti-microbial agents suitable for use in accordance with the present invention are known to those skilled in the art and include antibiotics, both natural and synthetic derivatives as well as other compounds known to have anti-microbial activity (see for example U.S. Pat. No. 7,358,359, the disclosure of which is incorporated herein by reference). In accordance with one embodiment a pharmaceutically acceptable anti-microbial agent is combined with a RSK inhibitor to treat an established infection by an intercellular pathogen or to treat a patient prophylactically to prevent the establishment of an infection by an intercellular pathogen. The combination therapy can be administered simultaneously by administering a single composition comprising a known anti-microbial agent and a RSK inhibitor or the anti-microbial agent can be administered prior to or after the administration of the RSK inhibitor. Typically the antimicrobial agent is administered within 24 hours before or after the administration of the RSK inhibitor and in one embodiment the two agents are each administered within 12 hours, 8 hours, 4 hours, 2 hours or 1 hour of each other.

Although not wishing to be bound by any particular theory, the results disclosed herein suggest that by targeting RSK, a new class of anti-infective agents can provide broad-spectrum protection from numerous intracellular pathogens that impede endosomal/phagosomal maturation. See Table 1 in Example 8 for a list of exemplary pathogens and the pathology resulting from infection from the listed pathogens.

Use of RSK Inhibitors as Anti-Cancer Agents

Inhibition of RSK by the present compounds has been discovered to halt the proliferation of cancer cell lines while having little effect on the proliferation rate of normal cells. In accordance with one embodiment a method of inhibiting the proliferation of cancer cells is provided wherein the method comprises the steps of administering a compound of the general structure of Formula I, II, III, IV or V. In one embodiment the composition comprises compounds of the general structure of Formula IV are administered to inhibit the proliferation of neoplastic cells and to treat cancer.

In another embodiment, the RSK inhibitory SL0101 analogs can be used in a novel method of inhibiting endothelial cell migration. Inhibition of endothelial cell migration inhibits the ability of endothelial cells to conduct the initial steps needed for angiogenesis, leading to alleviation of the symptoms and restoration of the health of patients suffering from diseases associated with inappropriate angiogenic activity. Accordingly, in one embodiment a composition comprising a RSK inhibitory SL0101 analog is placed in contact with endothelial cells of a patient in need of reduced angiogenic activity. For example, pharmaceutical compositions comprising a RSK specific inhibitor can be used to treat diseases as diverse as arthritis, diabetic retinopathy, and cancer. In one embodiment the RSK specific inhibitory compound comprises a compound of the general structure of Formula I:

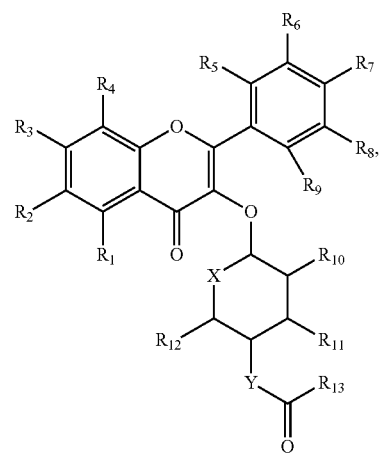

wherein $R_1$, $R_2$, $R_3$, $R_4$, $R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{12}$ is selected from the group consisting of $C_2$-$C_4$ alkyl, $C_1$-$C_4$ alkoxy, and [$C_1$-$C_4$ alkyl]$CH_2R_{18}$;

$R_{13}$ is selected from the group consisting of hydrogen, hydroxyl, and $(CH_2)_m CR_{18}R_{19} (CH_2)_n H$;

m and n are independently an integer from 0-3;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl, $C_1$-$C_4$ alkyl and $C_1$-$C_4$ alkoxy, and $R_{15}$, $R_{18}$ and $R_{19}$ are independently selected from the group consisting of hydrogen and hydroxyl.

In one embodiment the RSK inhibitory compound comprises a compound of Formula I wherein $R_2$ and $R_4$ are each hydrogen, $R_1$, $R_3$, and $R_7$ are each hydroxyl, $R_5$, $R_6$, $R_8$ and $R_9$ are independently selected from the group consisting of hydrogen, fluorine, hydroxyl, —$OCOR_{14}$, —$COR_{14}$ and $C_1$-$C_4$ alkoxy, $R_{10}$ and $R_{11}$, are independently selected from the group consisting of hydrogen, hydroxyl, —$OCOR_{14}$, and —$COR_{14}$;

$R_{12}$ is selected from the group consisting of propyl, propyloxy, and —$(CH_2)_2CH_2R_{18}$;

$R_{13}$ is selected from the group consisting of hydrogen, hydroxyl, and —$CR_{18}R_{19}H$;

X is selected from the group consisting of O, $CH_2$, and $CF_2$;

Y is selected from the group consisting of O, $NR_{15}$, and $CR_{16}R_{17}$;

$R_{14}$ is selected from the group consisting of hydrogen, and $C_1$-$C_4$ alkyl;

$R_{16}$ and $R_{17}$ are independently selected from the group consisting of hydrogen, halo, hydroxyl and $C_1$-$C_4$ alkoxy, and $R_{15}$, $R_{18}$ and $R_{19}$ are independently selected from the group consisting of hydrogen and hydroxyl. In a further embodiment, Y is O and $R_{13}$ is hydrogen or $CH_3$. In another further embodiment, $R_{10}$ and $R_{11}$, are independently selected from the group consisting of hydroxyl and —$COCH_3$; $R_{12}$ is propyl or —$(CH_2)_2CH_2R_{18}$; $R_{13}$ is hydrogen or $CH_3$, Y is O; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In an alternative embodiment the RSK inhibitory compound comprises a compound of Formula I wherein X is $CH_2$ or $CF_2$; Y is O; $R_{13}$ is —$CH_2R_{19}$ and at least one of $R_{10}$ and $R_{11}$ is hydroxyl. In a further embodiment, X is $CH_2$ or $CF_2$; Y is O; $R_{10}$ and $R_{11}$, are independently selected from the group consisting of hydroxyl and —$COCH_3$; $R_{12}$ is propyl or —$(CH_2)_2CH_2R_{18}$; $R_{13}$ is —$CH_2R_{19}$; and $R_{18}$ is hydroxyl. In a further embodiment, $R_{15}$ is hydrogen or $C_1$-$C_4$ alkyl and $R_{16}$ and $R_{17}$ are independently selected from the group consisting of hydrogen, hydroxyl and $C_1$-$C_4$ alkoxy.

In accordance with one embodiment the RSK specific inhibitory compound has the structure of Formula II:

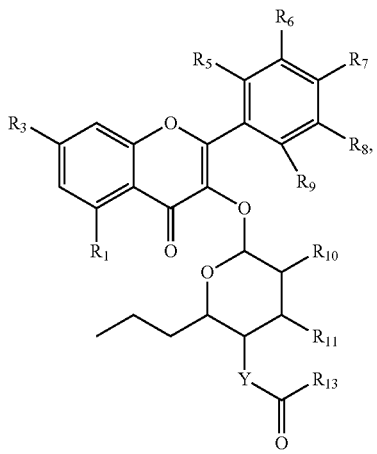

II wherein $R_1$, and $R_3$ are independently selected from the group consisting of hydroxyl, —$OCOR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$ and $R_{11}$, are independently selected from the group consisting of hydrogen, halo, hydroxyl, —$NHOCOR_{14}$, —$OCOR_{14}$, —$COR_{14}$ and $C_1$-$C_4$ alkoxy;

$R_{13}$ is selected from the group consisting of hydrogen, hydroxyl, and $(CH_2)_mCR_{18}R_{19}(CH_2)_nH$;

m and n are independently an integer from 0-3;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$, $R_{18}$ and $R_{19}$ are independently selected from the group consisting of hydrogen and hydroxyl. In further embodiment, Y is O, $R_{10}$ and $R_{11}$, are independently selected from the group consisting of hydroxyl and —$COCH_3$; $R_{13}$ is hydrogen or $CH_3$. In a further embodiment, $R_2$, $R_4$, $R_5$, $R_6$, $R_8$ and $R_9$ are each hydrogen, $R_1$, $R_3$, and $R_7$ are each hydroxyl.

In accordance with one embodiment a RSK specific inhibitory compound is provided comprising a compound of the general structure of Formula III.

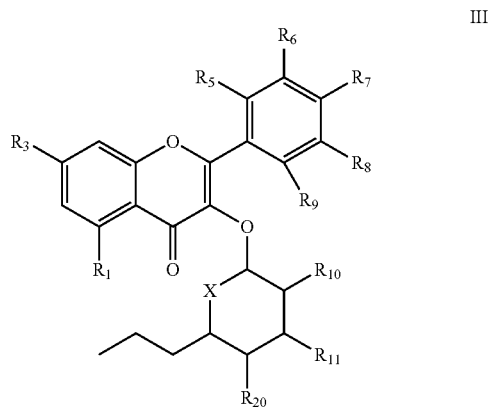

III wherein $R_1$, and $R_3$ are independently selected from the group consisting of hydroxyl, —$COCR_{14}$, —$COR_{14}$, and $C_1$-$C_4$ alkoxy;

$R_5$, $R_6$, $R_7$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of hydroxyl, —$NHOCOR_{14}$, —$OCOR_{14}$, —$COR_{14}$ and $C_1$-$C_4$ alkoxy;

X is selected from the group consisting of O, NH, $CH_2$, and $CF_2$;

Y is selected from the group consisting of O and $NR_{15}$;

$R_{14}$ is selected from the group consisting of hydrogen, and $C_1$-$C_4$ alkyl; and $R_{15}$ is selected from the group consisting of hydrogen, halo, hydroxyl, $C_1$-$C_4$ alkyl and $C_1$-$C_4$ alkoxy.

In one embodiment the RSK inhibitory compound comprises a compound of Formula III wherein X is O or $CH_2$; and $R_{10}$, $R_{11}$ and $R_{20}$ are independently selected from the group consisting of hydroxyl, —$NHOCOR_{14}$, and —$COR_{14}$, wherein at least one of $R_{10}$, $R_{11}$ and $R_{20}$ is hydroxyl. In a further embodiment, $R_5$, $R_6$, $R_8$ and $R_9$ are each hydrogen, $R_1$, $R_3$ and $R_7$ are each hydroxyl, $R_{20}$ is —$COCH_3$, and one of $R_{10}$ and $R_{11}$ is —$COCH_3$ and the other is hydroxyl.

In a further embodiment a RSK specific inhibitory compound is provided comprising a compound of Formula IV:

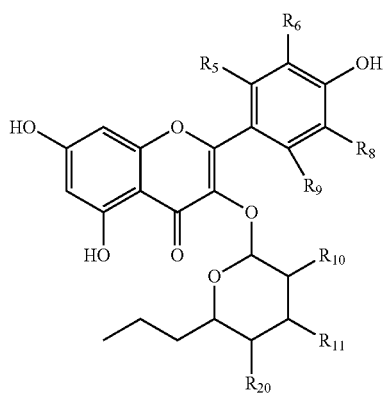

wherein $R_5$, $R_6$, $R_8$ and $R_9$ are independently selected from the group consisting of hydrogen, halo, hydroxyl, —$OCOR_{14}$, —$COR_{14}$, $C_1$-$C_4$ alkyl and $C_1$-$C_4$ alkoxy;

$R_{10}$, $R_{11}$ and $R_{20}$ are independently selected from the group consisting of —$COR_{14}$ and hydroxyl, and $R_{14}$ is selected from the group consisting of hydrogen and $C_1$-$C_4$ alkyl. In one embodiment at least one of $R_{10}$, $R_{11}$ and $R_{20}$ is hydroxyl. In a further embodiment $R_5$, $R_6$, $R_8$ and $R_9$ are each hydrogen and $R_{20}$ is —$COCH_3$ and at least one of $R_{10}$ and $R_{11}$ is hydroxyl. In a further embodiment $R_{20}$ is —$COCH_3$ and one of $R_{10}$ and $R_{11}$ is —$COCH_3$ and the other is hydroxyl.

In one embodiment the administered RSK specific inhibitor comprises a compound having the structure of Formula IV, and more particularly the RSK inhibitor has the structure:

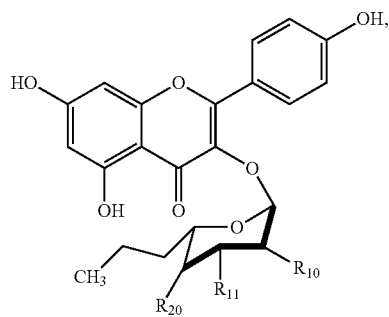

wherein $R_{10}$, $R_{11}$ and $R_{20}$ are independently selected from the group consisting of OH, $OCOR_8$, $COR_8$, $NHOCOR_8$ and $C_1$-$C_4$ alkoxy. In one embodiment, at least one of $R_{10}$, $R_{11}$ and $R_{20}$ is —$COCH_3$ and at least one of $R_{10}$, $R_{11}$ and $R_{20}$ is hydroxyl. In a further embodiment $R_{20}$ is —$COCH_3$ and one of $R_{10}$ and $R_{11}$ is —$COCH_3$ and the other is hydroxyl.

The SL0101 derivative RSK inhibitors disclosed herein can be formulated as pharmaceutical compositions and administered to a mammalian host such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the one method of preparation includes vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the novel RSK inhibitors disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the novel RSK inhibitors disclosed herein in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

As used herein, an "instructional material" includes a publication, a recording, a diagram, or any other medium of expression which can be used to communicate the usefulness of the composition of the invention for its designated use. The instructional material of the kit of the invention may, for example, be affixed to a container which contains the composition or be shipped together with a container which contains the composition. Alternatively, the instructional material may be shipped separately from the container with the intention that the instructional material and the composition be used cooperatively by the recipient.

The method of the invention includes a kit comprising a novel RSK inhibitor disclosed herein and an instructional material which describes administering the inhibitor or a composition comprising the inhibitor to a cell or a subject. This should be construed to include other embodiments of kits that are known to those skilled in the art, such as a kit comprising a (preferably sterile) solvent suitable for dissolving or suspending the composition of the invention prior to administering the compound to a cell or a subject. In one embodiment the subject is a human.

In accordance with the present invention, as described above or as discussed in the Examples below, there can be employed conventional chemical, cellular, histochemical, biochemical, molecular biology, microbiology, and in vivo techniques which are known to those of skill in the art. Such techniques are explained fully in the literature.

Without further description, it is believed that one of ordinary skill in the art can, using the preceding description and the following illustrative examples, make and utilize the compounds of the present invention. Therefore, the examples should be construed to encompass any and all variations which become evident as a result of the teaching provided herein.

Example 1

Proposed Synthetic Schemes for Preparing RSK Inhibitors

Abbreviations used in Examples 1-6 are as follows: TBDPS=tert-butyldiphenylsilyl, THF=tetrahydrofuran, EDCl=1-(3-dimethylaminopropyl)-3-ethylcarbodiimide, DMAP=4-dimethylaminopyridine, TSOH=4-toluene sulfonic acid, DMF=dimethylformamide, Bn=benzyl, MTBE=methyl tert-butyl ether.

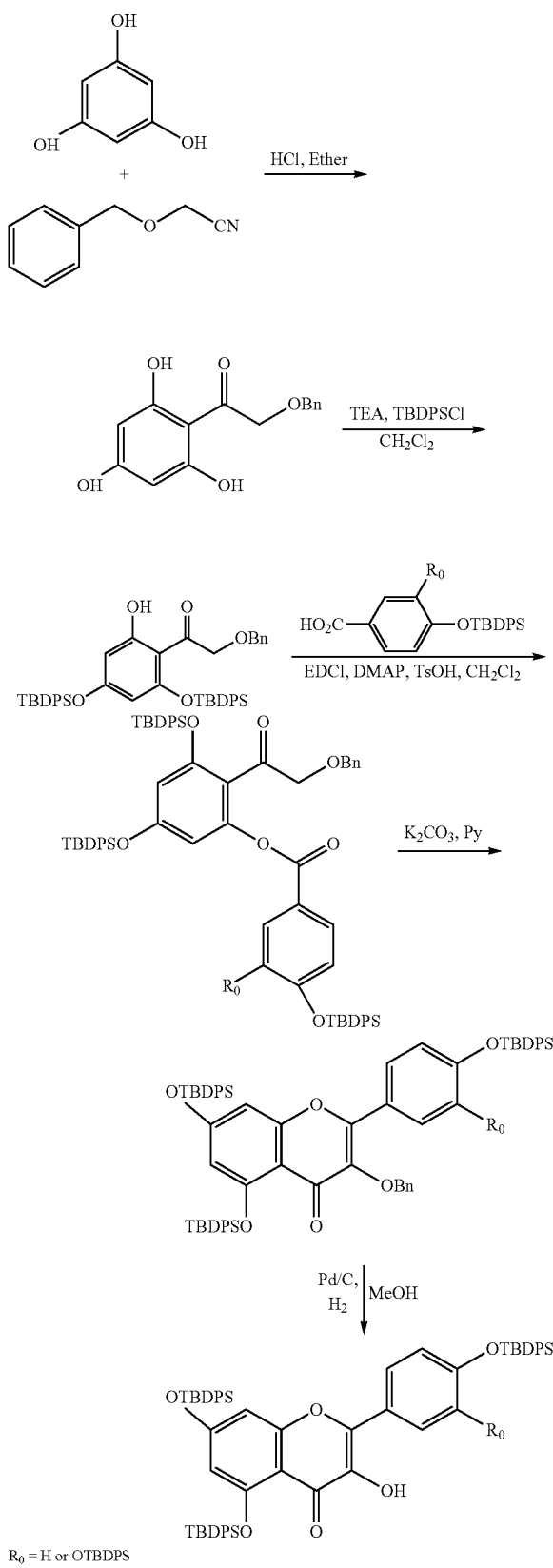
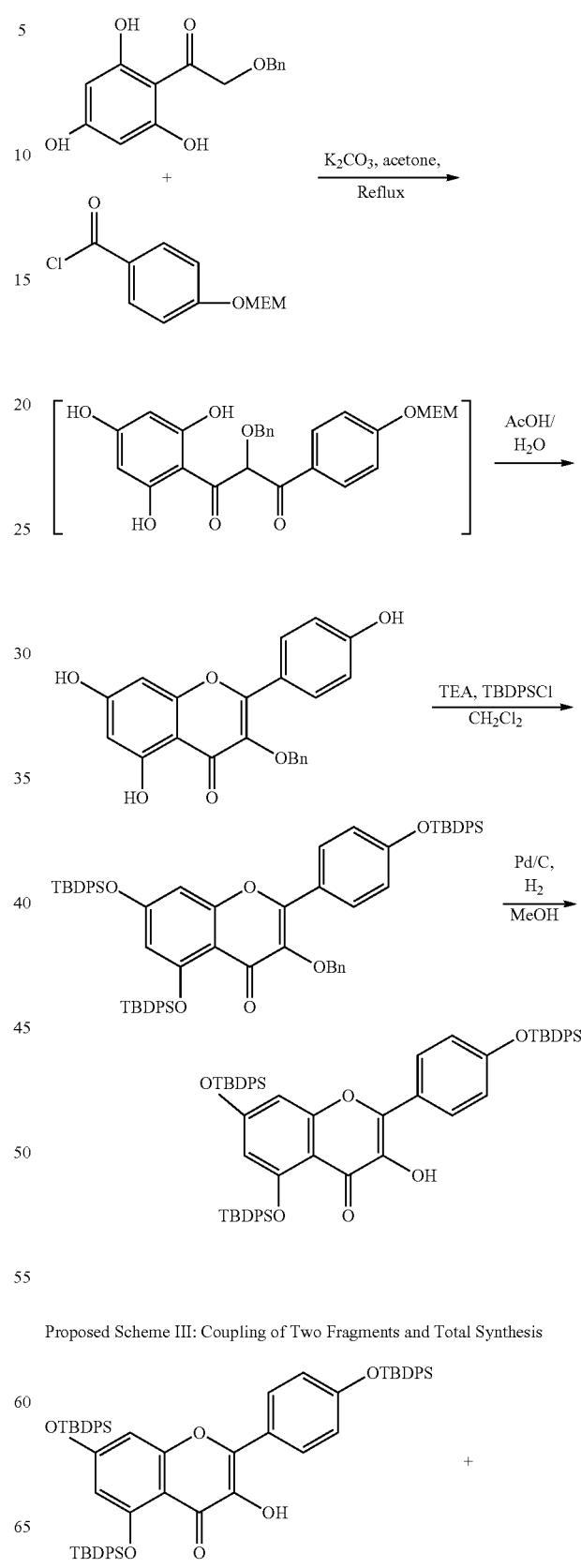

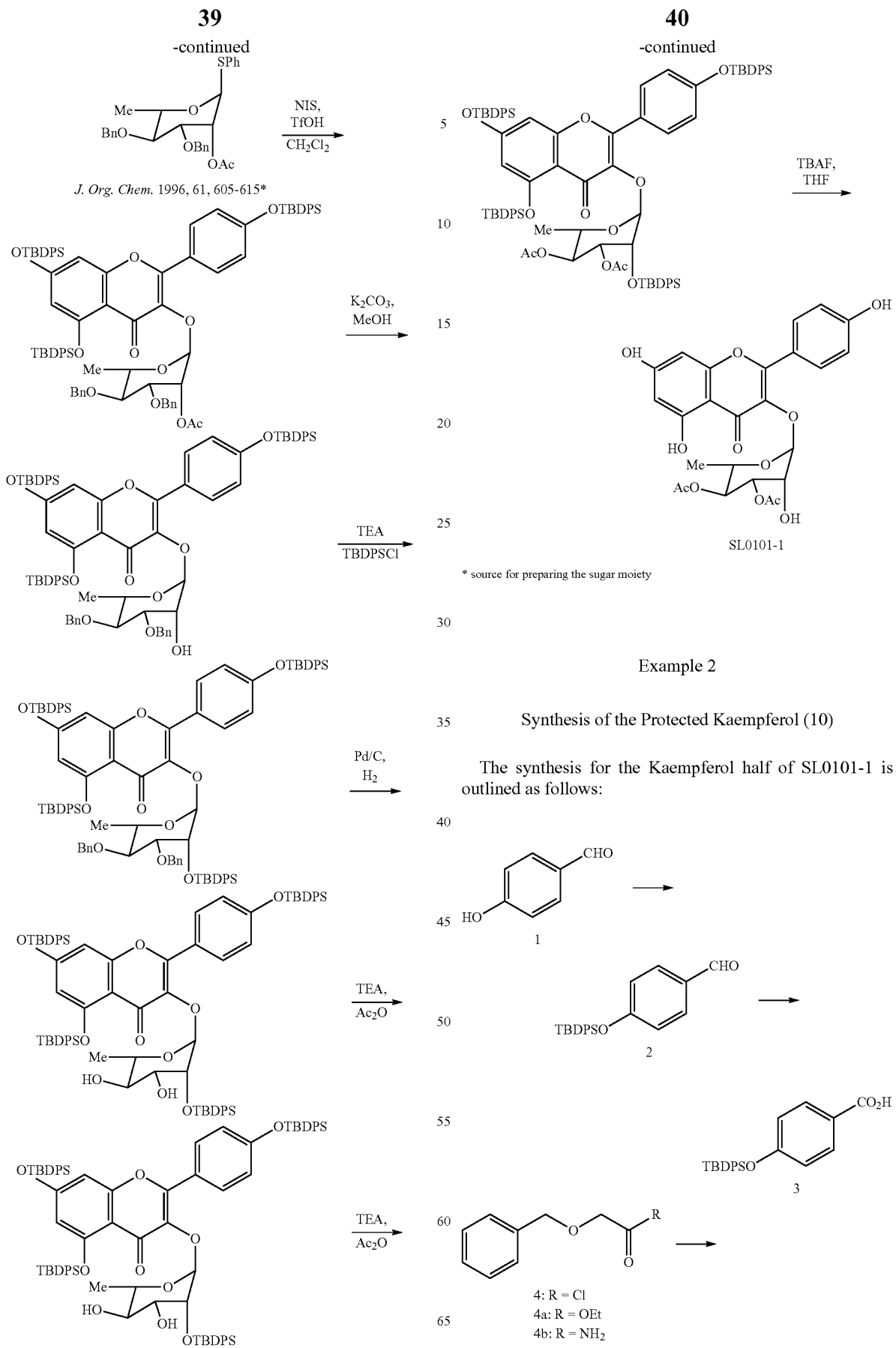
Example 2
Synthesis of the Protected Kaempferol (10)
The synthesis for the Kaempferol half of SL0101-1 is outlined as follows:

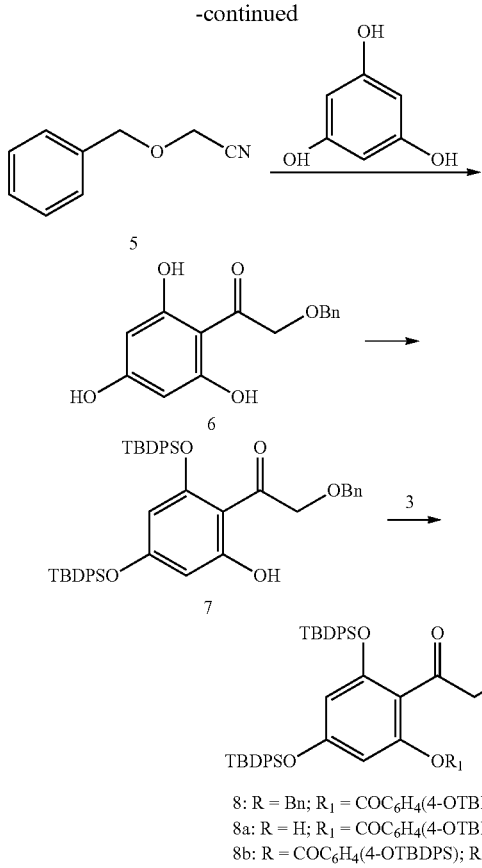

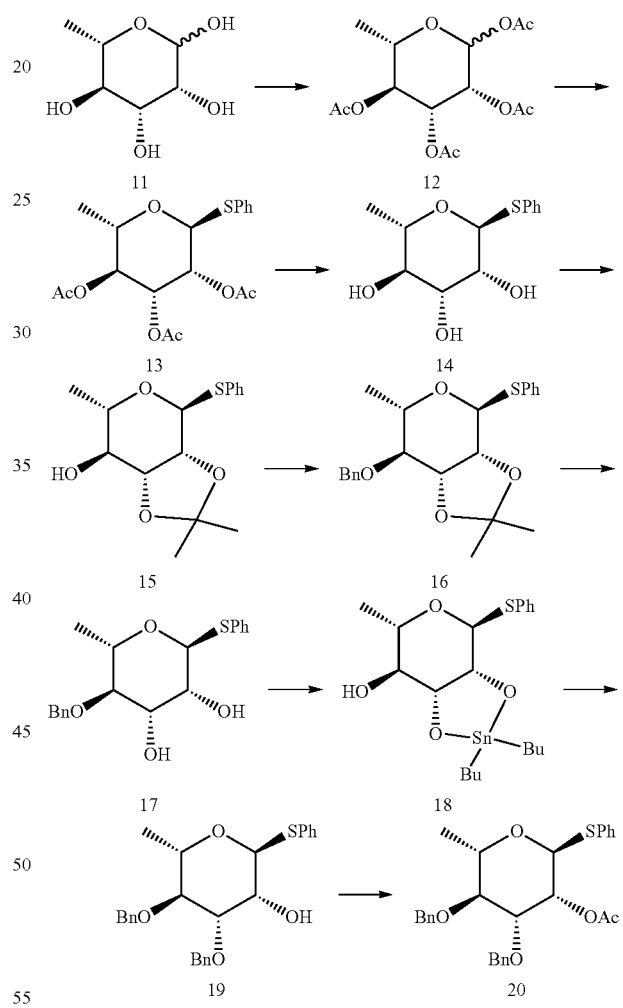

Treatment of commercially available 1 (20 g) with tert-butyldiphenylsilyl chloride (TBDPSCl) and imidazole in THF/CH$_2$Cl$_2$ gave, after chromatographic purification, 2 (47.3 g, 80%). This compound was characterized by $^1$H NMR. and MS. Oxidation of 2 (21.8 g and 25 g) using sodium chlorite gave 3 (50 g total, quantitative yield). The product was characterized by $^1$H and $^{13}$C NMR, and by MS.

Benzyl alcohol (50 g) on treatment with NaH (1.2 equiv) and ethyl bromoacetate (1 equiv) in THF gave 4a (32 g, 36%), which was characterized by both $^1$HNMR, and by MS. Scale up of this reaction yielded 100 g of 4a. Reaction of 4a (5 g) with NH$_4$OH at 0° for 5 h in CH$_2$Cl$_2$ gave amide 4b (4.3 g, 96%), which was characterized by $^1$H NMR and MS. A repeat of this experiment on 45 g of 4a gave 38 g (94%) of 4b. Dehydration of 4b (4.2 g) using POCl$_3$ in acetonitrile gave 5 (1.75 g, 47%), which was characterized by $^1$H NMR, $^{13}$C NMR and MS. A repeat of this experiment on 38 g of 4b gave an additional 15.75 g (47%) of 5. Coupling of 5 (5 g) and phloroglucinol in MTBE with HCl gas bubbling at 0° C. for 3 h gave 6 (2.6 g, 56%), which was characterized by $^1$H NMR, $^{13}$C NMR and MS. Selective protection of 6 (0.5 g) using TBDPSCl (2.5 equiv) and Et$_3$N (2.5 equiv) in CH$_2$Cl$_2$ at room temperature for 16 h gave 7 (1.2 g, 85%), which was characterized by $^1$H NMR and MS. Scale-up of this experiment on 2 g of 6 gave an additional 3.4 g (62%) of 7. Condensation of 7 (1.4 g) with 3 (1.35 equiv) in CH$_2$Cl$_2$ [EDCI (1.5 equiv), DMAP (0.35 equiv), TsOH (0.35 equiv.] at room temperature for 24 h gave 8 (1.5 g, 72%), which was characterized by $^1$H NMR. Scale up gave 35 g of purified 8. Compound 8 (6 g) was debenzylated using Rh/C as a catalyst (H$_2$, 60 psi, EtOAc, rt, 24 h) to give 8a (1.8 g, 33%) along with 2.9 g (53%) of the trans-esterified (migration of benzoyl group R$_1$) product 8b. Both the intermediates 8a and 8b were characterized by $^1$H NMR.

Example 3

Synthesis of the Protected Rhamnose (20)

The synthesis for the Rhamnose half of SL0101-1 is outlined as follows:

Reaction of L-rhamnose 11 (50 g) with acetic anhydride (6 equiv), triethylamine (8 equiv) and catalytic 4-dimethylaminopyridine (0.1 equiv) in CH$_2$Cl$_2$ at room temperature for 16 h gave 90 g (98%) of the tetraacetate 12, which was characterized by $^1$H NMR and MS and was taken to the next step without further purification. Scale up yielded 260 g of 12. Treatment of 12 (150 g) with thiophenol (1.1 equiv) in the presence of SnCl$_4$ (0.7 equiv) in CH$_2$Cl$_2$ at 0° C. for 5 h gave 13 [56 g (pure), 110 g (with ~10% impurity)], which was characterized by both $^1$H NMR and MS. Deacetylation of 13 (56 g) using catalytic $K_2CO_3$ (0.2 equiv) in THF/MeOH (1:1) at room temperature for 16 h provided triol 14 (35 g, 93%), which was characterized by $^1$H NMR and MS.

Treatment of 14 (0.3 g) using 2,2-dimethoxypropane with catalytic amount of p-toluenesulfonic acid gave 15 (0.3 g, 86%) as a single anomer, which was characterized by both $^1$H NMR and MS. Scale-up of this reaction on 34 g of 14 gave an additional 38 g (97%) of 15. O-Benzylation of 15 (0.3 g) with NaH (1.74 equiv) and benzyl bromide (1.05 equiv) in DMF provided the benzyl ether 16 (0.35 g, 89%), which was characterized by $^1$H NMR. A repeat of this experiment on 38 g of 15 gave 41 g (83%) of 16. Treatment of 16 (3 g) with trifluoroacetic acid in MeOH at 50° C. for 16 h gave diol 17 (2.5 g, 93%), which was characterized by $^1$H NMR and MS. A repeat of this experiment on 10 g of 16 gave 8.5 g (95%) of 17. Selective O-benzylation of diol 17 (2.5 g) following a literature procedure (n-$Bu_2$SnO, toluene, Dean-Stark, reflux, 4 h to give 18, then n-$Bu_4$NBr, BnBr, 50° C., 5 h) gave 19 (2.6 g, 82%), which was characterized by both $^1$H NMR and MS. Treatment of 19 (2.5 g,) with acetic anhydride and pyridine gave the acetate 20 (rhamnose part of the molecule) (2.5 g, 91%), which was characterized by $^1$H NMR and MS.

Scale-up of the above reactions to get acetate 20 (~20 g) was conducted as follows. Treatment of 16 (25 g) with trifluoroacetic acid in MeOH at 50° C. for 16 h gave diol 17 (21 g, 94%), which was characterized by $^1$H NMR and MS. Selective O-benzylation of diol 17 (29.5 g) following a literature procedure (n-$Bu_2$SnO, toluene, Dean-Stark, reflux, 4 h to give 18, then n-$Bu_4$NBr, BnBr, 50° C., 5 h) gave 19 (31 g, 83%), which was characterized by both $^1$H NMR and MS. Treatment of 19 (30 g) with acetic anhydride and pyridine gave the acetate 20 (29.3 g, 89%) required for the coupling reaction with 10. The product was characterized by $^1$H NMR and MS.

Example 4

Coupling of the Kaempferol and Rhamnose Moieties

The coupling reaction between compounds 20 and 8a to generate SL0101-1 is outlined as follows:

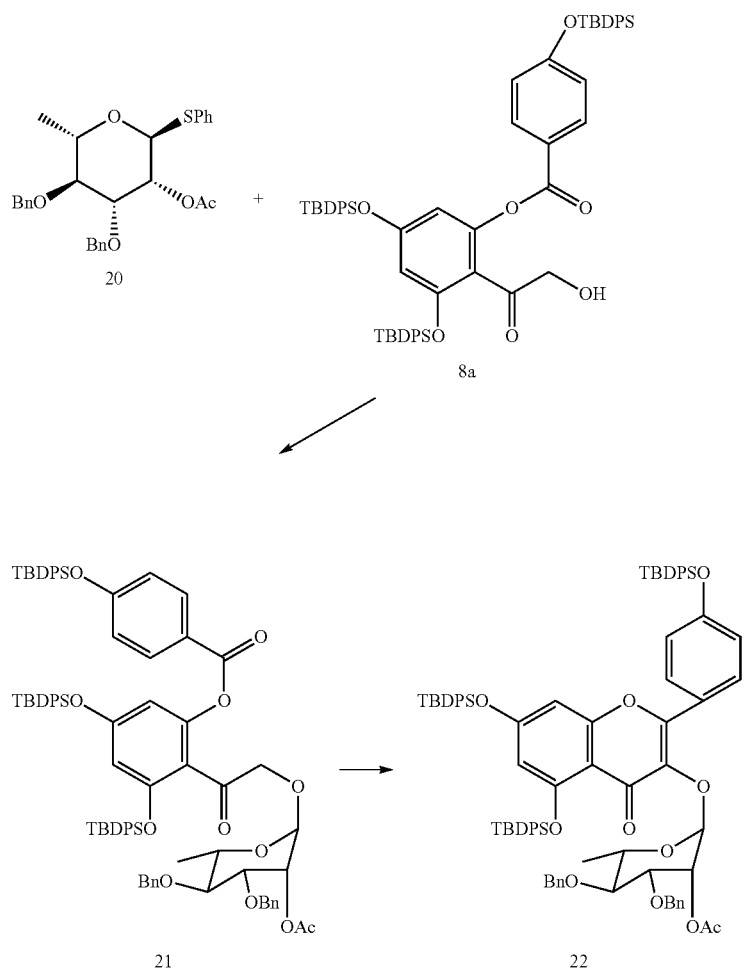

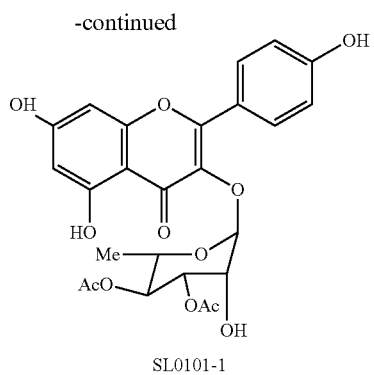

SL0101-1

The coupling of 20 (0.1 g) with 8a (1.5 equiv) using O-glycosidation conditions [1-benzenesulfinyl piperidine (1 equiv), tri-t-butylpyrimidine (2 equiv), triflic anhydride (trifluoromethanesulfonic acid anhydride) (1.1 equiv), $CH_2Cl_2$, $-60°$ C., 1 h] gave 21 (0.1 g, 35%), which was characterized by $^1H$ NMR. Dehydration of 21 (0.1 g) using $K_2CO_3$ in pyridine at reflux to get 22 is in progress and the remaining steps from 21 to produce SL0101-1 are well known to those skilled in the art.

Example 5

Synthesis and identification of novel RSK-specific Inhibitors based on the SL0101 (I) framework to prepare SL0101 analogues (2,3):

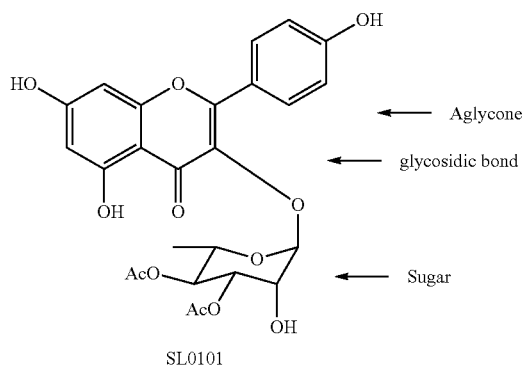

SL0101

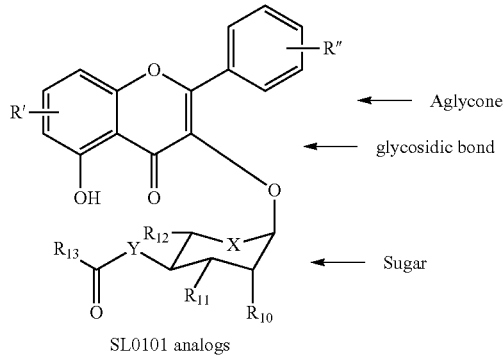

SL0101 analogs

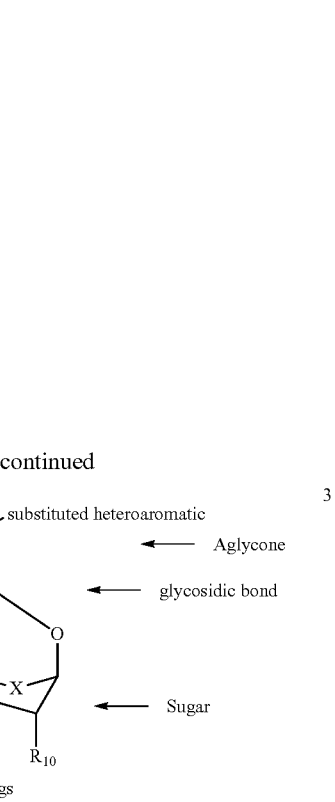

SL0101 analogs

Synthetic Description:

Synthesis of the Aglycone moiety of the SL0101 analogs can be prepared as described in Scheme I or II of Example 1 or as described in Example 2. The first route as outlined in Scheme IV involves a direct coupling of the desired aglycone (with the required protecting groups) and a suitably protected sugar/cyclitol coupling partner which can be coupled via a direct glycosylation (SN1 or SN2)/cyclitolization reaction (SN2). The product of this coupling is then deprotected as required.

Scheme IV: Method 1 for preparation (via the direct coupling of sugar or cyclitol with the aglycone, followed by deprotection when needed)

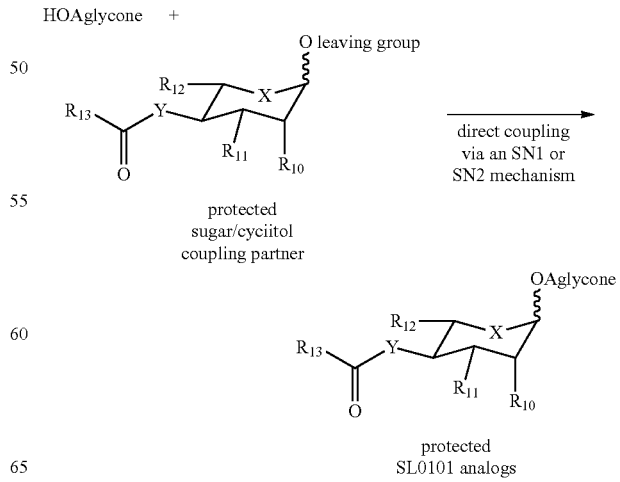

protected sugar/cyciitol coupling partner protected SL0101 analogs

Scheme IV: Method 2 for Preparation (Via a Pd-Catalyzed Glycosylation/Cyclitolization Followed by Installation of Desired Functional Group(s) and Deprotection)

The second route as outlined in Scheme 2 involves a direct coupling to the desired aglycone (with the required protecting groups) and a suitably protected pyranone/Enone coupling partner which can be coupled via a Pd-catalyzed glycosylation/cyclitolization reaction. The pyranone/enone product of this coupling is then converted into a pyran product with the appropriate C-4 functionality. Alternatively, this product can be prepared from the aglycone and a suitably protected pyran/cyclohexene coupling partner which can be coupled via a related Pd-catalyzed glycosylation/cyclitolization reaction. Finally the C2/C3 functionality can be installed via post-glycosylation transformations and any protecting groups can be removed.

sugar moiety reducing acid and enzymatic hydrolysis and thus provides substantially improved overall bio stability.

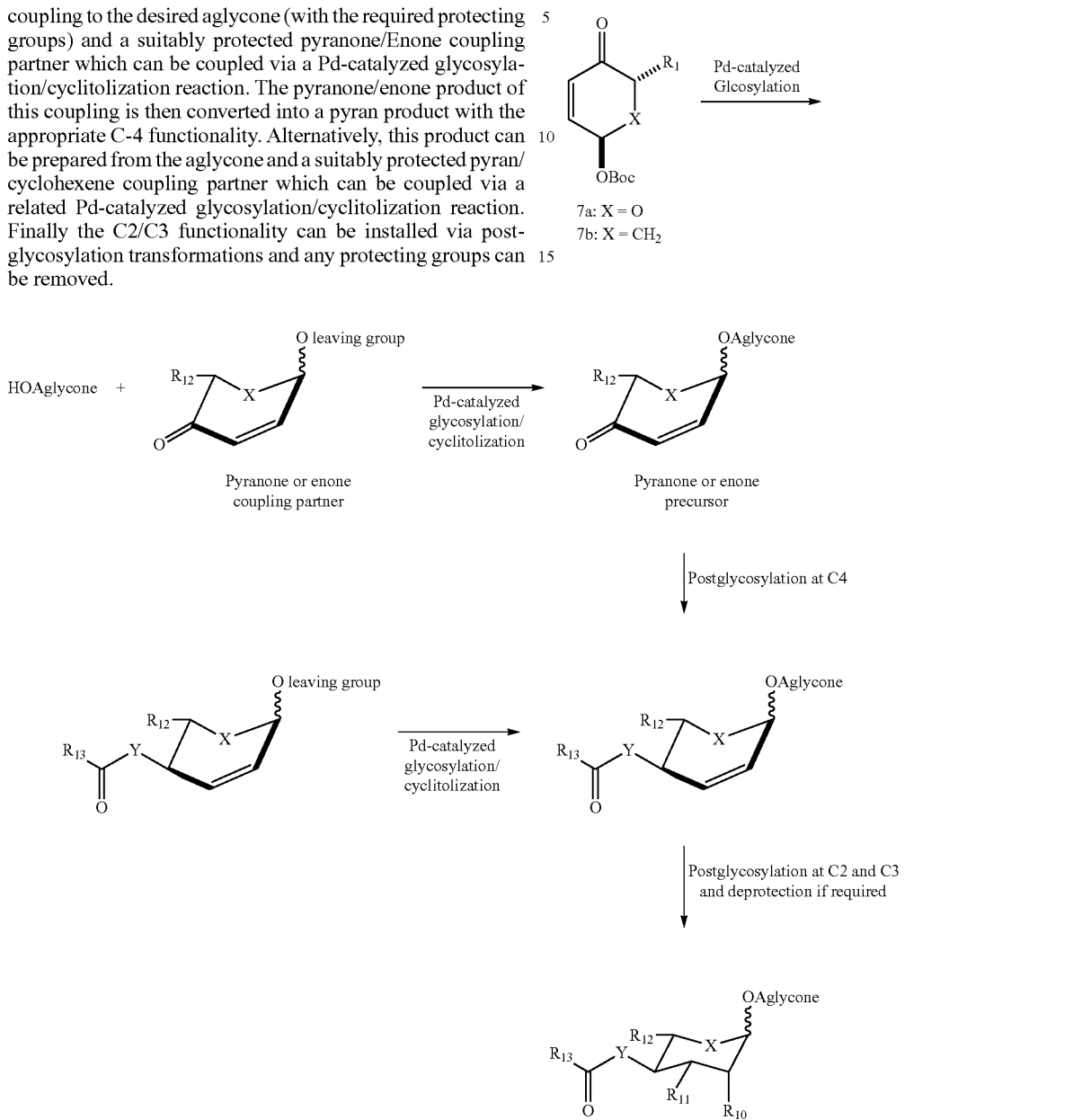

The precedent for these approaches can be found in David J. Maloney and Sidney M. Hecht, *Organic Letters* (2005) Vol. 7, No. 6. pp 1097-1099, Mingde Shan and George A. O'Doherty, *Organic Letters* (2006) Vol. 8, No. 22. pp 5149-5152 and Mingde Shan and George A. O'Doherty, *Organic Letters* (2010) Vol. 12, No. 13. pp 2986-2989.

Example 6

Synthesis of SL0101 Carbasugar Analogues

Carbasugars have been known as sugar mimics, in which the ring oxygen of the sugar moiety was replaced with a methylene group. This substitution imparts stability to the -continued

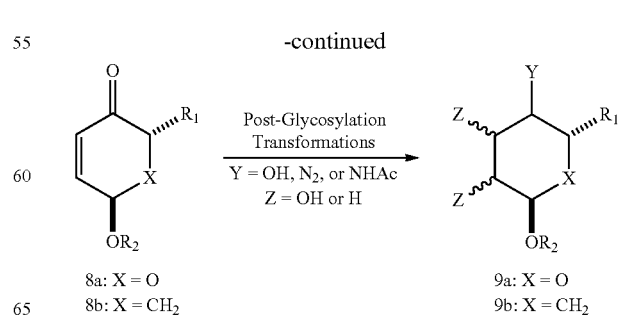

Because the palladium glycosylation reaction uses the double bond to stabilize the carbocation intermediate, the ring oxygen is not needed. For the cyclitolization reaction variant to work as well, the electron withdrawing C-4 ketone must direct the incoming nucleophile to the C-1 sugar position. The desire for this transformation required the use of a Bocenone 7b instead of a Boc-pyranone 7a in an analogous Pdcatalyzed cyclitolization (7b to 8b), which would install the carbasugar glycosidic bond in 8b. In turn, suitable postcyclitolization transformations (8b to 9b) could be used to install the remaining carbasugar functionality.

We have developed a stereodivergent synthesis of either enantiomer of the required Boc-enones from D-quinic acid. Thus, both R-L-Boc-enone 7b and R-D-Boc-enone ent-7b were prepared in 12 and 11 steps from quinic acid 10 (See Shan, M.; O'Doherty, G. A. Org. Lett. 2008, 10, 3381-3384 and Shan, M.; O'Doherty, G. A. Synthesis 2008, 3171-3179). This synthetic route provided ample quantities of the two enantiomeric D- and L-Boc-enones.

The carbasugar studies began with an investigation of the palladium(0)-catalyzed cyclitolization. In practice, R-D-Bocenone (ent-7b) was treated with BnOH in CH$_2$Cl$_2$ in the presence of 10 mol % of Pd(PPh$_3$)$_2$ [Pd(PPh$_3$)$_2$=Pd$_2$(dba)$_3$·CHCH$_3$/4PPh$_3$] at 0° C. for 12 h. As a result, the reaction afforded glycosylated enone 11 in a reasonable 60% yield. After screening a variety of reducing agents, we found LiAlH$_4$ reduction at −78° C. resulted in a reasonable diastereoselectivity of 11:1 to afford allylic alcohol with 85% yield. The minor diastereomer could be removed by silica gel chromatography. To install the cis-diol, allylic alcohol was then dihydroxylated at 0° C. upon Upjohn conditions (OsO$_4$/NMO; VanRheenen, V.; Kelly, R. C.; Cha, D. Y. Tetrahedron Lett. 1976, 17, 1973-1976) 11 which afforded triol in 90% yield with complete stereocontrol.

Next Pd-cyclitolization with phenolic and enolic nucleophiles was investigated because the aglycon of SL0101 is an enolic nucleophile. For this purpose, a number of phenol/enol nucleophiles with different substitution patterns were chosen for testing. The Pd-cyclitolization was found to work very well with reasonable to excellent yields even for those phenols/enols either with sterically demanding or highly electron deficient substituents. With the phenol/enol nucleophiles, there is the added issue of O- vs C-allylation and/or accompanied Claisen rearrangements. Thus, we were delighted to see that for this cyclitolization, this appeared not to be a problem. It is also worth mentioning that the Pd catalyst loading could be lowered to 5 mol % with the reaction times remaining in the 0.5-2 h range.

The synthesis of SL0101 carbasugar glycoside analogues was conducted using a Pd-cyclitolization reaction with a suitably protected SL0101 aglycon 15 (Scheme V). In practice, the reaction between flavonol 15 and R-DBoc-enone 7b went smoothly in CH$_2$Cl$_2$ in the presence of 5 mol % of Pd catalyst at 0° C. in 30 min to afford desired glycosylated enone 16 in 84% yield.

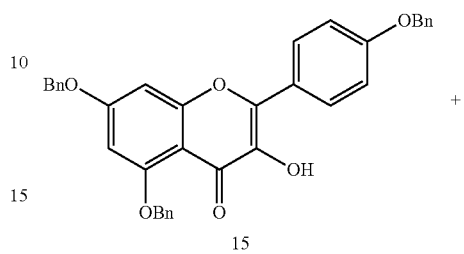

15

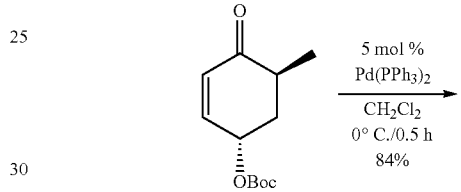

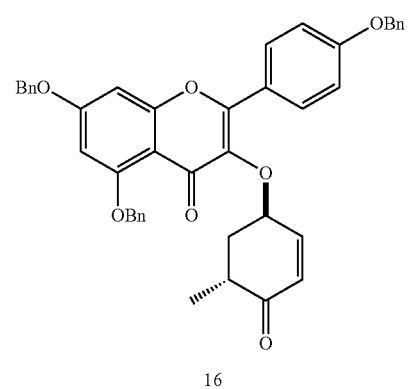

16

To install the remaining SL0101 functionalities in the carbasugar, we explored the postcyclitolization transformation. Reduction of the glycosylated enone 16 with LiAlH4 at −78° C. afforded allylic alcohol (89%, dr 11:1), which was acylated to give allylic acetate 17 in 93% yield (Scheme VI). Dihydroxylation of the olefin furnished a diol 18 as a single diastereomer (73%), which was then debenzylated via hydrogenolysis with Pd/C to afford one carbasugar glycoside analogue of SL0101, the C-4 monoacetate 6, in 68% yield.

51
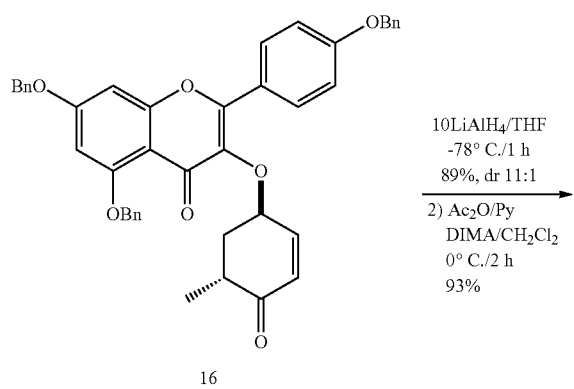
16
10 LiAlH₄/THF
-78° C./1 h
89%, dr 11:1
2) Ac₂O/Py
DIMA/CH₂Cl₂
0° C./2 h
93%
52
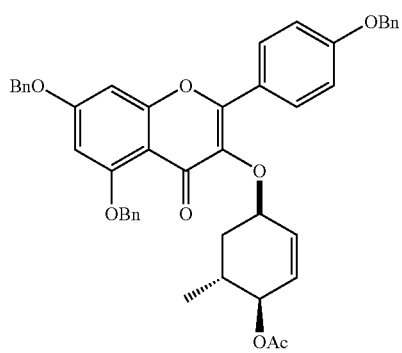
17
OsO₄/NMO
t-BuOH
acetone
0° C./20 h
73%
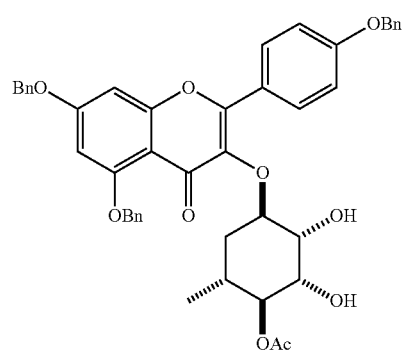
18
H₂, Pd/C
THF/EtOH
RT/12 h
68%
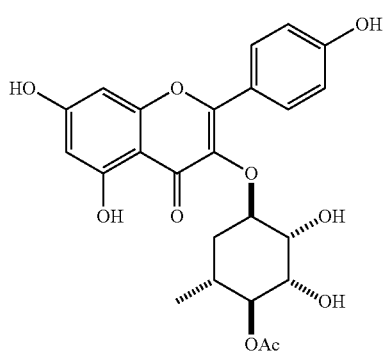
6
Ip-tsOH
CH₂Cl₂
0° C./20 min
then 90% HOAc
15 min
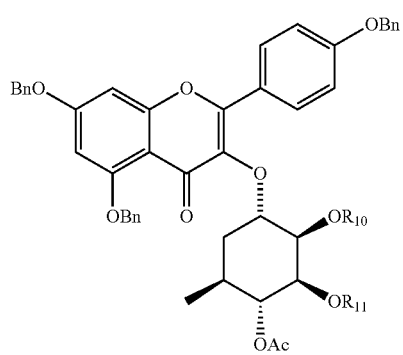
19 R₁₀ = Ac, R₁₁ = H
20 R₁₀ = H, R₁₁ = Ac In order to achieve the diacetate carbasugar glycoside analogues of SL0101, a selective C-2 acylation was carried out on diol 18 via orthoacetate formation and kinetic hydrolysis. Surprisingly, when diol 18 was reacted with trimethyl orthoacetate at 0° C. in the presence of a catalytic amount of p-toluenesulfonic acid, followed by hydrolysis using 90% aqueous acetic acid, a mixture of 2,4-diacetate 19 and 3,4-diacetate 20 in a 1.5:1 ratio was obtained.

This result stood in contrast to the completely regioselective acylation of the axial hydroxy group in the synthesis of SL0101, 5 indicating a significantly less rigid chair conformation for this rhamno-carbasugar versus the rhamno-sugar. This is presumably due to the loss of anomeric effect. After separation of these two regioisomers on silica gel chromatography, 19 and 20 were per-debenzylated with $H_2$ upon Pd/C producing the other two desired SL0101 carbasugar analogues, the C-2,C-4 diacetate 5 (63%) and the C-3,C-4 diacetate 4 (75%), respectively.

The synthesis of the enantiomeric carbasugar glycoside analogues (ent-4, ent-5, and ent-6) was accomplished by simply switching the R-L-Boc-enone 7b to R-D-Boc-enone ent-7b. A Pd-catalyzed cyclitolization of kaempferol 15 with Boc-enone ent-7b afforded 85% yield of enone ent-16 under the same conditions as before, and after the same sequence of postcyclitolization transformation, carbasugar glycoside analogue of SL0101, C-4 monoacetate ent-6 was obtained (Scheme 8). By a similar orthoacetate formation and kinetic hydrolysis with 90% acetic acid, the diol ent-18 was converted to a mixture of diacetate ent-19 and ent-20 in a ~1:1 ratio. Global debenzylation of these two precursors by hydrogenation afforded the enantiomeric carbasugar glycoside of SL0101, C-2,C-4 diacetate ent-5 and C-3,C-4 diacetate ent-4.

In conclusion, six SL0101 carbasugar glycoside analogues in either enantiomeric form have been synthesized successfully. The formation of the key glycosidic bond features a highly regio- and stereospecific Pd-catalyzed cyclitolization.

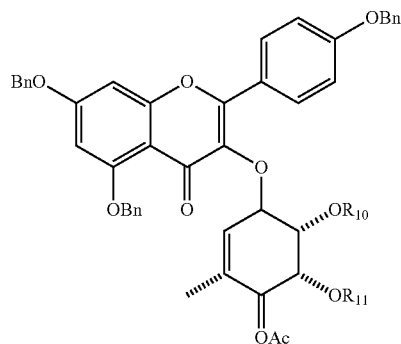

19 $R_{10}$ = Ac, $R_{11}$ = H          20 $R_{10}$ = H, $R_{11}$ = Ac

$H_2$, Pd/C
THF/EtOH
RT/12 h
63%

$H_2$, Pd/C
THF/EtOH
RT/7 h
75%

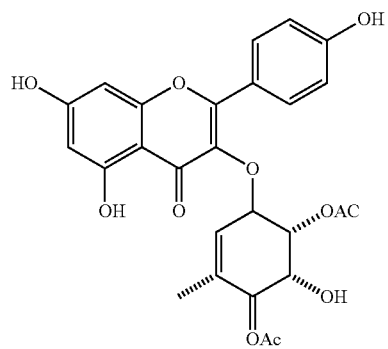

5

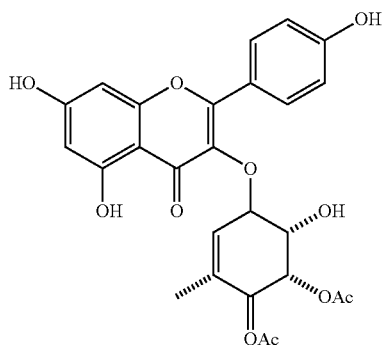

4

The functionalities on the sugar moieties have been established via corresponding postcyclitolization transformations.
The following compounds have been synthesized:
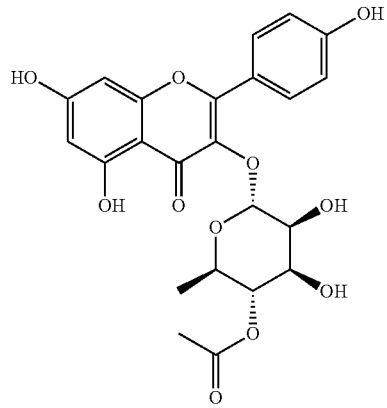
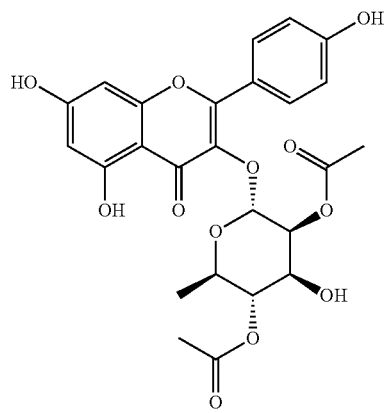
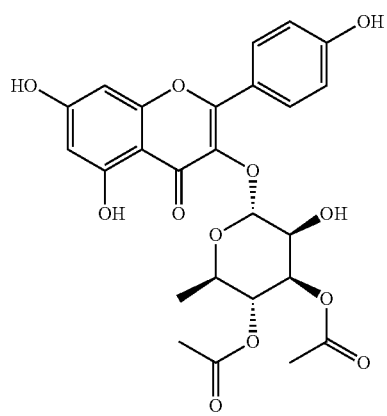
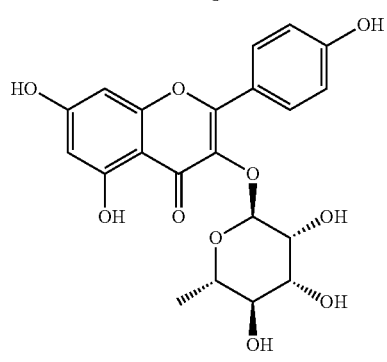
-continued
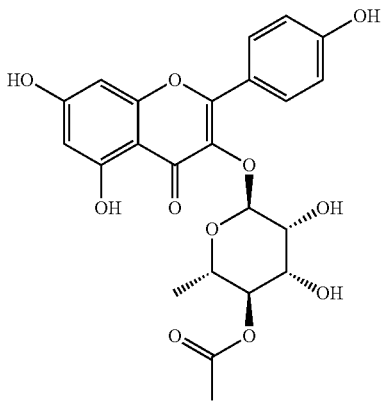
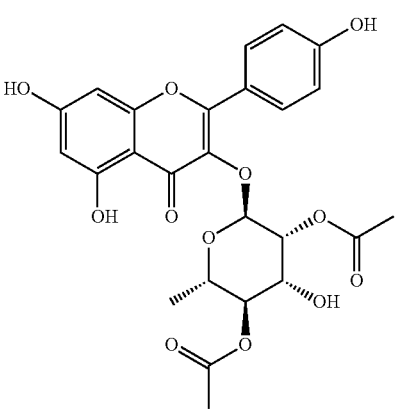
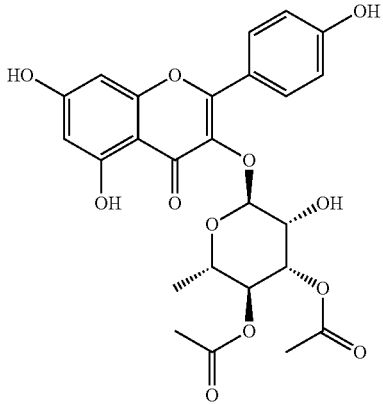
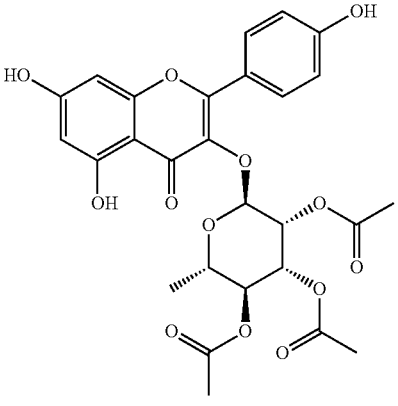

57
-continued
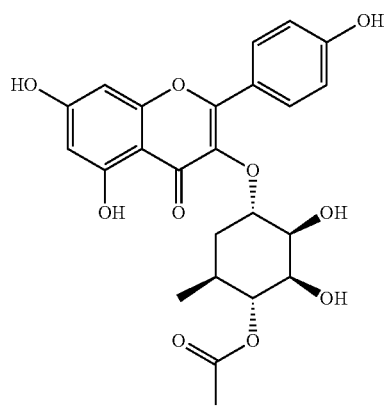
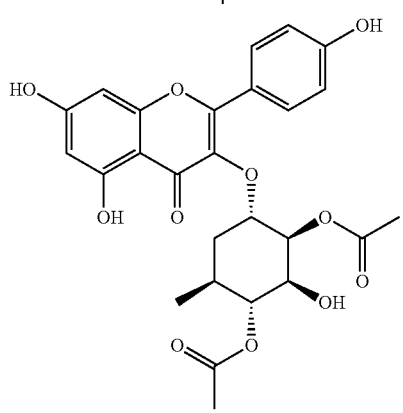
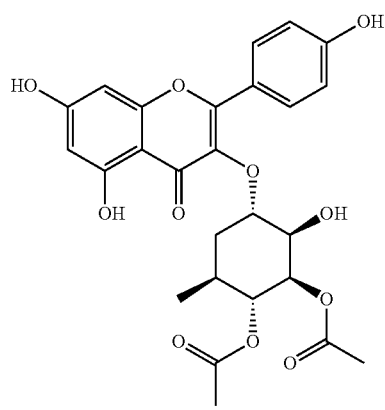
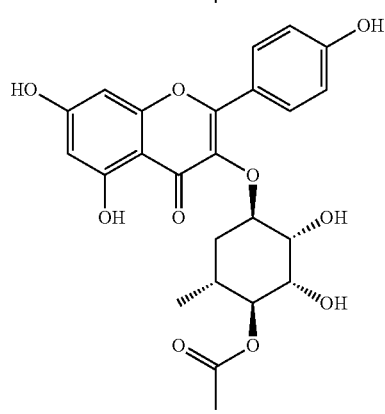
58
-continued
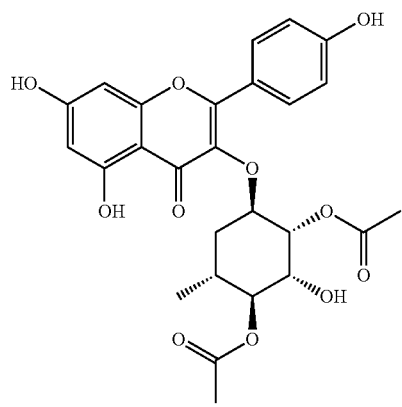
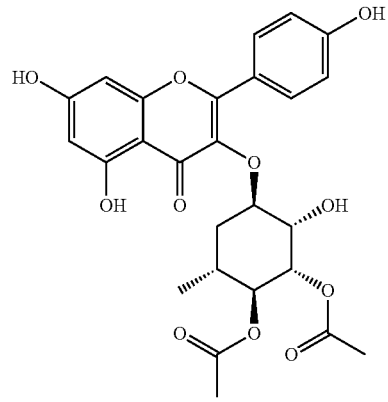
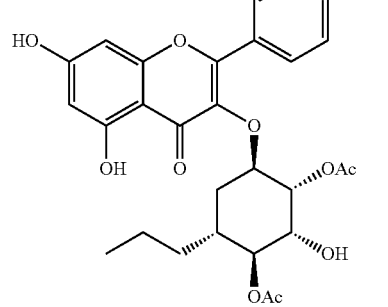
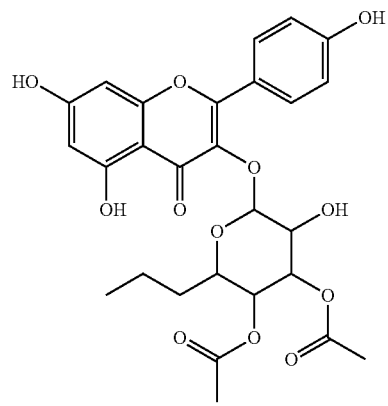

-continued

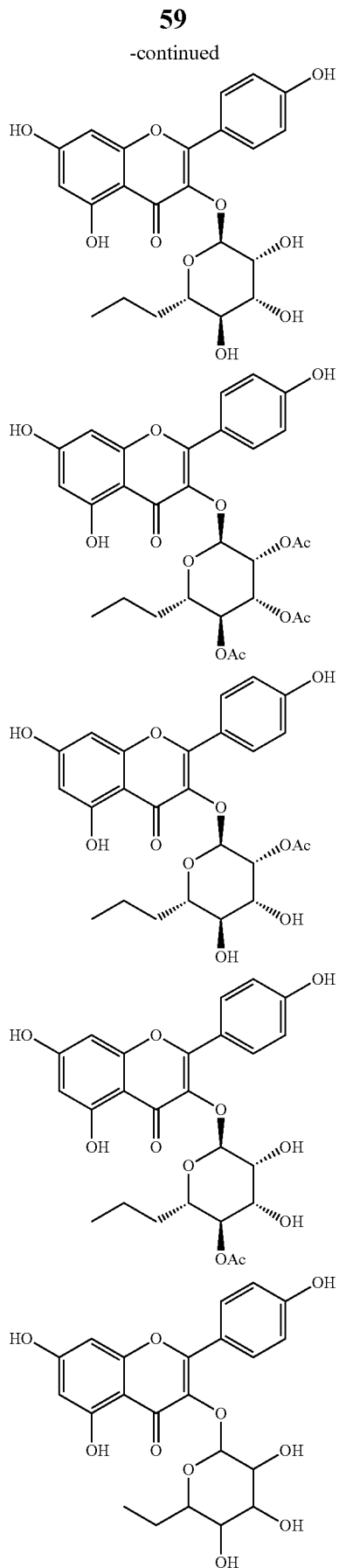

-continued

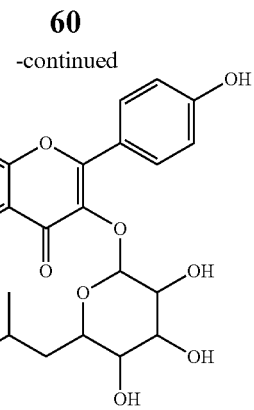

Example 7

Inhibition of RSK Activity Reduce LPS Activated Macrophage Secretions

To determine that SL0101 inhibits RSK activity in J774A.1 murine macrophages, the effect of SL0101 on phosphorylation of eukaryotic elongation factor (eEF2) was investigated. The translocation step in mRNA translation is mediated by eEF2. The activity of eEF2 is regulated by phosphorylation such that in the unphosphorylated state eEF2 is active and in the phosphorylated state eEF2 is inactive. This phosphorylation is produced by a highly specific kinase, EF2 kinase (EF2K). RSK phosphorylates and inactivates EF2K in response to mitogenic stimulations, which leads to a decrease in eEF2 phosphorylation (Wang, et al. Embo J 20:4370-9). Under conditions in which RSK activity is low, as during serum deprivation, eEF2 is phosphorylated by the active EF2K. However, stimulation of RSK activity by mitogens such as phorbol dibutyrate (PDB) results in reduced phosphorylation of eEF2 due to inactivation of EF2K by RSK. Therefore, the phosphorylation state of eEF2 is an indicator of RSK activity. As expected, RSK inhibition by SL0101 increases peEF2 levels because RSK no longer inhibits EF2K. The levels of total eEF2 were not altered by any of the treatments. Thus SL0101 inhibits RSK activity in J774A.1 cells and the phosphorylation state of eEF2 can be used to detect RSK inhibition the macrophages.

Figure 2A:
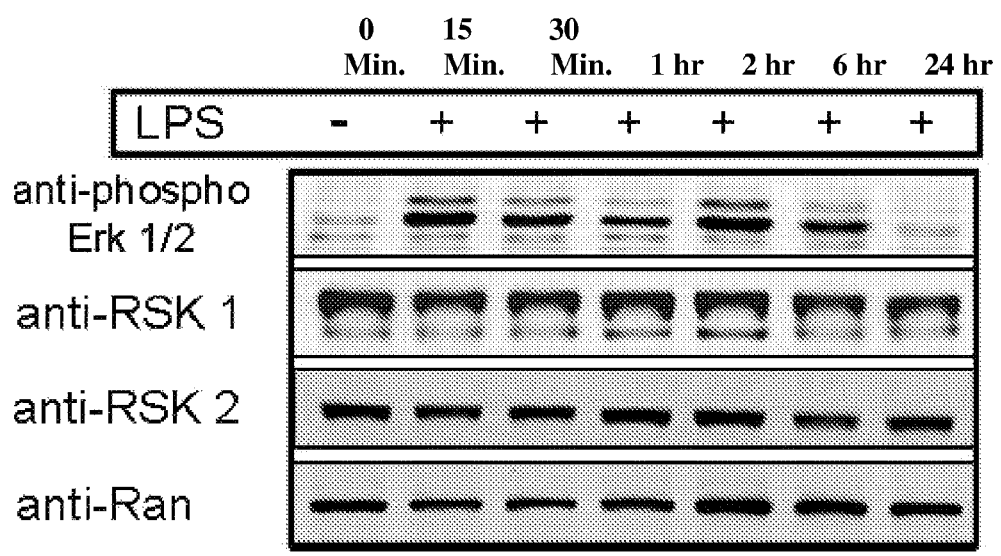
Figure 2B:
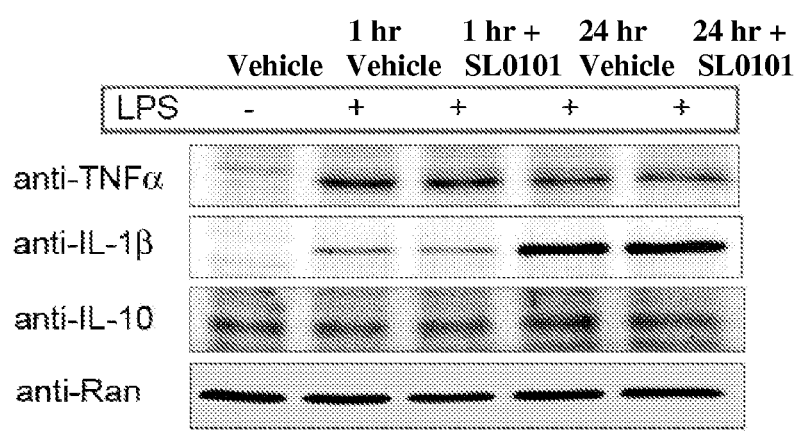
Figure 3A:
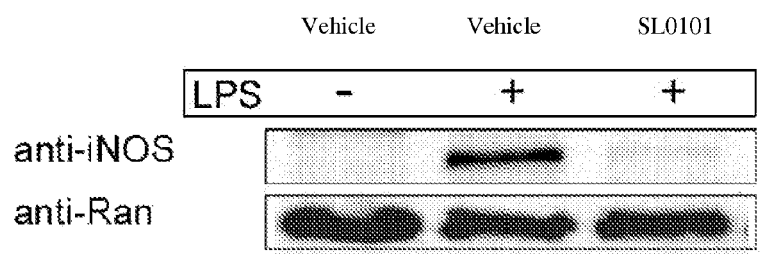
Figure 3B:
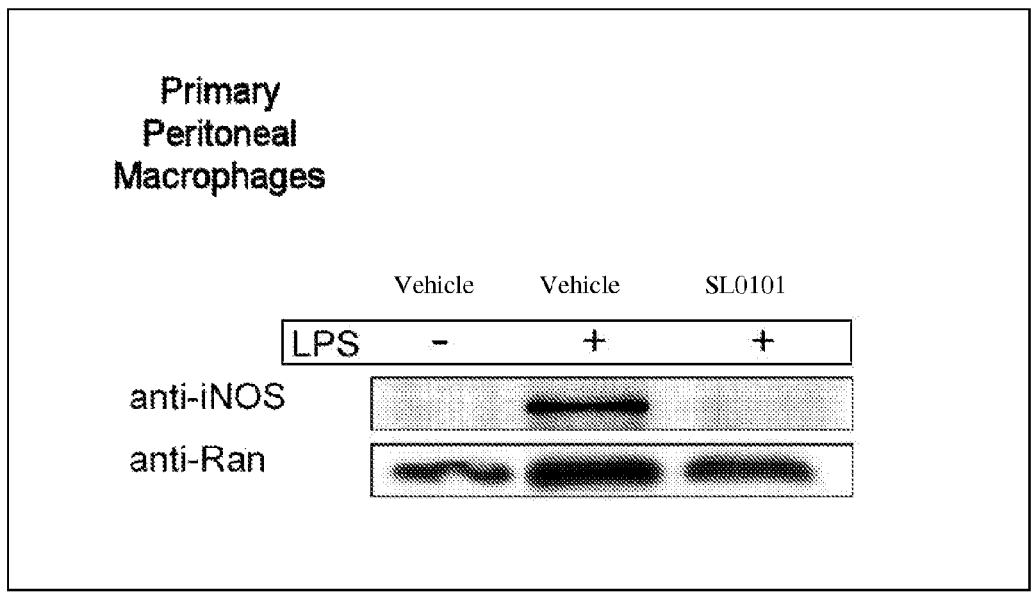

LPS activation of macrophages results in secretion of factors that stimulate the innate immune system. To examine the effect of RSK inhibition on the expression of these factors, J774A.1 cells were treated with 1 µg/ml LPS (*Escherichia coli* 0111:B4, Sigma L4391) and 60 µM SL0101 or vehicle. Twenty-four hours after LPS treatment the cells were lysed as previously described (Traish, et al., 1998. J. Biol. Chem. 273:13317-13323) in preparation for immunoblot analysis. Expression of the pro-inflammatory factors, TNFα, IL-1b, the anti-inflammatory factor, IL-10 and inducible nitric oxide synthase was examined by immunoblot of the cell lysates. Analysis revealed that LPS treatment resulted in activation of p42/44 MAPK (Erk 1/2) and increased expression of the cytokines, TNFα and IL-1b (FIGS. 2A & 2B). Inhibition of RSK with SL0101 did not alter the expression of TNFα, IL-1b of IL-10. However, RSK inhibition by SL0101 abrogated the induction of iNOS expression (FIG. 3A). In addition, RSK inhibition was shown to have the same effect in primary murine peritoneal macrophages (see FIG. 3B).

These data indicate that inhibition of RSK activity in the macrophages does not simply shut down the immune response of the macrophage due to general toxicity. Therefore, RSK inhibition modifies the pattern of factors expressed upon LPS exposure by altering expression of specific LPS-induced genes. It was previously shown that RSK activity is required for phorbol ester induced COX-2 expression in human fibroblasts (Cieslik, et al., 2005. J Biol Chem 280: 18411-7). As demonstrated herein, RSK activity is required for LPS-stimulated iNOS expression. Thus, RSK activity is essential for induction of at least two factors integral to the inflammatory response of macrophages to LPS-challenge.

Additionally, we demonstrated that inhibition of RSK in human umbilical vein endothelial cells (HUVEC) attenuates LPS-induced expression of vascular cell adhesion molecule (VCAM), see Example 12. The reduction in endothelial cell adhesion molecule expression should interfere with the conversion of the cells from the anti- to pro-adhesive phenotype. Therefore, inhibition of RSK not only alters LPS-induced macrophage secretions but also attenuates LPS activation of endothelial cells.

The data provided in FIGS. 2-3 supports the use of RSK inhibitors as pharmacological agents to treat and recalibrate inflammatory responses. Accordingly, RSK inhibitors will be useful therapeutic agents for reducing the development of septicemia as well as for treating diseases associated with chronic inflammation such as rheumatoid arthritis, inflammatory bowel syndrome, atherosclerosis, multiple sclerosis, asthma, and diabetes.

Example 8

SL0101 Interferes with the Ability of *Y. pseudotuberculosis* to Impede Endosomal/Phagosomal Maturation It is known that *Y. pestis* and the parent species, *Y. pseudotuberculosis* impede maturation of the endosome/phagosome. As demonstrated herein the RSK-specific inhibitor, SL0101, interferes with the ability of *Y. pseudotuberculosis* to impede endosomal/phagosomal maturation.

In a typical infection, shortly after *Yersinia pseudotuberculosis* is internalized into the host cell, the cytoskeleton of the host cell is rearranged resulting in accumulation of a thick actin ring around the early endosomal vesicle. It has been suggest for *Leishmania donovani* infections that fusion of the endosomal and lysosomal vesicles is inhibited by enveloping the early endosome with the actin ring (Lerm et al. 2006. Infect Immun 74:2613-8). The *Y. pseudotuberculosis*-containing endosomes in macrophages treated with SL0101 exhibit no actin ring enveloping the early endosomes. In fact, *Y. pseudotuberculosis*-induced actin rearrangement is not observed in SL0101-treated macrophages. Thus, it appears that SL0101 treatment protects the host cell cytoskeleton from *Y. pseudotuberculosis*-induced reorganization.

The functional consequence of SL0101 interfering with the ability *Y. pseudotuberculosis* to impede endosomal and lysosomal fusion would be the restoration of the microbicidal function of the macrophage. Thus, SL0101 treatment of macrophages is anticipated to result in fewer bacteria surviving internalization into the host cell. As seen in FIG. 4A, fewer live bacteria are extracted from cells treated with SL0101 relative to the bacteria extracted from vehicle-treated macrophages. Furthermore, as shown by the data of FIG. 4B, SL0101 does not directly affect the growth of *Y. pseudotuberculosis*. Thus, SL0101-treatment interferes with accumulation of the actin ring around the early endosome and most likely functions to inhibit infection by restoring function to the microbicidal machinery of the host cell.

The data presented in FIG. 4 demonstrates that SL0101 represents one member of a novel class of anti-infective agents that protect the host by interfering with the ability of the pathogen to disrupt or avoid the microbicidal machinery of the host cell. Thus, SL0101 has the potential to provide protection from a number of intracellular pathogens that survive in the host cell by inhibiting endosome/phagosome maturation including those organisms listed in Table 1.

TABLE 1

List of Intracellular Pathogens that Impede Phagosome Maturation

| Pathogen | Pathology | Reference |
|---|---|---|
| *Fancisella Tularensis* | Tularemia | (7) |
| *Yersinia Pestis* | Plague | (8) |
| *Legionella Pneumophila* | Legionnaires | (9) |
| *Mycobacterium Tuberculosis* | Tuberculosis | (10) |
| *Mycobacterium Leprae* | Leprosy | (11) |
| *Helicobacter Pylori* | Peptic Ulcer Disease | (12) |
| *Salmonella Enterocolitica* | Enterocolitis | (13) |
| *Salmonella Typhi* | Typhoid Fever | (14) |
| *Neisseria Gonorrhea* | Gonorrhea | (15) |
| *Brucella* | Brucellosis | (16) |
| *Coxiella* | Q Fever | (17) |
| *Chlamydia Trachomatis* | *Chlamydia*, Pneumonia | (18) |
| *Leishmania donovani* | Leishmaniasis | (6) |
| *Toxoplasma gondii* | Toxoplasmosis | (19) |

Example 9

Inhibition of Cell Proliferation by RSK Inhibitors

To determine whether SL0101-1 inhibits RSK in intact cells, phosphorylation of p140, a RSK substrate of unknown function, was examined in a human breast cancer cell line, MCF-7. MCF-7 and MCF-10A cells were pre-incubated with vehicle, 50 μM U0126 or the indicated concentration of SL0101-1 for 3 hr (FIG. 8D). Cells were treated with 500 nM PDB for 30 min prior to lysis. Protein concentration of lysates was measured and lysates were electrophoresed, transferred and immunoblotted. Equal loading of lysate is demonstrated by the anti-Ran immunoblot. Pre-incubation of cells with 100 μM SL0101-1 abrogates phorbol dibutyrate (PDB)-induced p140 phosphorylation as does 50 μM U0126, a MEK inhibitor. SL0101-1 does not effect the phosphorylation of RSK2, as indicated by the reduced electrophoretic mobility of RSK2, nor the activation of MAPK, as detected by the anti-active MAPK antibody (see FIG. 8D). Therefore, SL0101-1 does not inhibit upstream kinases necessary for PDB-stimulated RSK phosphorylation, namely MAPK, MEK, Raf and PKC. These data indicate that SL0101-1 is an effective and specific RSK inhibitor in intact cells.

The importance of MAPK to proliferation and oncogenesis is well established. However, the role that RSK plays in these processes has not been examined. Therefore, the effect of SL0101-1 on proliferation of Ha-Ras transformed NIH/3T3 cells and the parental cell line was determined SL0101-1 decreased the growth rate of the transformed cells but had little effect on proliferation of the parental line. SL0101-1 produced striking morphology changes in the transformed cells but not in the parental cell line. The vehicle control treated Ha-Ras transformed cells were elongated whereas in response to SL0101-1 the cells became much larger and flatter, appearing more like the parental cells, or like Ha-Ras transformed cells treated with U0126. Removal of SL0101-1 resulted in growth of the transformed cells (see FIG. 7A) and a reversion to their elongated phenotype. These results demonstrate that SL0101-1 can penetrate intact cells, but is not toxic and preferentially inhibits the growth of oncogene-transformed cells compared to the parental cells.

Whether or not SL0101-1 could inhibit the growth rate of MCF-7 cells, which are more representative of human cancers than the Ha-Ras transformed cell line, was also investigated. Remarkably, SL0101-1 inhibited proliferation of MCF-7 cells but had no effect on the growth of the normal breast cell line, MCF-10A (FIG. 8A), even though SL0101-1 prevented the PDB-induced p140 phosphorylation in MCF-10A cells (FIG. 8D). Furthermore, SL0101-1 inhibits the growth rate of MCF-7 cells at an efficacy that parallels its ability to suppress RSK activity in vivo.

Reduction of RSK1 and RSK2 levels was also accomplished using short, interfering RNAs (siRNA). Specifically, duplex siRNAs to a sequence in the bluescript plasmid (Control) or to RSK1 and RSK2 were transfected into MCF-7 cells. The sense strand for RSK1 has the sequence AAGAAGCUGGACUUCAGCCGU (SEQ ID NO: 1), whereas the sense strand for RSK1 has the sequence AACCUAUGGGAGAGGAGGAGA (SEQ ID NO: 2). Medium was replaced 24 hr post-transfection and the cells incubated for an additional 48 hr prior to measuring cell viability. A combination of siRNAs to both RSK1 and RSK2 was effective in reducing MCF-7 proliferation. The siRNAs were not as effective at inhibiting growth as SL0101-1, however RSK1 and RSK2 expression was not completely eliminated and only about 70% of the cells were transfected. Nonetheless, these results strongly support observations that both RSK1 and RSK2 are important in MCF-7 proliferation.

As further support of the specificity of SL0101-1 action, U0126, the MEK inhibitor, halted proliferation of both MCF-7 and MCF-10A cells (FIG. 8A). Ro 318220 (500 nM), a potent but non-specific PKC inhibitor, which inhibits RSK as well as a number of other AGC kinase family members also attenuated proliferation of both MCF-7 and MCF-10A cells. Moreover, kaempferol, the flavonoid constituent of SL0101-1 slows growth of MCF-10A and MCF-7 cells to the same extent. Therefore, unlike the action of these other kinase inhibitors, SL0101-1 selectively halts proliferation of cancer cells without affecting normal cells.

As shown in FIG. 11 derivatives of SL0101 also inhibit proliferation of MCF-7 breast cancer cells. Compounds tested include: Kaempferol L-carbarhamnoside 4"-acetate (12), Kaempferol L-carbarhamnoside 2",4"-diacetate (13), Kaempferol L-carbarhamnoside 3",4"-diacetate (14), and Kaempferol-6"ethyl-L-rhamnoside-3",4"-diacetate (16).

Methods.

Kinase Assays. Glutathione-5-transferase (GST)-fusion protein (1 g) containing the sequence RRRLASTNDKG (SEQ ID NO: 3, for serine/threonine kinase assays) or VSVSETDDYAEIIDEEDTFT (SEQ ID NO: 4, for tyrosine kinase assays) was adsorbed in the wells of LumiNunc 96-well polystyrene plates (MaxiSorp surface treatment). The wells were blocked with sterile 3% tryptone in phosphate buffered saline and stored at 4° C. for up to 6 months. Kinase (5 nM) in 70 µl of kinase buffer (5 mM-glycerophosphate pH 7.4, 25 mM HEPES pH 7.4, 1.5 mM DTT, 30 mM $MgCl_2$, 0.15 M NaCl) was dispensed into each well. Compound at indicated concentrations or vehicle was added, and reactions were initiated by the addition of 30 µl of ATP for a final ATP concentration of 10 µM unless indicated otherwise. Reactions were terminated after 10 to 45 min by addition of 75 µl of 500 mM EDTA, pH 7.5. All assays measured the initial velocity of reaction. After extensive washing of wells, polyclonal phosphospecific antibody developed against the phosphopeptide and HRP-conjugated anti-rabbit antibody (211-035-109, Jackson ImmunoResearch Laboratories) were used to detect serine phosphorylation of the substrate. HRP-conjugated anti-phospho-tyrosine antibody (RC20, BD Transduction Laboratories) was used for phospho-tyrosine detection. His-tagged active RSK and FAK were expressed in Sf9 cells and purified using NiNTA resin (Qiagen). Baculovirus was prepared using the Bac-to-Bac® baculovirus expression system (Invitrogen). PKA was bacterially expressed and activated as described (Anal. Biochem. 245, 115-122 (1997)). Active Msk1 and p70 S6 kinase was purchased from Upstate Biotechnology. Immunoprecipitation and kinase assays were performed as previously described (Poteet-Smith et al., J. Biol. Chem., 274, 22135-22138 (1999)) using the immobilized GST-fusion proteins and ELISAs as above.

Cell Culture. For proliferation studies cells were seeded at 2500 to 5000 cells per well in 96 well tissue culture plates in the appropriate medium as described by American Type Culture Collection. After 24 hr, the medium was replaced with medium containing compound or vehicle as indicated. Cell viability was measured at indicated time points using CellTiter-Glo™ assay reagent (Promega) according to manufacturer's protocol. For in vivo inhibition studies, cells were seeded at $2.5 \times 10^5$ cells/well in 12 well cell culture clusters. After 24 hr, the cells were serum starved for 24 hr then incubated with compound or vehicle for 3 hr prior to a 30 min PDB stimulation. Cells were lysed as previously described (J. Biol. Chem. 273, 13317-13323 (1998)). The lysates were normalized for total protein, electrophoresed and immunoblotted. For cell imaging, Ha-Ras-transformed NIH/3T3 cells were seeded on LABTEK II chamber slides (Nalge) at a density of $1 \times 10^4$ cells/well. After 24 hr, fresh medium was added the indicated compounds or vehicle. Images were taken 48 hr after treatment at a magnification of 20×.

Gene Silencing. Custom oligonucleotides to RSK1 (AA-GAAGCUGGACUUCAGCCGU; SEQ ID NO: 1 and RSK2 (AACCUAUGGGAGAGGAGGAGA; SEQ ID NO: 2) mRNA (Dharmacon Research Inc.) and TransIT-TKO® siRNA Tranfection Reagent (MIR2150, Minis Corporation) were used for the gene silencing studies. MCF-7 cells were seeded at a density of $1.25 \times 10^4$ cells per well in 24 well cell culture clusters. After 24 hr, fresh medium was added containing 25 nM oligonucleotide and transfection reagent according to manufacturer's protocol. The transfection medium was replaced after 24 hr. Cells were incubated for an additional 48 hr prior to cell viability measurement.

Breast tissue analysis. Frozen tissue samples were ground using mortar and pestle under liquid nitrogen. Ground tissue was added to heated 2-X SDS loading buffer and boiled for 3 min. Protein concentration of lysates was measured and lysates were electrophoresed on SDS-PAGE and immunoblotted.

Example 10

RSK Inhibitors Inhibit Proliferation of Prostate Cancer Cell Line

Prostate cancer is the second most common cancer in men and approximately one in six men will be diagnosed with the disease. Early stage prostate cancer is frequently dependent on the hormone, androgen. Androgen action is mediated through interaction with the androgen receptor, a member of the superfamily of ligand-activated transcription factors. Inhibition of androgen receptor activity by pharmacological or surgical interventions that reduce androgen concentration can result in prostate tumor regression. However, with relatively high frequency the tumors become androgen-independent, which often leads to a fatal outcome. Treatment options are confined to conventional chemotherapy because of the lack of specific drug targets associated with androgen-independent prostate cancer. Thus, elucidation of the mechanisms that result in the transition of prostate cancer from an androgen-dependent to androgen-independent state will greatly facilitate the identification of more effective therapies.

An increase in mitogen-activated protein kinase (MAPK) activity has been correlated to prostate cancer progression in human tumors. This enhanced activity is most likely due to the increase in growth factors and receptors that are known to occur. Activation of growth factor receptors enhance MAPK activity via a kinase cascade that is regulated by the small GTP-binding protein, p21Ras. The family of p90 ribosomal S6 kinases (RSKs), which are Ser/Thr protein kinases, function as downstream effectors of MAPK. The biological actions of the RSKs are not well characterized partly because until recently there were no known inhibitors of RSK that did not also inhibit MAPK activity.

The first RSK-specific inhibitor, SL0101-1 has now been isolated. As described in Examples 9 and 10, SL0101-1 inhibits the proliferation of the breast cancer cell line, MCF-7, without preventing the proliferation of a normal breast cell line, MCF-10A. Furthermore, in NIH 3T3 fibroblasts, SL0101 reduces the growth of a Ha-Ras-transformed line but not of the untransformed parental cells. It is believed that SL0101 specifically inhibits the growth of transformed cells because transformed cells preferentially depend on the RSK pathway to regulate proliferation. These results provide the first demonstration that the RSK family through the regulation of its downstream effectors is involved in the control of cancer cell proliferation. Relatively few downstream effectors of RSK have been identified. However, RSK is known to phosphorylate and regulate the activity of a number of transcription factors, the pro-apoptotic protein, BAD, and the mitotic checkpoint kinase, BUB1. Determining which RSK substrates play a key role in cancer cell proliferation will undoubtedly lead to the discovery of novel drug targets for cancer therapy.

The ability of SL0101-1 to inhibit the proliferation of the androgen-dependent human prostate line, LNCaP was tested. SL0101-1 completely inhibits the proliferation of LNCaP cells (FIG. 8B). This result suggests that the LNCaP line is primarily dependent on RSK activity for growth. To investigate the RSK signal transduction pathway in the LNCaP line, a phosphospecific antibody to a RSK phosphorylation motif (RPM) was produced. Only a few downstream effectors of RSK have been identified and therefore, applicants anticipated that an anti-RPM antibody would be a very effective tool for identifying novel RSK substrates in vivo. An anti-RPM antibody has previously been reported that recognizes the RSK substrate, p140, a protein of unknown function. In agreement with these results SL0101-1 was observed to decrease the phosphorylation of p140 with an efficacy that paralleled its ability to inhibit LNCaP proliferation (see FIGS. 8B and 8D). All lysates were normalized to each other using an anti-Ran antibody. Ran is used for normalization based on the observations that it is a general housekeeping protein, the activity or expression levels of which are not known to vary in any disease state.

Malignant transformation and progression in human cancers are frequently associated with over-abundance or increased activity of proteins that are involved in normal cellular processes. As reported herein, RSKs have been found to be overexpressed in many human breast and prostate cancers, as compared to normal breast and prostate tissue. Lysates were made from the various samples and normalized to each other using an anti-ran antibody. Examination of RSK1 and RSK2 expression in 22 breast cancer samples and 4 normal samples revealed that >50% of the breast cancer tissues have higher RSK expression than the normal samples. RSK1 and RSK2 expression was also examined in 4 prostate cancers, 5 normal and 5 benign hyperplastic (BPH) samples. In general, the cancer tissues have higher levels of RSK expression than the normal and BPH tissue with the exception of one normal sample. However, this sample was removed from tissue that was adjacent to cancerous tissue. Interestingly, phosphorylation of p140 could be detected in normal prostate tissues except for the one normal tissue that also contained a higher level of RSK1 expression. Under the electrophoretic conditions used in this experiment the phosphorylated p140 migrates as a doublet. The cancerous tissue was obtained from tumors with Gleason scores >7, which indicates that the samples are of advanced prostate cancers.

The breast and prostate lysates were also immunoblotted with anti-pan ERK antibody, which recognizes both the active and inactive forms of p42 and p44 MAPK. The relative levels of p42 and p44 MAPK varied considerably between the samples but did not correlate with the extent of RSK overexpression. Thus RSK overexpression is not merely a reflection of overexpression of various members of the MAPK pathway. These results indicate that both RSK1 and RSK2 activity is higher in human breast and prostate cancer tumors than in normal human breast tissue. These results support the use of RSK as a good drug target for breast and prostate cancer, and other cancer types.

Overexpression of the isoform 2 of the RSK family (RSK2) also enhances the transcriptional activity of the estrogen receptor (ERα) and the androgen receptor (AR). A constitutively active mutant of RSK2 was prepared to allow for the study of RSK2's role in ER-mediated transcription in the absence of active MAPK. RSK2 enhanced both ligand-dependent and ligand-independent ER-mediated transcription in MCF-7 cells, a human breast cancer cell line. Additionally, RSK2 enhances the ligand-dependent and ligand-independent transcription of AR-mediated transcription in LNCaP cells, a human prostate cancer cell line. These results are significant because they suggest that the enhanced RSK expression observed in breast and prostate cancer cells may increase ERα or AR transcriptional activity. Increased activities of the ERα and AR are known to be important in the etiology of some breast and prostate cancers, respectively.

Example 11

Rhamnose Acylation is Critical for Inhibition of MCF-7 Cell Growth

To investigate the possibility of improving the potency of SL0101, two compounds structurally related to SL0101 were prepared and characterized for their ability to inhibit RSK activity. These compounds, kaempferol 3-O-(2",4"-di-O-acetyl-.alpha.-L-rhamnopyranoside), (2",4"-di-O-acetyl-SL0101), and kaempferol 3-O-(4"-mono-O-acetyl-.alpha.-L-rhamnopyranoside), (4"-mono-O-acetyl-SL0101), differ from SL0101 in either the position or number of acetyl groups present on the rhamnose moiety and were obtained during the purification of SL0101 from F. refracta. The ability of the purified compounds to inhibit RSK activity was determined in an in vitro kinase assay using recombinant, constitutively active RSK2. The data were fit using non-linear regression analysis and the $IC_{50}$ values for 4"-mono-O-acetyl-SL0101 and 2",4"-di-O-acetyl-SL0101 were about 140 nM and about 260 nM, respectively, which is similar to the $IC_{50}$ of about 50-100 nM obtained for SL0101. Thus all three related compounds are able to inhibit RSK catalytic activity in vitro.

To determine whether the related compounds inhibit RSK activity in intact cells we examined their ability to inhibit the proliferation of MCF-7 cells. As noted in Examples 9 and 10, SL0101 inhibited MCF-7 cell proliferation with an $EC_{50}$ of about 50 uM, and the current results are in agreement with those observations. SL0101 and 2",4"-di-O-acetyl-SL0101 at 50 uM were similarly effective at inhibiting MCF-7 cell growth. However, 4" mono-O-acetyl-SL0101 did not inhibit MCF-7 cell proliferation at 50 uM. These data show that the position of the acetyl groups was not critically important in determining the in vitro affinity for RSK. However, only the compounds with two acetyl groups inhibited RSK activity in intact cells. It is likely that the acetyl groups facilitate effective uptake of the inhibitors into the cell.

Figure 5A:
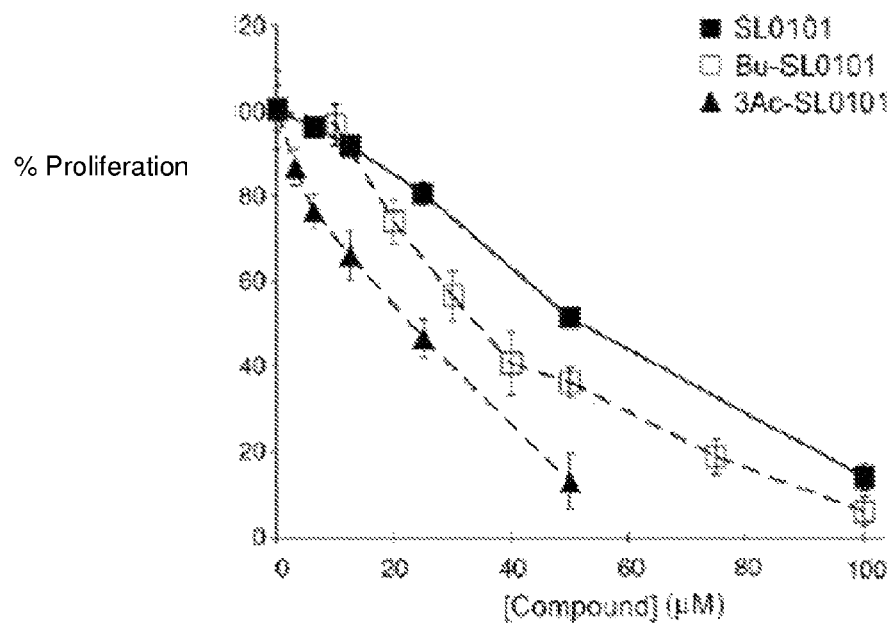
Figure 5B:
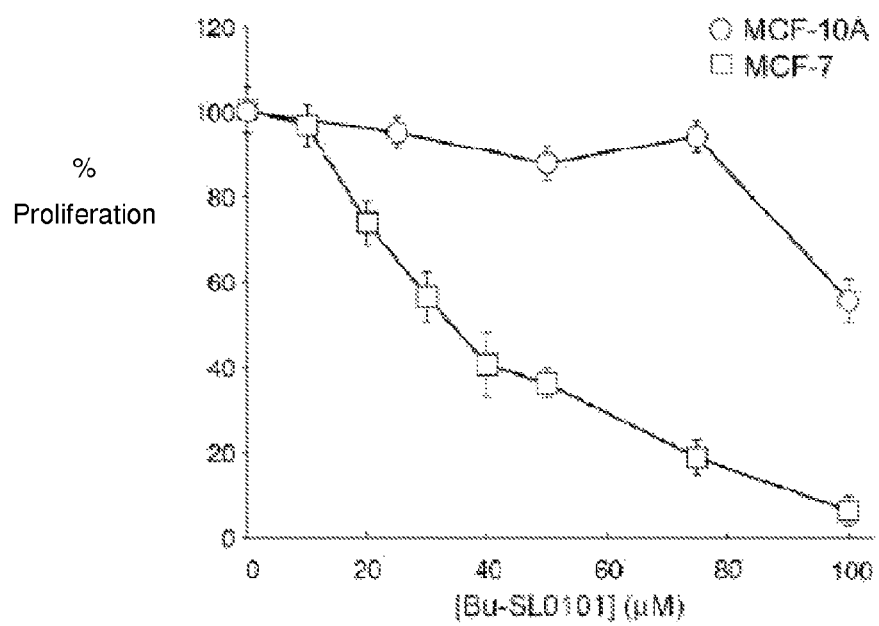
Figure 5C:
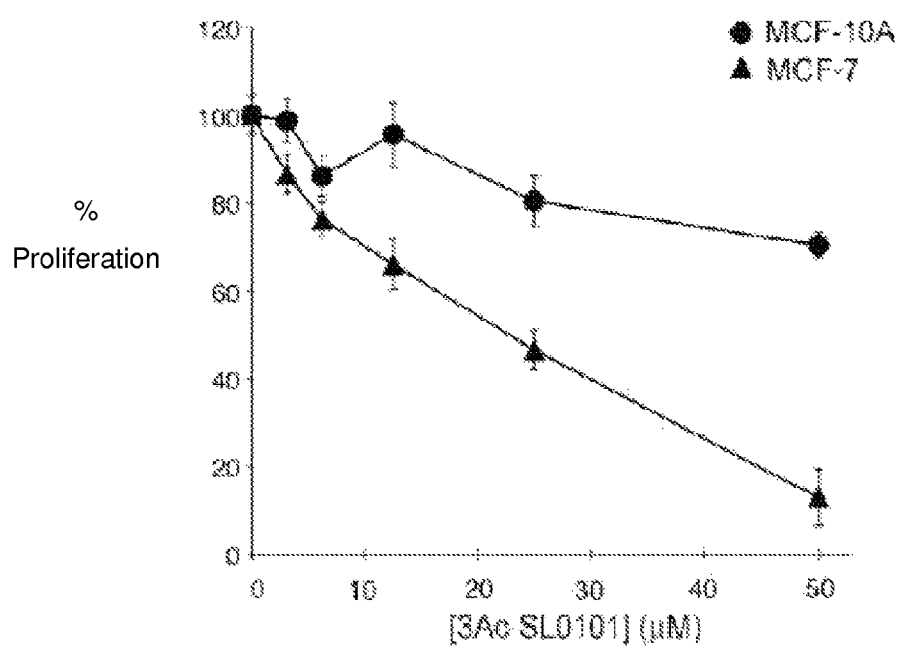

Based on the results disclosed herein, it was reasoned that increasing the cellular uptake of SL0101 by enhancing its hydrophobic, character might afford a more potent RSK inhibitor in intact cells. To test this hypothesis kaempferol 3-O-(3",4"-di-O-butyryl-.alpha.-L-rhamnopyranoside) (Bu-SL0101) and kaempferol 3-O-(2",3",4"-tri-O-acetyl-.alpha.-L-rhamnopyranoside) (3Ac-SL0101) were synthesized. The calculated Log Ps of Bu-SL0101 and 3Ac-SL0101 are 4.30 and 3.07, respectively, compared to 2.56 for SL0101. Data from these experiments is presented in FIGS. 5A-5C.

Example 12

RSK Activity Required for Human Umbilical Vein Endothelial Cell (HUVEC) Migration The data produced by the experiments described herein demonstrate that RSK activity is required for migration of human umbilical vein endothelial cells (HUVEC). Migration and invasion of the endothelial cells are the initial steps in angiogenesis. Therefore, treatments that stop migration of endothelial cells will inhibit formation of new vessels from the existing vasculature.

First, it was found that treatment of HUVEC cells with the RSK-specific inhibitor, SL0101, does not alter the rate of HUVEC cell growth, but does reduce the ability of the cells to migrate into and close a wound made in a confluent monolayer of cells. In these experiments, HUVEC were cells were subcultured to confluence in 35-mm plates. One hour prior to wounding, the cells were treated with vehicle or 60 µM SL0101. Scratches were made in the monolayer of cells using sterile, disposable micropipette tips. Images were captured—2 hr, 10 hr, and 20 hr after wounding. By 10 hr after wounding, the vehicle-treated cells at the wound edge have migrated toward the wound. Gaps in the monolayer behind the wound edge are apparent. The SL0101-treated cells have recovered from the wounding, however they show little signs of polarization toward the wound and no involvement of the cells behind the wound edge. At 20 hr, the vehicle-treated cells have migrated into the wound yet the gaps are still present behind the wound edge. The cells at the wound edge in the SL0101-treated well appear to have increased in size to fill the wound rather than migrate into the wound and the monolayered cells behind the wound edge remain tightly packed unlike the vehicle-treated cells. Accordingly the data support the premise that RSK inhibitors are useful tools to stop endothelial cell migration.

To demonstrate that the concentration of SL0101 used in the wound healing assay was sufficient to inhibit RSK activity in the HUVEC cells, the phosphorylation state of a known RSK substrate, pp 140 was examined. HUVEC cells were seeded at a density of $3 \times 10^5$ cells per 35 mm dish and were maintained in complete growth medium. Twenty-four hours after plating, the cells were incubated for an additional 2 hr in the presence or absence of 60 µM SL0101. After the 2 hr incubation in the presence or absence of SL0101, a subset of cells from each group was challenged with 500 nM phorbol dibutyrate for 30 min to maximally stimulate RSK activity. The cells were harvested and lysates prepared for SDS-PAGE and immunoblot analysis. The phosphorylation state of pp 140 was determined using a phosphospecific antibody generated against the phosphorylated peptide—LAS(P)TND. Equal loading of lysate is demonstrated by the Ran immunoblot.

SL0101 treatment was observed to reduced the phosphorylation of pp 140. Basal phosphorylation of pp 140 induced by complete growth medium is eliminated by SL0101 treatment. SL0101 treatment also inhibited activation of RSK by PDB-challenge. Thus, SL0101 inhibits RSK activity in the HUVEC cells.

Example 13

RSK Activity Required for Human Metastatic Non Small Cell Lung Cancer Cell Line (CaLu-1) Migration As further proof of RSK's role in migration, further experiments were conducted demonstrating that inhibiting RSK activity with SL0101 in the human metastatic non small cell lung cancer cell line, CaLu-1 generates the same phenotype as silencing RSK expression using small interfering RNA.

CaLu-1 cells were sub-cultured to confluence in 35-mm plates. One hour prior to wounding, the cells were treated with vehicle or 60 µM SL0101. Scratches were made in the monolayer of cells using sterile, disposable micropipette tips. Images were captured either immediately following the wounding, 6 hr, or 24 hours after wounding. At the point of wounding, the cells at the wound edge show increased light refraction indicating damage. By 6 hr after wounding, the vehicle-treated cells at the wound edge present wide lamella (indicated by arrows) extending toward the direction of the wound. The SL0101-treated cells have recovered from the wounding as evidenced by reduced refractivity at the wound edge; however, they showed no signs of polarization toward the wound. At 24 hr, the vehicle-treated cells have migrated into the wound and are enlarged to re-form the confluent monolayer. However, the SL0101-treated cells have not migrated to close the wound.

Example 14

Reducing RSK Expression in the Human Lung Cancer Cell Line, Calu-1, Inhibits Migration into the Wound Calu-1 cells were transiently transfected in suspension with either control siRNA, RSK1-specific siRNA, RSK2-specific siRNA or both RSK-1 and RSK2-specific siRNA.

Custom oligonucleotides to Rsk1 (AAGAAGCUGGACU-UCAGCCGU; SEQ ID NO: 1 and Rsk2 (AACCUAUGG-GAGAGGAGGAGA; SEQ ID NO: 2) mRNA (Dharmacon Research Inc.) and Lipofectamine™ 2000 (Invitrogen Corporation Carlsbad, Calif. 92008) transfection reagent were used for the gene silencing studies.

After four hours, the transfection medium was removed and the cells were plated in E-well tissue-culture clusters. Forty-eight hours after transfection, scratches were made in the monolayer of cells using sterile, disposable micropipette tips. Images were captured—immediately following the wounding, and 19 hours after wounding. The images demonstrate classical wound healing. By 19 hr, the cells transfected with control siRNA have migrated into the wound. However, the cells transfected with either RSK1- or RSK2-specific siRNA demonstrate a reduced ability to migrate into the wound. Interfering with the expression of both RSK1 and RSK2 also results in reduced migration. Thus, RSK activity is required for Calu-1 migration. More particularly, the ability of the entire monolayer to respond to the wound is depressed in the SL0101-treated cells as well as the siRNA transfected.

Example 15

SL0101 Reduces Expression of the Angiogenesis Marker, VCAM

HUVEC cells were treated in the presence or absence of 1 µg/ml lipopolysaccharide (LPS) with concomitant treatment with vehicle or SL0101. Twenty-four hours after LPS treatment, the cells were harvested with SDS lysis buffer in preparation for SDS-PAGE and immunoblot analysis. Lysates were normalized with regard to protein concentration. Equivalent loading was confirmed by use of an anti-Ran immunoblot. The data demonstrates that inhibition of RSK activity with SL0101 reduced expression of the angiogenesis marker VCAM in a dose-dependent manner.

Example 16

Capillary Network Formation in HUVEC Cells

To further characterize the RSK inhibitor, the effect of SL0101 on development of capillary-like tube formation in HUVEC cells was examined. Interfering with tube formation is a characteristic common to anti-angiogenic treatments. HUVEC cells were seeded at a density of $1 \times 10^5$ cells per well in 24-well culture dishes coated in growth factor-reduced Matrigel (BD Biosciences). The cells were treated with vehicle, 60 µM SL0101 or 20 µM SU1498 (VEGF receptor inhibitor) for 30 minutes prior to stimulation with 10 ng/ml of VEGF. The cells were incubated at 37° C. for 20 hours. Images of the cells were captured for analysis of the capillary-like network.

Stimulation of HUVEC cells with VEGF resulted in accumulation of the cells into flat, polymorphous nodes with multiple tube-like connections between nodes. Treatment of HUVEC cells with VEGF in the presence of SU1498, the VEGF Receptor inhibitor, resulted in accumulation of the cells into rounded nodes with few tube-like projections. HUVEC cells treated with VEGF in the presence of SL0101, the RSK inhibitor, were indistinguishable from those treated with SU1498. A few flat nodes with multiple tube-like projections were observed in the SU1498-treated cells and SL0101-treated cells, however, the majority of the nodes in the inhibitor-treated cells were rounded with few projections. Thus, the results from these experiments support the results obtained in Examples 13-16 indicating that inhibition of RSK activity is sufficient to limit VEGF-induced capillary network formation in HUVEC cells.

Example 17

Assessing the Ability of SL0101 Derivative Compounds to Inhibit RSK Activity

Kinase assays were performed using immobilized substrate. RSK was incubated in the presence of 500 nM of each SL0101 derivative compound. The compounds tested include Kaempferol L-rhamnoside (4), Kaempferol L-rhamnoside 4"-acetate (5), Kaempferol L-rhamnoside 2",4"-diacetate (6), Kaempferol L-rhamnoside 3",4"-diacetate (7), Kaempferol L-rhamnoside 2",3",4"-triacetate (8), Kaempferol L-carbarhamnoside 4"-acetate (12), Kaempferol L-carbarhamnoside 2",4"-diacetate (13), Kaempferol L-carbarhamnoside 3",4"-diacetate (14), Kaempferol-6"ethyl-L-rhamnoside-2",4"-diacetate (15), Kaempferol-6"ethyl-L-rhamnoside-3",4"-diacetate (16), Kaempferol-6"ethyl-L-rhamnoside (17), Kaempferol-6"ethyl-L-rhamnoside-2",3",4"-triacetate (18), Kaempferol-6"ethyl-L-rhamnoside-2"-monoacetate (19), Kaempferol-6"ethyl-L-rhamnoside-4"-monoacetate (20), Kaempferol-6"methyl-L-rhamnoside (21), Kaempferol-6"isopropyl-L-rhamnoside (22).

Reactions were initiated by the addition of 10 micromoles/L ATP (final concentration) and terminated after 10 minutes. All assays measured the initial reaction velocity. Extent of immobilized substrate phosphorylation was determined using phosphospecific antibodies in combination with HRP-conjugated secondary antibodies. Maximum and minimum activity is the relative luminescence detected in the presence of vehicle and 200 mmol/L EDTA, respectively. Data are presented as percentage of maximum activity (See FIG. 9). Columns, mean of quadruplicates; bars, SD. Each of the tested compounds demonstrated superior inhibitory activity relative to SL0101, with compounds 15 and 16 demonstrating a surprising >2× higher inhibitory activity than SL0101.

Example 18

Determining the Concentration of Compound Required to Inhibit RSK Activity by 50% ($IC_{50}$)

Kinase assays were performed using immobilized substrate. RSK was incubated in the presence of indicated concentrations of each compound. Reactions were initiated by the addition of 10 micromoles/L ATP (final concentration) and terminated after 10 minutes. All assays measured the initial reaction velocity. Extent of immobilized substrate phosphorylation was determined using phosphospecific antibodies in combination with HRP-conjugated secondary antibodies. Maximum and minimum activity is the relative luminescence detected in the presence of vehicle and 200 mmol/L EDTA, respectively. Kinase activity measured in the presence of the compound is presented as the percentage of maximum activity. Points are mean of quadruplicates; bars, SD. The $IC_{50}$ of each compound is determined to be: #16, 100 nM; #14, 220 nM; #17, 300 nM; #17, 1 µM; and #4, 13 µM (See FIG. 10).

Example 19

Efficacy of the Compounds for Inhibiting MCF-7 Cell Growth

MCF-7 cells were treated with vehicle or indicated concentration of compounds, and cell viability was measured after 48 hours of treatment. Values presented are fold proliferation as a percentage of that observed with vehicle-treated cells. Points, mean (n=2 in triplicate); bars, SD. Compounds #13, #14 and #16 inhibit the proliferation of MCF-7 cells by 50% at concentrations of approximately 30 µM (See FIG. 11).

The disclosures of each and every patent, patent application, and publication cited herein are hereby incorporated by reference herein in their entirety.

Headings are included herein for reference and to aid in locating certain sections. These headings are not intended to limit the scope of the concepts described therein under, and these concepts may have applicability in other sections throughout the entire specification.

While this invention has been disclosed with reference to specific embodiments, it is apparent that other embodiments and variations of this invention may be devised by others skilled in the art without departing from the true spirit and scope of the invention.

What is claimed is:

1. A RSK inhibitor represented by the general structure of Formula III

[Structure III: a flavonoid-type structure with substituents $R_1, R_3, R_5, R_6, R_7, R_8, R_9$ on the aromatic rings, a central pyranone with a carbonyl and an O-linked sugar bearing $R_{10}, R_{11}, R_{20}$ and X, with a propyl group]

wherein $R_1$, $R_3$ and $R_7$ are each hydroxyl;

$R_5$, $R_6$, $R_8$ and $R_9$ are each hydrogen;

$R_{10}$, $R_{11}$ and $R_{20}$ are independently selected from the group consisting of hydroxyl, —NHOCOR$_{14}$, —OCOR$_{14}$, —COR$_{14}$ and $C_1$-$C_4$ alkoxy;

X is O or $CH_2$; and $R_{14}$ is selected from the group consisting of hydrogen, and $C_1$-$C_4$ alkyl.

2. The RSK inhibitor of claim 1 wherein $R_{10}$, $R_{11}$ and $R_{20}$ are independently selected from the group consisting of hydroxyl and —OCOR$_{14}$, wherein at least one of $R_{10}$, $R_{11}$ and $R_{20}$ is hydroxyl.

3. The RSK inhibitor of claim 2 wherein one of $R_{10}$ and $R_{11}$ is —OCOCH$_3$ and the other is hydroxyl.

4. The RSK inhibitor of claim 1 wherein the inhibitor comprise the general structure of Formula IV:

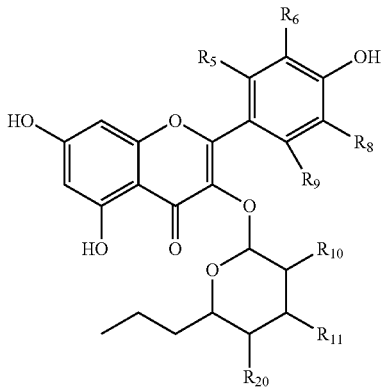

wherein $R_5$, $R_6$, $R_8$ and $R_9$ are each hydrogen;

$R_{10}$, $R_{11}$ and $R_{20}$ are independently selected from the group consisting of —$OCOR_{14}$, —$COR_{14}$ and hydroxyl, and $R_{14}$ is selected from the group consisting of hydrogen and $C_1$-$C_4$ alkyl.

5. The RSK inhibitor of claim 4 wherein
at least one of $R_{10}$, $R_{11}$ and $R_{20}$ is —$OCOCH_3$, and at least one of $R_{10}$, $R_{11}$ and $R_{20}$ is hydroxyl.

6. The RSK inhibitor of claim 5 wherein $R_{20}$ is $OCOCH_3$, and one of $R_{10}$ and $R_{11}$ is $OCOCH_2$, and the other is hydroxyl.

7. The RSK inhibitor of claim 4 wherein $R_{11}$ and $R_{20}$ are both $OCOCH_3$, and $R_{10}$ is hydroxyl.

8. A pharmaceutical composition comprising a RSK specific inhibitor of claim 1 and a pharmaceutically acceptable carrier.

9. The composition of claim 8, further comprising an anti-tumor agent.

10. A method of specifically inhibiting RSK activity, said method comprising the step of contacting a RSK enzyme with the RSK specific inhibitor of claim 1.

11. A method for treating a disease or condition characterized by inappropriate RSK activation, said method comprising the step of administering to a human or other mammal in need thereof, a composition comprising the RSK specific inhibitor of claim 6 in an amount effective for specifically inhibiting RSK activity in the cells of said human or mammal.

12. The method of claim 11 wherein the disease is a neoplastic disease.

13. The method of claim 12 further comprising the step of administering to said patient in an anti-tumour therapy.

* * * * *

UNITED STATES PATENT AND TRADEMARK OFFICE
CERTIFICATE OF CORRECTION

PATENT NO. : 9,040,673 B2  
APPLICATION NO. : 13/390389  
DATED : May 26, 2015  
INVENTOR(S) : Hecht et al.

Page 1 of 1

It is certified that error appears in the above-identified patent and that said Letters Patent is hereby corrected as shown below:

In the claims,

In Claim 6, Column 74, Line 5, please delete "$OCOCH_2$" and insert -- $OCOCH_3$ -- therefor.

Signed and Sealed this
Sixth Day of October, 2015

Michelle K. Lee
*Director of the United States Patent and Trademark Office*

SEQUENCE LISTING

```
<160> NUMBER OF SEQ ID NOS: 4

<210> SEQ ID NO 1
<211> LENGTH: 21
<212> TYPE: RNA
<213> ORGANISM: Homo sapiens

<400> SEQUENCE: 1
aagaagcugg acuucagccg u                                              21

<210> SEQ ID NO 2
<211> LENGTH: 21
<212> TYPE: RNA
<213> ORGANISM: Homo sapiens

<400> SEQUENCE: 2
aaccuauggg agaggaggag a                                              21

<210> SEQ ID NO 3
<211> LENGTH: 11
<212> TYPE: PRT
<213> ORGANISM: Homo sapiens

<400> SEQUENCE: 3

Arg Arg Arg Leu Ala Ser Thr Asn Asp Lys Gly
1               5                   10

<210> SEQ ID NO 4
<211> LENGTH: 20
<212> TYPE: PRT
<213> ORGANISM: Homo sapiens

<400> SEQUENCE: 4

Val Ser Val Ser Glu Thr Asp Asp Tyr Ala Glu Ile Ile Asp Glu Glu
1               5                   10                  15

Asp Thr Phe Thr
            20
```